United States Patent
Pal et al.

(10) Patent No.: US 11,739,096 B2
(45) Date of Patent: Aug. 29, 2023

(54) 5-(2,5-DIFLUOROPHENYL)PYRROLIDIN-1-YL)-3-(1H-PYRAZOL-1-YL)PYRAZOLO[1,5-A]PYRIMIDINE DERIVATIVES AND RELATED COMPOUNDS AS TRK KINASE INHIBITORS FOR TREATING CANCER

(71) Applicant: PYRAMID BIOSCIENCES, INC., Waltham, MA (US)

(72) Inventors: Kollol Pal, Needham, MA (US); Stephane Ciblat, Montreal (CA); Vincent Albert, Rigaud (CA); Nicolas Bruneau-Latour, Pointe-Fortune (CA); Jonathan Boudreault, L'Ile-Perrot (CA)

(73) Assignee: Pyramid Biosciences, Inc., Waltham, MA (US)

( * ) Notice: Subject to any disclaimer, the term of this patent is extended or adjusted under 35 U.S.C. 154(b) by 0 days.

(21) Appl. No.: 18/078,087

(22) Filed: Dec. 8, 2022

(65) Prior Publication Data

US 2023/0124248 A1  Apr. 20, 2023

Related U.S. Application Data

(63) Continuation of application No. 17/533,954, filed on Nov. 23, 2021, which is a continuation of application No. 16/772,253, filed as application No. PCT/US2018/065187 on Dec. 12, 2018, now Pat. No. 11,230,546.

(60) Provisional application No. 62/599,490, filed on Dec. 15, 2017.

(51) Int. Cl.
  *C07D 487/04* (2006.01)
  *A61P 35/00* (2006.01)

(52) U.S. Cl.
  CPC ............ *C07D 487/04* (2013.01); *A61P 35/00* (2018.01)

(58) Field of Classification Search
  CPC .................................. C07D 487/04; A61P 35/00
  See application file for complete search history.

(56) References Cited

U.S. PATENT DOCUMENTS

| | | |
|---|---|---|
| 2011/0166133 A1 | 7/2011 | Albaugh et al. |
| 2016/0185785 A1 | 6/2016 | Ioannidis et al. |
| 2021/0094956 A1 | 4/2021 | Pal et al. |
| 2022/0023055 A1* | 1/2022 | Deransart ............ A61F 2/4014 |

FOREIGN PATENT DOCUMENTS

| | | |
|---|---|---|
| AE | P6000859/2020 | 12/2018 |
| AT | 18836977.1 | 12/2018 |
| AU | 2018383571 | 12/2018 |
| AU | 2021255613 | 4/2021 |
| BE | 18836977.1 | 12/2018 |
| BG | 18836977.1 | 12/2018 |
| BR | 112020011775-7 | 12/2018 |
| BR | 112022020114-1 | 4/2021 |
| CA | 3084814 | 12/2018 |
| CA | 3172681 | 4/2021 |
| CH | 18836977.1 | 12/2018 |
| CN | 201880080978.X | 12/2018 |
| CN | 202180024618.X | 4/2021 |
| CZ | 18836977.1 | 12/2018 |
| DE | 18836977.1 | 12/2018 |
| DK | 18836977.1 | 12/2018 |
| EA | 202091475 | 12/2018 |
| EP | 18836977.1 | 12/2018 |
| EP | 22152688.2 | 12/2018 |
| EP | 21787908.9 | 4/2021 |
| ES | 18836977.1 | 12/2018 |
| FI | 18836977.1 | 12/2018 |
| FR | 18836977.1 | 12/2018 |
| GB | 18836977.1 | 12/2018 |
| GR | 18836977.1 | 12/2018 |
| HK | 18836977.1 | 12/2018 |
| HU | 18836977.1 | 12/2018 |
| ID | P00202004777 | 12/2018 |
| IE | 18836977.1 | 12/2018 |
| IL | 275059 | 12/2018 |
| IL | 296921 | 4/2021 |
| IN | 202017024863 | 12/2018 |
| IN | 202217056528 | 4/2021 |
| IS | 18836977.1 | 12/2018 |
| IT | 18836977.1 | 12/2018 |
| JP | 2011520887 A | 7/2011 |

(Continued)

OTHER PUBLICATIONS

U.S. Appl. No. 62/599,490, filed Dec. 15, 2017, Kollol Pal.

(Continued)

*Primary Examiner* — Erich A Leeser
(74) *Attorney, Agent, or Firm* — Ballard Spahr LLP

(57) ABSTRACT

The application relates to pyrazolo[1,5-a]pyrimidine derivatives of formula (IV) as Trk kinase inhibitors for treating cancer and inflammatory diseases.

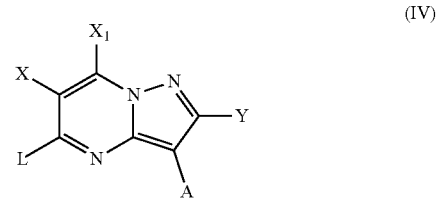

(IV)

2 Claims, No Drawings

(56) References Cited

FOREIGN PATENT DOCUMENTS

| | | | | |
|---|---|---|---|---|
| JP | 2020-551775 | 12/2018 | | |
| JP | 2022-559980 | 4/2021 | | |
| KR | 10-2020-7020360 | 12/2018 | | |
| KR | 10-20227033977 | 4/2021 | | |
| MX | MX/a/2020/006293 | 12/2018 | | |
| MX | MX/A/2022/012437 | 4/2021 | | |
| NL | 18836977.1 | 12/2018 | | |
| NO | 18836977.1 | 12/2018 | | |
| NZ | 792295 | 4/2021 | | |
| PL | 18836977.1 | 12/2018 | | |
| PT | 18836977.1 | 12/2018 | | |
| RO | 18836977.1 | 12/2018 | | |
| SA | 520412192 | 12/2018 | | |
| SE | 18836977.1 | 12/2018 | | |
| SG | 10202250798 T | 12/2018 | | |
| SG | 11202005237 S | 12/2018 | | |
| SG | 11202253641 W | 4/2021 | | |
| TR | 18836977.1 | 12/2018 | | |
| TW | 107144769 | 12/2018 | | |
| WO | WO 2009/140128 A2 | 11/2009 | | |
| WO | WO 2010/048314 A1 | 4/2010 | | |
| WO | WO 2010/051549 A1 | 5/2010 | | |
| WO | WO 2016/097869 | * | 6/2016 | ........... C07D 487/04 |
| WO | WO 2016/0185785 | 11/2016 | | |
| WO | PCT/US2018/065187 | 12/2018 | | |
| WO | WO 2019/118584 | 6/2019 | | |
| WO | PCT/US2021/027538 | 4/2021 | | |
| WO | WO 2021/211882 | 10/2021 | | |
| ZA | 2020/03483 | 12/2018 | | |
| ZA | 2022/05900 | 12/2018 | | |
| ZA | 2022/09792 | 4/2021 | | |

OTHER PUBLICATIONS

U.S. Appl. No. 16/772,253 (U.S. Pat. No. 11,230,546), filed Dec. 12, 2018, Kollol Pal.

U.S. Appl. No. 17/533,954 (2022023055), filed Nov. 23, 2021, Kollol Pal.

U.S. Appl. No. 63/010,108, filed Apr. 15, 2020, Kollol Pal.

U.S. Appl. No. 17/918,880, filed Apr. 15, 2021, Kollol Pal.

Amatu, et al. "NTRK gene fusions as novel targets of cancer therapy across multiple tumour types", ESMO Open 2016; 1:e000023.

Liu, et al. "Entrectinib: an orally available, selective tyrpsine kinase inhibitor for the treatment of NTRK, ROSI, and ALK fusion-positive solid tumors" (2018) *Ther Clin Risk Manag* 14: 1247-1252.

Thiele, C. J., et al., (2009) "on Trk—The TrkB Signal Transduction Pathway is an Increasingly Important Target in Cancer Biology," *Clin Cancer Res*, 15(19): 5962-5967.

Vaishnavi, A., et al. (2014) "TRKing Down an Old Oncogene in a New Era of Targeted Therapy," *Cancer Discov*, 5(1):25-34.

* cited by examiner

5-(2,5-DIFLUOROPHENYL)PYRROLIDIN-1-YL)-3-(1H-PYRAZOL-1-YL)PYRAZOLO[1,5-A]PYRIMIDINE DERIVATIVES AND RELATED COMPOUNDS AS TRK KINASE INHIBITORS FOR TREATING CANCER

RELATED APPLICATION

The application is continuation of U.S. application Ser. No. 17/533,954, filed on Nov. 23, 2021, which is a continuation of U.S. application Ser. No. 16/772,253, filed on Jun. 12, 2020, which is a national stage filing under 35 U.S.C. § 371 of International Application No. PCT/US2018/065187, filed on Dec. 12, 2018, which claims the benefit of U.S. Provisional Application No. 62/599,490, filed on Dec. 15, 2017, the contents of which are incorporated herein by reference in their entireties.

FIELD OF DISCLOSURE

The present application is directed to inhibitors of tropomyosin kinases (Trk) useful in the treatment of diseases or disorders associated with Trk kinases or Trk kinase fusions. Specifically, the application is concerned with compounds and compositions thereof, which inhibit Trk kinases or Trk kinase fusions, methods of treating diseases or disorders associated with Trk kinases or Trk kinase fusions, and methods of synthesis of these compounds.

BACKGROUND OF THE APPLICATION

The tropomyosin kinase receptor family includes TrkA, TrkB, TrkC and p75 and serves as high affinity cell surface receptors for the growth factors NGF, BDNF, NTS and NT4, respectively. The Trk signaling pathway is regulated by a number of intracellular signaling cascades which include protein products encoded by proto-oncogenes and tumor suppressor genes, most of which are essential for neuronal development and tumorigenesis (see, e.g., C Thiele, et. al. (2009) *Clin. Cancer Res.* 15: 5962). Growth factors are important signaling molecules that promote the growth, development and homeostasis of cellular systems. Inhibition of these receptors may lead to the modulation or inhibition of intracellular signaling cascades that regulate cell growth and proliferation, cellular communication between cells that regulate signaling, feedback mechanism and homeostasis. These growth factors have been implicated in the growth and proliferation of both neuronal and non-neuronal cells.

Advances in the detection of oncogenic mutations in tumors revealed onogenic alterations, such as gene fusions, for the genes encoding TrkA (NTRK1), TrkB (NTRK2), and TrkC (NTRK3) receptor tyrosine kinases across multiple tumor types (see, Vaishnavi, A. et al (2015) *Cancer Discov.* 5(1): 1-10). Such gene fusions have been detected in a wide variety of cancer types and may be viable targets for precision chemotherapies. For example, the TPM3-NTRK1 gene fusion was found to be prevalent in colorectal cancer and lung adenocarcinoma cells, whereas the ETV6-NTRK3 gene fusion was found to be the dominant gene fusion in malignancies such secretory breast carcinoma and mammary analogue secretory carcinoma (MASC).

Inhibition of Trk with small molecule inhibitors therefore has the potential to be a treatment for inflammatory diseases, infections, autoimmune disorders, stroke, ischemia, cardiac disorder, neurological disorders, dermatological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atopic dermatitis, pruritis, eczema, Gorlin Syndrome, Netherton Syndrome, basal cell carcinoma, dermaiomyocytis, cylindromas, atherosclerosis, rheumatoid arthritis, osteoarthritis, heart failure, chronic pain, neuropathic pain and other disorders. For this reason, there remains a considerable need for potent small molecule inhibitors of Trk kinases.

SUMMARY OF THE APPLICATION

A first aspect of the application relates to compounds of formula (IV):

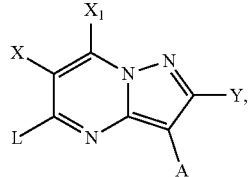

(IV)

and pharmaceutically acceptable salts, hydrates, solvates, isotopes, prodrugs, stereoisomers, and tautomers thereof, wherein:

X is H, (Ci-Cb) alkyl, or halogen;

$X_2$ is or D;

Y is H, D, C1-C6 alkyl, or CN;

L is

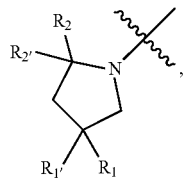

—O(CR$_3$R$_4$)—(C$_6$-C$_{10}$) aryl, —NR5~(CR$_3$R$_4$)—(C6-C$_{10}$) aryl, -Q(CR 3R$_4$)-5~ or 6-membered heteroaryl, or —NR=$_5$—(CR3R4)-5~ or 6-membered heteroariyl, wherein the aiyl and heteroaryl are optionally substituted with one or more Rr;

each Ri and Rris independently H, (Ci-Ce) alkyl, (Ci-Cb) alkoxy, (Ci-Cb) haloalkyl, (Ci-Cb) haloalkoxy, halogen, or —OH;

$R_2$ is (Cb-Cio) aryl or 5- or 6-membered heteroaryl, wherein the aryl and heteroaryl are optionally substituted with one or more R?;

R2' is H, D, (Ci-Cb) alkyl, or halogen;

each $R_3$, $R_4$ and $R_5$ at each occurrence is independently H or (Ci-Cb) alkyl;

each Reis independently at each occurrence (Ci-Cb) alkyl, (Ci-Cb) alkoxy, (Ci-Cb) haloalkyl, (Ci-Ce) haloalkoxy, or halogen;

each $R_7$ is independently at each occurrence (Ci-Ce) alkyl, (Ci-Ce) alkoxy, (Ci-Cb) haloalkyl, (Ci-Ce) haloalkoxy, or halogen;

A is

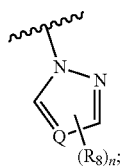

Q is N or CRs;

each of $R_8$ and $R_9$, at each occurrence, independently is H, halogen, cyano, (Co-Cb)alkyl-$OR^a$, (Co—C6)alkyl-$NR^aR^b$, (Co—C6)alkyi-C(O)R (Co—C6)alkyl-$P(O)R^aR^n$, (Co—Ce)aikyl-S(Q)pR, $NW^2C(O)R$ NWS(0)?.R", or $R^W$, or $R_g$ and $R_9$, together with the atoms to which they are attached, form a 5- to 7-membered ring optionally comprising one or more heteroatoms selected from N, O, and S and optionally substituted with one or more $R^{S1}$;

each $R^w$ independently is (Ci-Cb) alkyl, (Ci-Cb) haloalkyl, (Cs—Cs) cycloalkyl, 3- to 8-membered heterocycloalkyl, (Cb-Cio) aryl, or 5 to 10-membered heteroaryl, each of which is optionally substituted with one or more $R^{S2}$;

each of $R^{S1}$ and $R^{S2}$, at each occurrence, independently is H, halogen, cyano, (Ci-Cb) alkyl, (Ci-Cb) haloalkyl, (Co—C3)alkyl-$OR^C$, (Co—C3)alkyl-$NR^cR^d$, $C(O)OR^e$, or $C(O)NR^cR^d$;

each of $R^3$, $R^b$, $R^c$ and $R^d$ independently is $R^i$, (Cg-Cg) cycloalkyl, 3- to 8-membered heterocycloalkyl, (Co-Csj alkyl-$OR^8$, or (Co—C3)alkyl-$NR^gNR^h$, or R" and $R^b$ or and $R^d$ together with the atoms to which they are attached form a 5 to 7-membered ring optionally comprising one or more heteroatoms selected from N, O, and S;

each of $R^e$, $R^f$, $R^g$, $R^h$, $R^i$, and R independently is H, (Ci-Cb) alkyl or (Ci-Cb) haloalkyl;

n is 0, 1, or 2; and p is 0, 1, or 2.

Another aspect of the application relates to a method of treating a disease or disorder associated with the inhibition of a tropomyosin kinase (Trk). The method comprises administering to a patient in need of a treatment for diseases or disorders associated with modulation of a tropomyosin kinase an effective amount of a compound of Formula (IV), or a pharmaceutically acceptable salt, hydrate, solvate, prodrug, stereoisomer, or tautomer thereof.

Another aspect of the application relates to a method of treating a disease or disorder associated with the inhibition of one or more tropomyosin kinases (Trk). The method comprises administering to a patient in need of a treatment for diseases or disorders associated with modulation of a tropomyosin kinase an effective amount of a compound of Formula (IV), or a pharmaceutically acceptable salt, hydrate, solvate, prodrug, stereoisomer, or tautomer thereof.

Another aspect of the application relates to a method of preventing a disease or disorder associated with the inhibition of a tropomyosin kinase (Trk). The method comprises administering to a patient in need of a treatment for diseases or disorders associated with modulation of a tropomyosin kinase an effective amount of a compound of Formula (IV), or a pharmaceutically acceptable salt, hydrate, solvate, prodrug, stereoisomer, or tautomer thereof.

Another aspect of the application relates to a method of preventing a disease or disorder associated with the inhibition of one or more tropomyosin kinases (Trk). The method comprises administering to a patient in need of a treatment for diseases or disorders associated with modulation of a tropomyosin kinase an effective amount of a compound of Formula (IV), or a pharmaceutically acceptable salt, hydrate, solvate, prodrug, stereoisomer, or tautomer thereof.

Another aspect of the application is directed to a method of inhibiting a tropomyosin kinase (Trk). The method involves administering to a patient in need thereof an effective amount of a compound of Formula (IV), or a pharmaceutically acceptable salt, hydrate, solvate, prodrug, stereoisomer, or tautomer thereof.

Another aspect of the application is directed to a method of inhibiting one or more tropomyosin kinases (Trk), The method involves administering to a patient in need thereof an effective amount of a compound of Formula (IV), or a pharmaceutically acceptable salt, hydrate, solvate, prodrug, stereoisomer, or tautomer thereof.

Another aspect of the application is directed to pharmaceutical compositions comprising a compound of Formula (IV), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present application relates to a compound of Formula (IV), or a pharmaceutically acceptable salt, hydrate, solvate, prodrug, stereoisomer, or tautomer thereof, for use in a method of treating a disease associated with inhibiting a tropomyosin kinase (Trk).

Another aspect of the present application relates to a compound of Formula (IV), or a pharmaceutically acceptable salt, hydrate, solvate, prodrug, stereoisomer, or tautomer thereof, for use in a method of preventing a disease associated with inhibiting a tropomyosin kinase (Trk).

Another aspect of the present application relates to a compound of Formula (IV), or a pharmaceutically acceptable salt, hydrate, solvate, prodrug, stereoisomer, or tautomer thereof, for use in a method of treating a disease associated with inhibiting one or more tropomyosin kinases (Trk).

Another aspect of the present application relates to a compound of Formula (IV), or a pharmaceutically acceptable salt, hydrate, solvate, prodrug, stereoisomer, or tautomer thereof, for use in a method of preventing a disease associated with inhibiting one or more tropomyosin kinases (Trk).

Another aspect of the present application relates to the use of a compound of Formula (IV), or a pharmaceutically acceptable salt, hydrate, solvate, prodrug, stereoisomer, or tautomer thereof, in the manufacture of a medicament for treating a disease associated with inhibiting a tropomyosin kinase (Trk).

Another aspect of the present application relates to the use of a compound of Formula (IV), or a pharmaceutically acceptable salt, hydrate, solvate, prodrug, stereoisomer, or tautomer thereof, in the manufacture of a medicament for preventing a disease associated with inhibiting a tropomyosin kinase (Trk).

Another aspect of the present application relates to the use of a compound of Formula (IV), or a pharmaceutically acceptable salt, hydrate, solvate, prodrug, stereoisomer, or tautomer thereof, in the manufacture of a medicament for treating a disease associated with inhibiting one or more tropomyosin kinases (Trk).

Another aspect of the present application relates to the use of a compound of Formula (IV), or a pharmaceutically acceptable salt, hydrate, solvate, prodrug, stereoisomer, or tautomer thereof, in the manufacture of a medicament for preventing a disease associated with inhibiting one or more tropomyosin kinases (Trk).

Another aspect of the present application relates to a method of inhibiting of a Trk kinase. The method comprises administering to a subject in need thereof an effective amount of a compound of formula (IV), or a pharmaceutically acceptable salt thereof.

Another aspect of the present application relates to a method of inhibiting of one or more Trk kinases. The method comprises administering to a subject in need thereof an effective amount of a compound of formula (IV), or a pharmaceutically acceptable salt thereof.

Another aspect of the present application relates to a method of treating a disease or disorder associated with inhibiting of a Trk kinase. The method comprises administering to a subject in need thereof an effective amount of a compound of formula (IV), or a pharmaceutically acceptable salt thereof.

Another aspect of the present application relates to a method of treating a disease or disorder associated with inhibiting of one or more Trk kinases. The method comprises administering to a subject in need thereof an effective amount of a compound of formula (IV), or a pharmaceutically acceptable salt thereof.

Another aspect of the present application relates to a method of inhibiting a Trk kinase. The method comprises contacting the Trk kinase with an effective amount of a compound of formula (IV), or a pharmaceutically acceptable salt thereof.

Another aspect of the present application relates to a method of inhibiting a Trk kinase fusion. The method comprises contacting the Trk kinase fusion with an effective amount of a compound of formula (IV), or a pharmaceutically acceptable salt thereof.

Another aspect of the present application relates to a method of inhibiting a Trk kinase in a cell. The method comprises contacting the cell with an effective amount of a compound of formula (IV), or a pharmaceutically acceptable salt thereof.

Another aspect of the present application relates to a method of inhibiting a Trk kinase fusion in a cell. The method comprises contacting the cell with an effective amount of a compound of formula (IV), or a pharmaceutically acceptable salt thereof.

Another aspect of the present application relates to a method of inhibiting of a Trk kinase in a subject. The method comprises administering to the subject in need thereof an effective amount of a compound of formula (IV), or a pharmaceutically acceptable salt thereof.

Another aspect of the present application relates to a method of inhibiting of a Trk kinase fusion in a subject. The method comprises administering to the subject in need thereof an effective amount of a compound of formula (IV), or a pharmaceutically acceptable salt thereof.

Another aspect of the present application relates to a method of inhibiting one or more Trk kinases. The method comprises contacting the one or more Trk kinases with an effective amount of a compound of formula (IV), or a pharmaceutically acceptable salt thereof.

The present application further provides methods of treating a disease or disorder associated with modulation of one or more tropomyosin kinases (Trk) including, but not limited to, inflammatory diseases, infections, autoimmune disorders, stroke, ischemia, cardiac disorder, neurological disorders, dermatological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atopic dermatitis, pruritis, eczema, Gorlin Syndrome, Netherton Syndrome, basal cell carcinoma, dermatomyocytis, cylindromas, atherosclerosis, rheumatoid arthritis, osteoarthritis, heart failure, chronic pain, neuropathic pain, comprising, administering to a patient suffering from at least one of said diseases or disorder a compound of Formula (IV), or a pharmaceutically acceptable salt, hydrate, solvate, prodrug, stereoisomer, or tautomer thereof.

The present application provides inhibitors of one or more tropomyosin kinases (Trk) that are therapeutic agents in the treatment of diseases such as inflammation, autoimmune diseases, cancer and other diseases associated with the modulation of one or more tropomyosin kinases (Trk).

The present application further provides compounds and compositions with an improved efficacy and safety profile relative to known tropomyosin kinase (Trk) inhibitors. The present disclosure also provides agents with novel mechanisms of action toward tropomyosin kinases (Trk) in the treatment of various types of diseases including, but not limited to, inflammatory' diseases, infections, autoimmune disorders, stroke, ischemia, cardiac disorder, neurological disorders, dermatological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atopic dermatitis, pruritis, eczema, Gorlin Syndrome, Netherton Syndrome, basal ceil carcinoma, dermatomyocytis, cylindromas, atherosclerosis, rheumatoid arthritis, osteoarthritis, heart failure, chronic pain, and neuropathic pain. Ultimately the present application provides the medical community with a novel pharmacological strategy for the treatment of diseases and disorders associated with tropomyosin kinases (Trk).

DETAILED DESCRIPTION OF THE APPLICATION

The present application relates to compounds and compositions that are capable of inhibiting the activity' one or more tropomyosin kinases (Trk). The application features methods of treating, preventing or ameliorating a disease or disorder in which one or more tropomyosin kinases (Trk) play a role by administering to a patient in need thereof a therapeutically effective amount of a compound of Formula (IV), or a pharmaceutically acceptable salt, hydrate, solvate, prodrug, stereoisomer, or tautomer thereof. The methods of the present application can be used in the treatment of a variety' of tropomyosin kinases (Trk) dependent diseases and disorders by inhibiting the activity of one or more tropomyosin kinases (Trk). Inhibition of tropomyosin kinases (Trk) provides a novel approach to the treatment, prevention, or amelioration of diseases including, but not limited to, inflammatory' diseases, infections, autoimmune disorders, stroke, ischemia, cardiac disorder, neurological disorders, dermatological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atopic dermatitis, pruritis, eczema, Gorlin Syndrome, Netherton Syndrome, basal cell carcinoma, dermatomyocytis, cylindromas, atherosclerosis, rheumatoid arthritis, osteoarthritis, heart failure, chronic pain, neuropathic and pain.

The application further features methods of treating, preventing or ameliorating a disease or disorder in which one or more tropomyosin kinases (Trk) play a role by administering to a patient in need thereof a therapeutically effective amount of a compound of Formula (IV), or a pharmaceutically acceptable salt, hydrate, solvate, prodrug, stereoisomer, or tautomer thereof.

In a first aspect of the application, the compounds of Formula (IV) are described:

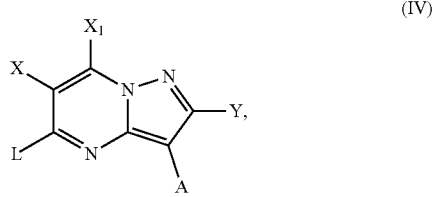

(IV)

and pharmaceutically acceptable salts, hydrates, solvates, isotopes, prodrugs, stereoisomers, and tautomers thereof, wherein A, L, X, Xi, and Y are as described herein above.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety' (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —CQOH, —CH2CN, —O—(Ci-C6) alkyl, (Ci-C$_{&}$) alkyl, Ci alkoxy, (C]—C6)haloaikyl, Ci-Cehaloalkoxy, —O—(C?-C6) alkenyl, -0-(C$_2$-C$_6$) alkynyl, (C$_2$—Ce) alkenyl, (C—C6) alkynyl, —OH, -0P(O)(OH)$_2$, —OC(O)(Ci-Ce) alkyl, —C(O)(Ci-C6) alkyl, —OC(O)0(Ci-Ce) alkyl, —NH$_2$, -\H ((C$_1$—CV) alkyl), —N((Ci-Ce) alkyl); —NH((C$_1$-C$_6$) alkyl, —C(0)NH(CI—C6) alkyl, —S(0)$_2$(Ci-Ce) alkyl, —S(O)NH (CI—C6) alkyl, and S(O)N((CI—C6) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O-iCi-Ce) alkyl, (Ci-Ce) alkyl, —O—(C$_2$-C$_6$) alkenyl, -0-(C$_2$—Ce) alkynyl, (C2-C6) alkenyl, (C$_2$-C$_6$) alkynyl, —OH, —OP(0)(OH)$_2$, —OC(O)(Ci-C6) alkyl, —C(0)(Ci-C6) alkyl, —OC (O)O(Ci-Ce) alkyl, MH$_2$, NH((Ci-Ce) alkyl), N((Ci-Cfi) alkyl)$_2$, —S((»$_2$—(C$_1$-C$_6$) alkyl, —S(0)NH(Ci-C6) alkyl, and S(0)N((Ct-(¾ alkyl)?. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, ietrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, fund, thienyl, pyrrolyl, pyridyl, pyrazolyi, pyrimidinyl, imidazolyl, isoxazolyl, oxazolyl, oxadiazolyi, pyrazinyl, indolyl, thiophen-2-yl, qmnolyl, benzopyranyl, isothiazolyl, thiazolyl, thiadiazole, indazole, benzimidazolyl, thieno[3,2-b]thiophene, triazolyl, triazinyl, imidazo[1,2-b] pyrazolyl, furo[2,3-c]pyridinyl, imidazo[1,2-a]pyridinyl, indazolyl, pyrrolo]2,3-c]pyridinyl, pyrrolo[3,2-c]pyridinyl, pyrazolo[3,4-c]pyridinyJ, thieno[3,2-cjpyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, henzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[delisoquinolinyl, pyrido[4,3-b][1,6]naphthyridinyl, thieno [2,3-b]pyrazinyl, quinazolinyl, tetrazolo[1,5-a]pyridinyl, [1,2,4j triazolo[4,3 a]pyridinyl, isoindolyl, pyrrolo[2,3-b] pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-lX²-pyrroio[2,1-b]pyrimidine, dibenzojb,dj thiophene, pyridin-2-one, furo[3,2-cjpyridinyl, furo[2,3-c]pyndinyl, 1H-pyndo[3,4-b]1,4]thiazinyl, benzooxazolyl, benzoisoxazolyl, furo[2,3-b]pyridinyl, benzothiophenyl, 1,5-naphthyridinyl, furo[3,2-b]pyridine, [f,2,4jtriazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazoio[1,5-b][1,2]oxazinyl, 4,5,6,7-tetrahydropyrazolo]1,5-a]pyridinyl, thiazolo[5,4-d]thiazolyl, imidazoj 2,1-b][1,3,4]thiadiazolyl, thieno[2,3-b]pyrrolyl, 3H-indolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a (Ci-Ce) alkyl group include, but are not limited to, methyl, ethyl, propyl, butyl, pentyl, hexyl, isopropyl, isobutyl, sec-butyl, tert-butyl, isopentyl, neopentyl, and isohexyl.

100491 "Alkoxy" refers to a straight or branched chain saturated hydrocarbon containing 1-12 carbon atoms containing a terminal in the chain, i.e., -0(alkyl). Examples of alkoxy groups include, without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be un substituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a C1-C4 alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

The term "aminoalkyl" as used herein refers to an alkyl group, as defined herein, which is substituted one or more amino. Examples of aminoalkyl groups include, but are not limited to, ammomethyl, diaminomethyl, aminoethyl, 1,2-aminoethyT, etc.

"Cycloalkyl" means monocyclic or polycyclic saturated carbon rings (e.g., fused, bridged, or spiro rings) containing 3-18 carbon atoms (e.g., C3-C10). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octeny 1.

"Heterocyclyl" or "heterocycloalkyl" means monocyclic or polycyclic rings (e.g., fused, bridged, or spiro rings) containing carbon and heteroatoms taken from oxygen, nitrogen, or sulfur and wherein there is not delocalized it electrons (aromaticity) shared among the ring carbon or heteroatoms. The heterocycloalkyl can be a 3-, 4-, 5-, 6-, 7-, 8-, 9-10-, 11-, or 12-membered ring. The heterocycloalkyl ring structure may be substituted by one or more substituents. The substituents can themselves be optionally substituted. Examples of heterocyclyl rings include, but are not limited to, oxetanyl, azetadinyi, tetrahydrofuranyl, tetrahydropyranyl, pyrrolidinyl, oxazolinyl, oxazolidinyl, thiazolinyl, thiazolidinyl, pyranyl, thiopyranyl, tctrahydropyranyl, dioxalinyl, piperidinyl, morpholinyl, thiomorpholinyl, thiomorpholinyl S-oxide, thiomorpholinyl S-dioxide, piperazmyl, azepinyl, oxepinyl, diazepinyl, tropanyl, oxazolidinonyl, and homotropanyl. In accordance with the present application, 3- to 10-membered heterocyclyl refers to saturated or partially saturated non aromatic rings structures containing between 3 and 10 atoms in which there is at least one heteroatoms selected from the group N, O, or S.

The term "hydroxyalkyl" means an alkyl group as defined above, where the alkyl group is substituted with one or more —OH groups. Examples of hydroxyalkyl groups include HO—CH2—, HO—CH2-CH2—and $CH_3$—(CHOH)—.

The term "haloalkyl" as used herein refers to an alkyl group, as defined herein, which is substituted one or more halogen. Examples of haloalkyl groups include, but are not limited to, trifluoromethyl, difluoromethyl, pentaf!uoroethyl, trich!orornethy!, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromeihoxy, etc.

The term "cyano" as used herein means a substituent having a carbon atom joined to a nitrogen atom by a triple bond, i.e., C≡N.

The term "amine" as used herein refers to primarily (R—NH2, R≠H), secondary (R2-NH, R2≠H) and tertiary' (R3-N, R≠H) amines. A substituted amine is intended to mean an amine where at least one of the hydrogen atoms has been replaced by the substituent.

The term "amino" as used herein means a substituent containing at least one nitrogen atom. Specifically, NH2, —NH(alkyl) or alkylamino, —N(alkyl)$_2$ or dialkylamino, amide-, carbamide-, urea, and sulfamide substituents are included in the term "amino".

The term "dialkylamino" as used herein refers to an amino or $NH_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethyiamino (i.e., —NCCFL-)?.), diethylamino, dipropylamino, diiso-propylamino, di-n-butylamino, di-sec-butylamino, di-tert-butylamino, methyl(ethyl)amino, methyl(butylamino), etc.

The term "oxo" as used herein refers to an=0 group.

"Spirocycloalkyl" or "spirocyclyr means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocyele can be fused to another ring carbocyclic, heterocyclic, aromatic, or heteroaromatic ring. One or more of the carbon atoms in the spirocyele can be substituted with a heteroatom (e.g., O, N, S, or P). A (C3-C12) spirocycloalkyl is a spirocyele containing between 3 and 12 carbon atoms. One or more of the carbon atoms can be substituted with a heteroatom.

The term "spiroheterocycloalkyl" or "spiroheterocyclyl" is understood to mean a spirocyele wherein at least one of the rings is a heterocycle (e.g., at least one of the rings is furany!, morpholiny!, or piperadinyl).

The term "solvate" refers to a complex of variable stoichiometry formed by a solute and solvent. Such solvents for the purpose of the application may not interfere with the biological activity' of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (IV) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenes ulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, poly gal acturonate, propionate, p-toluenes ulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "earner", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The term "gene fusion" refers to a chimeric genomic DNA, a chimeric messenger RNA, a truncated protein or a chimeric protein resulting from the fusion of at least a portion of a first gene to at least a portion of a second gene. In some embodiments, gene fusions involve internal deletions of genomic DNA within a single gene (e.g., no second gene is involved in the fusion). The gene fusion need not include entire genes or exons of genes.

The term "fusion protein" as used herein refers to a novel chimeric protein construct that is the result of combining two or more domains or linker regions from different proteins for the purpose of combining in one single polypeptide chain functions and recognition properties normally associated with two or more distinct polypeptides. This is most often accomplished by the adjacent molecular cloning of the nucleotide sequences encoding for the desired protein domains to result in the creation of a new polynucleotide sequence that codes for the desired protein. Alternatively, creation of a fusion protein may be accomplished by chemically joining two proteins together. For example, the fusion protein can comprise a Trk kinase (e.g., Trk A, TrkB, or TrkC) linked to another protein.

The term "cancer" includes, but is not limited to, the following cancers: adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary' central nervous system lymphoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ ceil tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macrog!obu!inemia, malignant mesothelioma, malignant thymoma, medulloblastoma, melanoma, intraocular melanoma, merkel cell carcinoma, metastatic squamous neck cancer with occult primary', multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e,g., renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodennal and pineal tumors, cutaneous t-cell lymphoma, testicular cancer, malignant thymoma, thyroid cancer, mammary' analogue secretory carcinoma (MASC), lung adenocarcinoma, intralymphatic cholangiocarcinoma, papillary thyroid cancer, pediatric glioma, sarcoma, glioblastoma, spitzoid neoplasms, astrocytoma, head and neck squamous cell carcinoma, low grade glioma, high grade glioma, congenital meroblastic nephroma, adenoid cystic carcinoma, cylindromas, gestational trophoblastic tumor, urethral cancer, uterine sarcoma, vaginal cancer, vulvar cancer, and Whims' tumor. In a preferred embodiment, the cancer is anon-small cell lung cancer.

In any of the embodiments of the application, the cancer can be any cancer in any organ. For example, the cancer can be selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

The present application relates to compounds or pharmaceutically acceptable salts, hydrates, solvates, prodrugs, stereoisomers, or tautomers thereof, capable of inhibiting one or more Trk kinases, which are useful for the treatment of diseases and disorders associated with modulation of one or more Trk kinases. The application further relates to compounds, or pharmaceutically acceptable salts, hydrates, solvates, prodrugs, stereoisomers, or tautomers thereof, which are useful for inhibiting one or more Trk kinases.

In one embodiment, the compounds of Formula (IV) have the structure of formula (V):

(V)

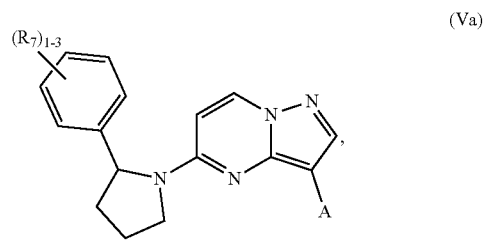

and pharmaceutically acceptable salts, hydrates, solvates, isotopes, prodrugs, stereoisomers, and tautomers thereof.

In another embodiment, the compounds of Formula (IV) have the structure of Formula (Va):

(Va)

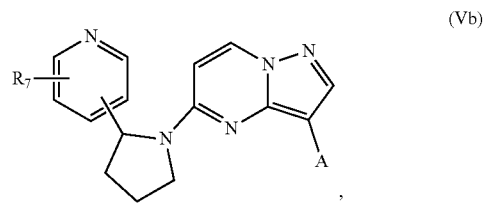

and pharmaceutically acceptable salts, hydrates, solvates, isotopes, prodrugs, stereoisomers, and tautomers thereof.

In another embodiment, the compounds of Formula (IV) have the structure of Formula (Vb):

(Vb)

and pharmaceutically acceptable salts, hydrates, solvates, isotopes, prodrugs, stereoisomers, and tautomers thereof.

In another embodiment, the compounds of Formula (TV) have the structure of Formula (Vc):

(Vc)

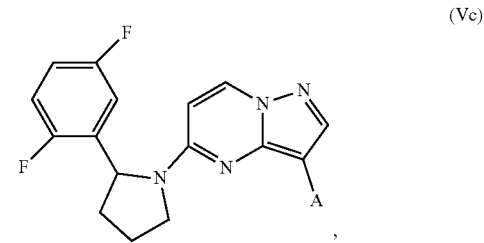

and pharmaceutically acceptable salts, hydrates, solvates, isotopes, prodrugs, stereoisomers, and tautomers thereof.

In another embodiment, the compounds of Formula (IV) have the structure of Formula (Vd):

(Vd)

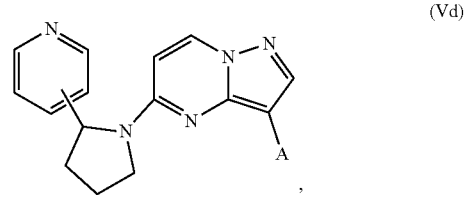

and pharmaceutically acceptable salts, hydrates, solvates, isotopes, prodrugs, stereoisomers, and tautomers thereof.

In another embodiment, the compounds of Formula (IV) have the structure of Formula (Ve) or (Vi):

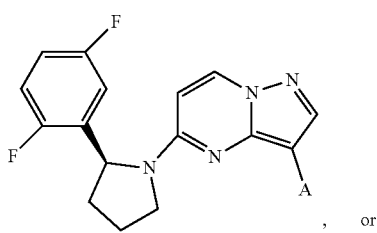

, or

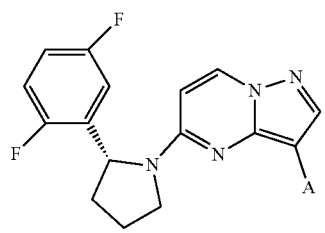

and pharmaceutically acceptable salts, hydrates, solvates, isotopes, prodrugs, stereoisomers, and tautomers thereof.

In another embodiment, the compounds of Formula (TV) have the structure of Formula (Via) or (VIb):

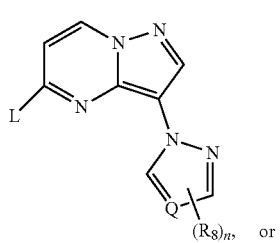

, or

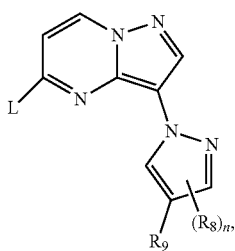

and pharmaceutically acceptable salts, hydrates, solvates, isotopes, prodrugs, stereoisomers, and tautomers thereof.

In another embodiment, the compounds of Formula (IV) have the structure of Formula (Vic):

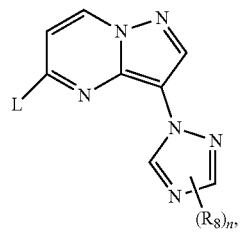

and pharmaceutically acceptable salts, hydrates, solvates, isotopes, prodrugs, stereoisomers, and tautomers thereof.

In another embodiment, the compounds of Formula (IV) have the structure of Formula (Vila) or (V11b):

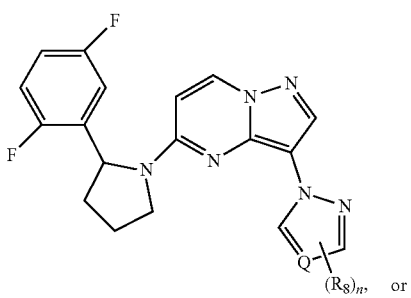

, or

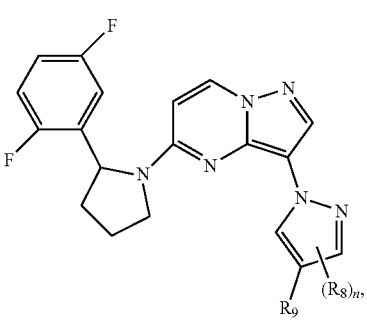

and pharmaceutically acceptable salts, hydrates, solvates, isotopes, prodrugs, stereoisomers, and tautomers thereof.

In another embodiment, the compounds of Formula (IV) have the structure of Formula (Vile):

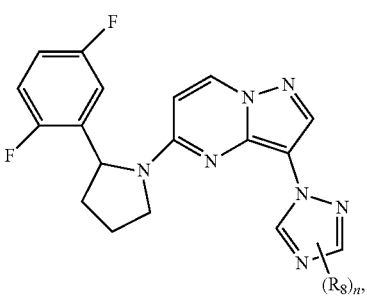

and pharmaceutically acceptable salts, hydrates, solvates, isotopes, prodrugs, stereoisomers, and tautomers thereof.

In another embodiment, the compounds of Formula (IV) have the structure of Formula (VIIIa):

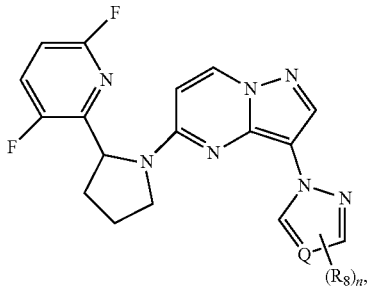

(VIIIa)

and pharmaceutically acceptable salts, hydrates, solvates, isotopes, prodrugs, stereoisomers, and tautomers thereof.

In another embodiment, the compounds of Formula (IV) have the structure of Formula (VIIIb):

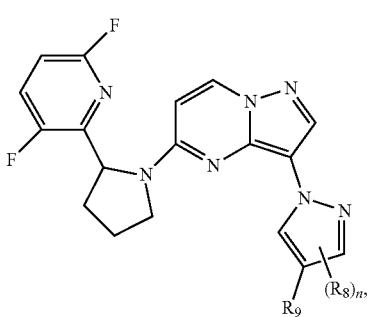

(VIIIb)

and pharmaceutically acceptable salts, hydrates, solvates, isotopes, prodrugs, stereoisomers, and tautomers thereof.

In another embodiment, the compounds of Formula (IV) have the structure of Formula (VIIIc):

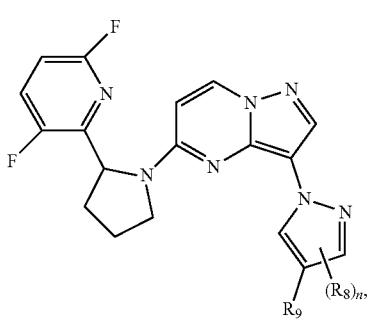

(VIIIc)

and pharmaceutically acceptable salts, hydrates, solvates, isotopes, prodrugs, stereoisomers, and tautomers thereof.

In some embodiments of the Formulae above, X is H, (C1-C2) alkyl, or halogen. In another embodiment, X is H, methyl, ethyl, F, or Cl. In yet another embodiment, X is H, methyl, or F. In another embodiment, X is fluoro. In another embodiment, X is H.

In some embodiments of the Formulae above, $X_1$ is D In another embodiment, $X_1$ methyl, or CN. In another embodiment, Y is H.

In some embodiments of the Formulae above, L is

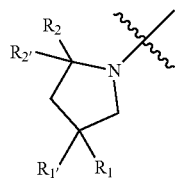

In another embodiment, L is —O (CR;R4MC$_6$-C$_{10}$—) aryl, —NR5-(CR3R$_4$)—(C6-CIO) aryl, —O(CR3R0-5- or 6-membered heteroaryl, or —NR5-(CR3R$_4$)-5- or 6-membered heteroaryl, wherein the aryl and heteroaryl are optionally substituted with one to three Rr. In another embodiment, L is -0(CR3R4)—(C6-CIO) aryl or —O(CRiRi)-5- or 6-membered heteroaryl, wherein the aryl and heteroaryl are optionally substituted with one to three Re. In another embodiment, L is —NR5-(CR3R4MC6-C10) aryl or —NRj-(CR3R$_4$)-5- or 6-membered heteroaryl, wherein the aryl and heteroaryl are optionally substituted with one to three Re. In another embodiment, L is —-0 (CR3R4)-(C6-Cio) aryl or —NR5-(CR3R$_4$)-(C6-Cio) and, wherein the aryl is optionally substituted with one to three $R^6$. In another embodiment, L is —O(CR3R0-5- or 6-membered heteroaryl, or —NR5-(CR3R4)-5- or 6-membered heteroaryl, wherein the heteroaryl is optionally substituted with one to three Re.

In some embodiments of the Formulae above, Ri is H, (C1-C3) alkyl, (C1-C3) alkoxy, (C1-C3) haloalkyl, (C1-C3) haloalkoxy, halogen, or —OH. In another embodiment, Ri is H, (C1-C3) alkyl, —OH, or halogen. In another embodiment, R—, is H, —OH, or halogen. In another embodiment, Ri is H, —OH, F, or Cl. In another embodiment, Ri is H, —OH, or F. In another embodiment, Ri is H.

In some embodiments of the Formulae above, Rr is H, (CI—C3) alkyl, (CI—C3) alkoxy, (C1-C3) haloalkyl, (CJ—CS) haloalkoxy, halogen, or —OH. In another embodiment, Rr is H, (C1-C3) alkyl, —OH, or halogen. In another embodiment, $R_1$, is H, —OH, or halogen. In another embodiment, Rids H, —OH, F, or Cl. In another embodiment, R, is H, —OH, or F. In another embodiment, Rr is H.

In some embodiments of the Formulae above, R2 is (Cfi-Cio) aryl optionally substituted with one to three R?. In another embodiment, R2 is 5- or 6-membered heteroaryl optionally substituted with one to three R?. In another embodiment, R2 is (Ce-Cio) aryl substituted with one to three R?. In another embodiment, R?. is 5- or 6-membered heteroaryl substituted with one to three R?. In another embodiment, R? is phenyl optionally substituted with one to three R?. In another embodiment, $R_2$ is phenyl substituted with one to three R?. In another embodiment, R?. is pyridine optionally substituted with one to three R?. In another embodiment, R2 is pyridine substituted with one to three R?.

In some embodiments of the Formulae above, $R_2$, is H, D, (CI—C$_3$) alkyl, or halogen. In another embodiment, R?' is H, (C1-C2) alkyl, or halogen. In another embodiment, R?' is H or halogen. In another embodiment, $R_2$r is H or (C1-C2) alkyl. In another embodiment, R2' is H.

In some embodiments of the Formulae above, R3 is H or (C1-C3) alkyl. In another embodiment, $R_3$ is H, methyl, or ethyl. In another embodiment, R; is H or methyl. In another embodiment, R3 is H. In another embodiment, R3 is methyl.

In some embodiments of the Formulae above, Rr is H or (C1-C3) alkyl. In another embodiment, Rr is H, methyl, or ethyl. In another embodiment, R4 is H or methyl. In another embodiment, $R_4$ is H. In another embodiment, R4 is methyl.

In some embodiments of the Formulae above, Rs is H or (C1-C3) alkyl. In another embodiment, Rs is H, methyl, or ethyl. In another embodiment, Rs is H or methyl. In another embodiment, Rs is H. In another embodiment, R s is methyl.

In some embodiments of the Formulae above, each Re is independently at each occurrence (C1-C3) alkyl, (C1-C3) alkoxy, ($C_1$-$C_3$) haloalkyl, (C1-C3) haloaikoxy, or halogen. In another embodiment, each Rs is independently at each occurrence (C1-C3) alkyl, (C1-C3) haloalkyl, or halogen. In another embodiment, each Re is independently at each occurrence (C1-C3) alkyl or halogen. In another embodiment, each Rs is independently at each occurrence methyl, ethyl, F, or Cl. In another embodiment, each Re is independently at each occurrence F or Cl.

In some embodiments of the Formulae above, each R, is independently at each occurrence (C1-C3) alkyl, (C1-C3) alkoxy, (C1-C3) haloalkyl, (C1-C3) haloaikoxy, or halogen. In another embodiment, each $R_7$ is independently at each occurrence (C1-C3) alkyl, (C1-C3) haloalkyl, or halogen. In another embodiment, each R7 is independently at each occurrence (C1-C3) alkyl or halogen. In another embodiment, each R? is independently at each occurrence methyl, ethyl, F, or Cl. In another embodiment, each R? is independently at each occurrence F or Cl.

In some embodiments of the Formulae above, A is

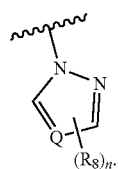

In some embodiments of the Formulae above, Q is C. In another embodiment, Q is N.

In some embodiments of the Formulae above, $R^g$, at each occurrence, is H, halogen, cyano, (Co—C6)alkyl-$QR^3$, (Co—C6)alkyl-$NR^aR^b$, (Co—C6)alkyl-$C(O)R^a$, (Co—C6) alkyl-$P(O)R^aR^b$, (Co—C6)aikyl-$S(0)pR^a$, $NR^cC(0)R^a$, NR—$S(0)_2R^b$, or $R^w$, and $R^w$ is (Ci-Ce) alkyl, (Ci-Cb) haloalkyl, (C3-C5) cycloalkyl, 3- to 8-membered heterocloalkyl, (Ce-Cio) and, or 5 to 10-membered heteroaryl, each of which is optionally substituted with one or more $R^{S2}$.

In some embodiments of the Formuale above, $R^8$ is (Co-Crdalkyl-$OR^a$.

In some embodiments of the Formulae above, $R^8$ is

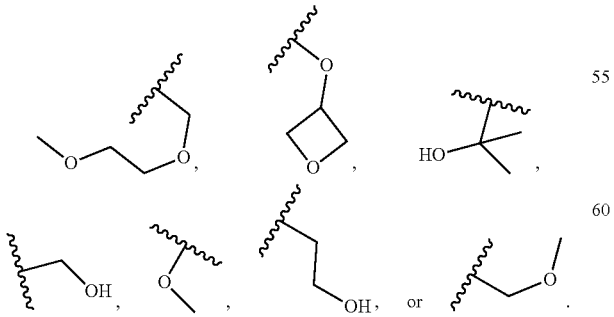

In some embodiments of the Formuale above, $II^8$ is (Co—C6)alkyd-$NR^aR^b$.

In some embodiments of the Formuale above, $R^8$ is

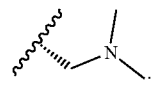

In some embodiments of the Formuale above, $R^8$ is (Co—C6)alkyl-$C(0)R^a$.

In some embodiments of the Formuale above, $R^8$ is

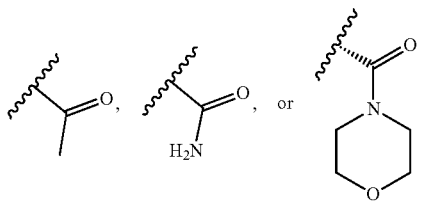

In some embodiments of the Formuale above, $R^8$ is (Co—C6)alkyl-$P(0)R^aR^b$.

In some embodiments of the Formuale above, $R^8$ is or

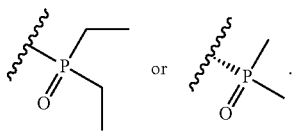

In some embodiments of the Formuale above, $R^8$ is (Co—C6)alkyl-$S(0)pR^a$.

In some embodiments of the Formuale above, $R^8$ is

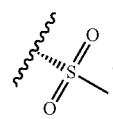

In some embodiments of the Formuale above, $R^8$ is $NR^eC(Q)R^a$.

In some embodiments of the Formuale above, $R^8$ is

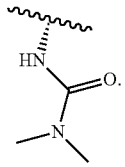

In some embodiments of the Formuale above, $R^8$ is $NR^e(0)2R^a$.

In some embodiments of the Formuale above, R⁸ is

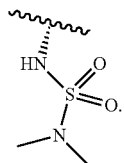

In some embodiments of the Formuale above, R^w is (C₁—C5) alkyl optionally substituted with one or more R^S2. In some embodiments of the Formuale above, R^w is (C1-C3) alkyl optionally substituted with one or more R^S2. In some embodiments of the Formuale above, R^W is methyl.

In some embodiments of the Formuale above, R^Q is (C₁-C₆) haloalkyl optionally substituted with one or more R^S2. In some embodiments of the Formuale above, R^W is (C1-C3) haloalkyl optionally substituted with one or more R^S2.

In some embodiments of the Formulae above, R^w is trifluoromethyl or difluoromethyl.

In some embodiments of the Formuale above, R^3/4 is (C₃-C₈) cycloalkyl optionally substituted with one or more R^S2. In some embodiments of the Formuale above, R^W is (C4-Cfi) cycloalkyl optionally substituted with one or more R^S2.

In some embodiments of the Formuale above, R^w is 3- to 8-membered heterocycloalkyl, optionally substituted with one or more R^S2. In some embodiments of the Formuale above, R^W is 4- to 6-membered heterocycloalkyl, optionally substituted with one or more R^S2.

In some embodiments of the Formuale above, R^W is tetrahydrofuranyl, pyrrolidinyl, tetrahydrofuranyl, dihydrofuranyl, tetrahydropyranyl, dihydropyranyl, or morpholinyl.

In some embodiments of the Formuale above, R^W is

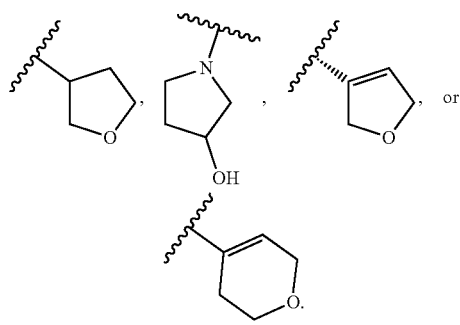

In some embodiments of the Formuale above, R^W is (Ce-Cio) aryl optionally substituted with one or more R^S2.

In some embodiments of the Formuale above, R^W is 5 to 10-membered heieroaryl optionally substituted with one or more R^S2. In some embodiments of the Formuale above, R^Q is 5-membered heteroaryl optionally substituted with one or more R^S2. In some embodiments of the Formuale above, R^W is 6-membered heteroaryl optionally substituted with one or more R^S2.

In some embodiments of the Formuale above, R^3/4 is pyridyl, pyrazinyl, pyrimidinyl, pyridazinyl, thiophenyl, furanyl, oxadiazolyl, pyrazo!yl, pyrrolyl, pyridinonyl, thiazolyl, imidazolyl, oxazolyl, or isoxazolyi.

In some embodiments of the Formuale above, R^W is

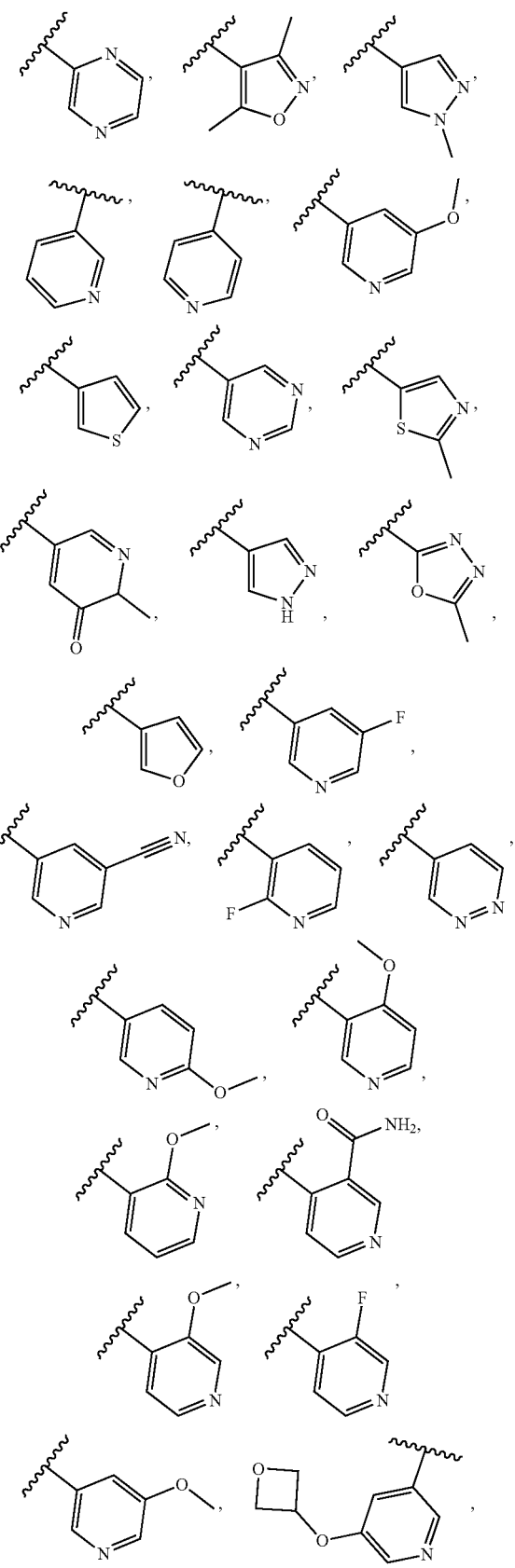

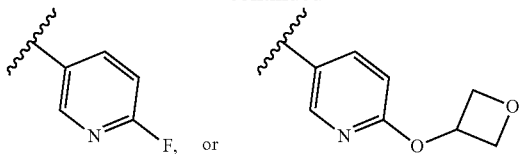

In some embodiments of the Formulae above, R9, at each occurrence, is H, halogen, cyano, (Co-CeJalky!-OR$^a$, (Co—C6)alkyl-NR$^a$R$^b$, (Co—Ce)alkyl-C(0)R$^a$, (Co—C$_6$)alkyl-P (O)R$^a$R$^b$, (Co—C6)alkyl-S(0)pR$^a$, NR$^e$C(0)R$^a$, NR$^2$S(0)$_2$ R$^a$, or R$^w$, and R$^W$ is is (Ci-Ce) alkyl, (Ci-Ce) haloalkyl, (C$_3$—Cs) cycloalkyl, 3- to 8-membered heterocycloalkyl, (Ce-Cio) aiyl, or 5 to 10-membered heteroaryl, each of which is optionally substituted with one or more R·

In some embodiments of the Formuale above, R9 is R$^w$ and R$^w$ is (Ci-Ce) alkyl, (C1-C6) haloalkyl, (Cs—C—) cycloalkyl, 3- to 8-membered heterocycloalkyl, (Ce-Cio) aryl, or 5 to 10-membered heteroaryl, each of which is optionally substituted with one or more R$^{S2}$.

In some embodiments of the Formulae above, Q is N and Rs is is H, halogen, cyano, (Co—C6)aJkyl-OR$^a$, (Co—C6) aJkyl-NR$^a$R$^b$, (Co—C6)alkyl-C(O)R$^a$, (Co—C6)alkyl-P(O) R$^a$R$^b$, (Co—C6)alky1-S(0)pR$^a$, NR$^e$C(0)R$^a$, NR$^e$S(0)$_2$R$^a$, or R$^W$.

In some embodiments of the Formulae above, Q is C, Rs is is H, halogen, cyano, (Co—C$_6$)alkyl-OR$^a$, (Co—C6) alkyl-NR$^a$R$^b$, (Co—C6)alkyl-C(0)R$^a$, (Co—C6)alkyl-P(O) R$^a$R$^b$, (Co—C$_6$)alkyl-S(0)pR$^a$, NR—C(O)R$^a$, NR$^e$S(0)2R$^a$, or R$^w$, and R9 is H, halogen, cyano, (Co—C6>alkyl-OR$^a$, (Co—C6)alkyl-NR$^a$R$^b$, (Co—C6)alkyl-C(0)R$^a$, (Co—C6) alkyl-P(0)R$^a$R$^b$, (Co-C$^6$dalkyl-S(0)$_p$R$^a$, NR$^e$C(O)R$^a$, NR$_e$S (O)$_2$R$^a$. or R$^q$.

In some embodiments of the Formulae above, Rs and Rs, together with the atoms to which they are attached, form a 5-membered ring optionally comprising one or more heteroatoms selected from N, O, and S and optionally substituted with one or more R$^{S1}$. In another embodiment, Rs and R9, together with the atoms to which they are attached, form a 6-membered ring optionally comprising one or more heteroatoms selected from N, O, and S and optionally substituted with one or more R$^{S1}$. In another embodiment, Rs and R9, together with the atoms to which they are attached, form a 7-membered ring optionally comprising one or more heteroatoms selected from N, O, and S and optionally substituted with one or more R$^{S1}$.

In some embodiments of the Formulae above, R$^{S1}$, at each occurrence, is H, halogen, cyano, (Ci-C&) alkyl, (C$_1$-C$_6$) haloalkyl, (Co—C3)alkyl-OR$^c$, (Co—C3)alkyl-NR$_c$R$^d$, C(0)OR$^c$, or C(0)NR$^c$R$^d$.

In some embodiments of the Formulae above, R$^{S2}$, at each occurrence, is H, halogen, cyano, (Ci-Ce) alkyl, (Ci-Ce) haloalkyl, (Co—C3)alkyl-OR$^c$, (Co—C3)alkyl-NR$^c$R$^d$, C(0)OR$^e$, or C(O)NR$^c$R$^d$.

In some embodiments of the Formulae above, R$^a$ is R$^i$, (C3-Cc) cycloalkyl, 3- to 8-membered heterocycloalkyl, (Co—C3)alkyl-OR$^g$, or (Co—C3)alkyl-NR$^g$NR$^h$.

In some embodiments of the Formulae above, R$^b$ is R$^i$ (Cs—Cs) cycloalkyl, 3- to 8-membered heterocycloalkyl, (Co—C3)alkyl-OR$^g$, or (Co—C3)alkyl-NR$^g$NR$^h$.

In some embodiments of the Formulae above, R$^c$ is R$^i$, (Cs—Cs) cycloalkyl, 3- to 8-membered heterocycloalkyl, (Co-Csjalkyl-OR$^8$, or (Co-Cslalkyl-NRsNR$^h$.

In some embodiments of the Formulae above, R$^d$ is R$^1$, (Cs—Cs) cycloalkyl, 3- to 8-membered heterocycloalkyl, (Co—C3)alkyl-OR$^8$, or (Co—C3)a!ky!-NR$^g$NR$^h$.

In some embodiments of the Formulae above, R$^a$ and R$^b$ together with the atoms to which they are attached form a 5 to 7-membered ring optionally comprising one or more heteroatoms selected from N, O, and S. In some embodiments of the Formulae above, R$^a$ and R$^b$ together with the atoms to which they are attached form a 5-membered ring optionally comprising one or more heteroatoms selected from N, O, and S. In some embodiments of the Formulae above, R$^a$ and R$^b$ together with the atoms to which they are attached form a 6-membered ring optionally comprising one or more heteroatoms selected from N, O, and S.

In some embodiments of the Formulae above, R$^e$ and R$^d$ together with the atoms to which they are attached form a 5 to 7-membered ring optionally comprising one or more heteroatoms selected from N, O, and S. In some embodiments of the Formulae above, R$^c$ and R$^d$ together with the atoms to which they are attached form a 5-membered ring optionally comprising one or more heteroatoms selected from N, O, and S. In some embodiments of the Formulae above, R$^c$ and R$^d$ together with the atoms to which they are attached form a 6-membered ring optionally comprising one or more heteroatoms selected from N, O, and S.

In some embodiments of the Formulae above, R$^e$ is H, (Ci-Ce) alkyl or (Co—Ce) haloalkyl.

in some embodiments of the Formulae above, R$^g$ is H, (C1-C0) alkyl or (Ci-Ce) haloalkyl.

In some embodiments of the Formulae above, R$^h$ is H, (Ci-Ce) alkyl or (Ci-Ce) haloalkyl.

In some embodiments of the Formulae above, R$^I$ is H, (Ch-Ce) alkyl or (Ch—Ce) haloalkyl.

in some embodiments of the Formulae above, R$^J$ is H, (Ci-Ce) alkyl or (Ci-Ce) haloalkyl.

In some embodiments of the Formulae above, n is 0. In another embodiment, n is 1. In another embodiment, n is 2. In another embodiment, n is 0, 1, or 2. In another embodiment, n is 1, 2, or 3. In another embodiment, n is 0 or 1. In another embodiment, n is 1 or 2.

In some embodiments of the Formulae above, p is 0. In another embodiment, p is 1. In another embodiment, p is 2. In another embodiment, p is 0 or 1. In another embodiment, p is 1 or 2.

In some embodiments of the Formulae above, X is H, F, or methyl. In another embodiment, X is H. In another embodiment, X is F.

In some embodiments of the Formulae above, Xi is H. In another embodiment, Xi is H and X is H or F. In another embodiment, Xi is H and X is H. In another embodiment, Xi is H and X is F.

In some embodiments of the Formulae above, A is

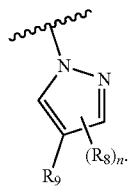

In some embodiments of the Formulae above, A is

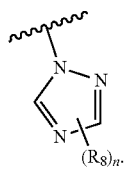

In some embodiments of the Formulae above, A is.

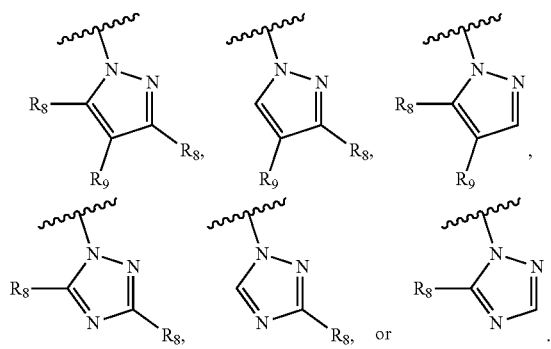

In another embodiment, Xi is H, X is H or F, and Y is H, (C1-C3) alkyl or CN. In another embodiment, $X_1$ is H, X is H or F, Y is H, $(C_1-C_3)$ alkyl or CN, and L is

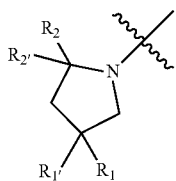

In another embodiment, Xi is H, X is H or F, Y is H, $(C_1-C_3)$ alkyl or CN, L is

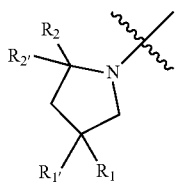

and R? is H. In another embodiment, Xi is H, X is H or F, Y is H, (C1-C3) alkyl or CN, L is

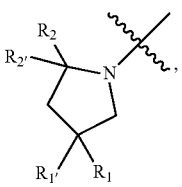

$R_{2'}$ is H, and R2 is phenyl or pyridinyl optionally substituted with one to three $R_7$.

In another embodiment, Xi is H, X is H or F, Y is H, (C1-C3) alkyl or CN, L is

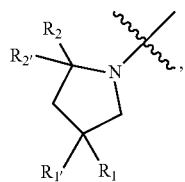

R?.' is H, and R2 is phenyl optionally substituted with one to three R—. In another embodiment, $X_1$ is H, X is H or F, Y is H, $(C_1-C_3)$ alkyl or CN, L is

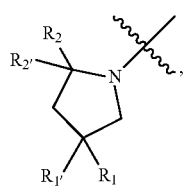

$R_{2'}$ is H, and R2 is pyridinyl optionally substituted with one to three R?.

In another embodiment, $X_1$ is H, X is H or F, Y is H, (C1-C3) alkyl or CN, L is

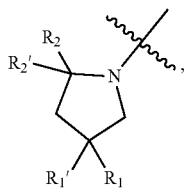

$R_{2'}$ is H, and $R_2$ is phenyl substituted with one to three R?. In another embodiment, $X_1$ is H, X is H or F, Y is H, $(C_1-C_3)$ alkyl or CN, L is

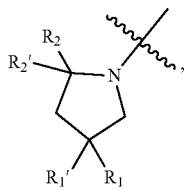

$R_{2'}$ is H, and $R_2$ is pyridinyl substituted with one to three R?.

In another embodiment, Xi is H, X is H or F, and Y is H. In another embodiment, $X_1$ is H, X is H or F, Y is H, and L is

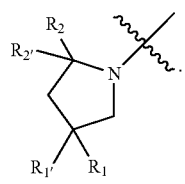

In another embodiment, Xi is H, X is H or F, and Y is H. In another embodiment, Xi is H. X is H or F, Y is H, L is

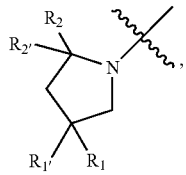

and R2' is H. In another embodiment, $X_{2'}$ is H, X is H or F, and Y is H. In another embodiment, Xi is H, X is H or F, Y is H, L is

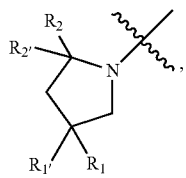

$R_{2'}$ is H, and R2 is phenyl or pyridmyl optionally substituted with one to three $R_7$.

In another embodiment $X_1$ is H, X is H1 or F, Y is H1, L is

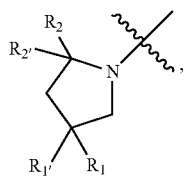

$R_{2'}$ is H and R2 is phenyl optionally substituted with one to three R?. In another embodiment, $X_2$ is H, X is H or F, Y is H, L is

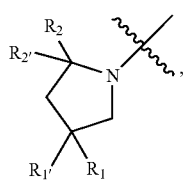

$R_{2'}$ is H, and $R_2$ is pyridinyl optionally substituted with one to three R?.

In another embodiment, $X_1$ is H, X is H or F, Y is H, L is

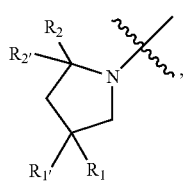

$R_{2'}$ is H, and R2 is phenyl substituted with one to three R?. In another embodiment, Xi is H, X is H or F, Y is H, L is

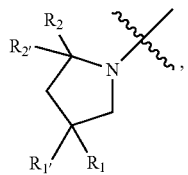

$R_{2'}$ is H, and $R_2$ is pyridinyl substituted with one to three $R_7$.

In another embodiment, Xi is H, X is H, and Y is H, (C1-C3) alkyl or CN. In another embodiment, $X_1$ is H, X is H, Y is H, $(C_1-C_3)$ alkyl or CN, and L is

In another embodiment, $X_1$ is H, X is H, Y is H, $(C_1-C_3)$ alkyl or CN, L is

and $R_{2'}$ is H. In another embodiment, $X_1$ is H, X is H, Y is H, $(C_1-C_3)$ alkyl or CN, L is

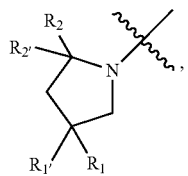

$R_{2'}$ is H, and R?. is phenyl or pyridmyl optionally substituted with one to three R7.

In another embodiment, Xi is H, X is H, Y is H, (C1-C3) alkyl or CN, L is

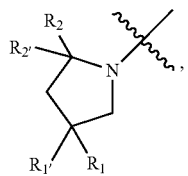

$R_{2'}$ is H and $R_2$ is phenyl optionally substituted with one to three R?. In another embodiment, $X_1$ is H, X is H, Y is H, $(C_1-C_3)$ alkyl or CN, L is

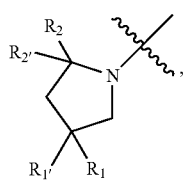

$R_{2'}$ is H, and $R_2$ is pyridmyl optionally substituted with one to three $R_7$.

In another embodiment, $X_1$ is H, X is H, Y is H, (C1-C3) alkyl or CN, L is

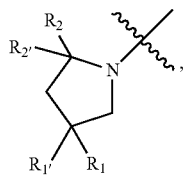

$R_{2'}$ is H, and $R_2$ is phenyl substituted with one to three $R_7$. In another embodiment, $X_1$ is H, X is H, Y is H, $(C_1-C_3)$ alkyl or CN, L is

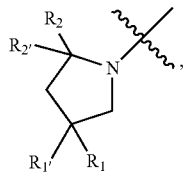

$R_{2'}$ is H, and $R_2$ is pyridinyl substituted with one to three $R_7$.

In another embodiment, $X_1$ is H, X is H, and Y is H. In another embodiment, $X_1$ is H, X is H, Y is H, and L is

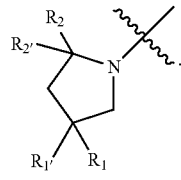

In another embodiment, $X_1$ is H, X is H, Y is H, L is

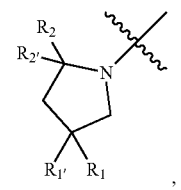

and $R_{2'}$ is H. In another embodiment, $X_1$ is H, X is H, Y is H, L is

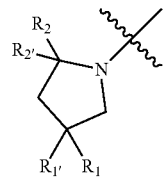

$R_{2'}$ is H, and $R_2$ is phenyl or pyridinyl optionally substituted with one to three $R_7$.

In another embodiment, $X_1$ is H, X is H, Y is H, L is

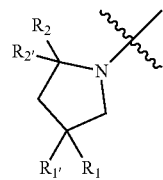

and $R_{2'}$ is H. In another embodiment, $X_1$ is H, X is H, Y is H, L is

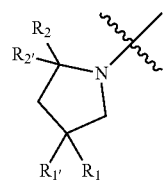

$R_{2'}$ is H, and $R_2$ is phenyl optionally substituted with one to three $R_7$. In another embodiment, $X_1$ is H, X is H, Y is H, L is

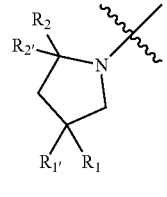

and $R_{2'}$ is H. In another embodiment, $X_1$ is H, X is H, Y is H, L is

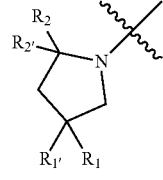

$R_{2'}$ is H, and $R_2$ is pyridinyl optionally substituted with one to three $R_7$.

In another embodiment, $X_1$ is H, X is H, Y is H, L is

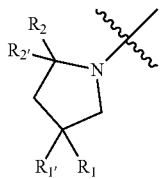

and $R_{2'}$ is H. In another embodiment, $X_1$ is H. X is H, Y is H, L is

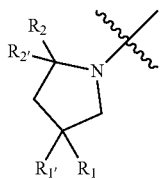

$R_{2'}$ is H and $R_2$ is phenyl substituted with one to three R?. In another embodiment Xi is H, X is H, Y is H, L is

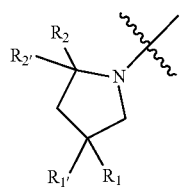

and $R_{2'}$ is H. In another embodiment, $X_1$ is H, X is H, Y is H, L is

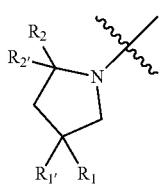

$R_{2'}$ is H, and R2 is pyridinyl substituted with one to three R?.

In another embodiment, $X_1$ is H, X is F, and Y is H, (C1-C3) alkyl or CN. In another embodiment, $X_1$ is H, X is F, Y is H, $(C_1\text{-}C_3)$ alkyl or CN, and L is

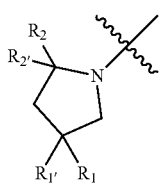

In another embodiment, $X_1$ is H, X is F, Y is H, $(C_1\text{-}C_3)$ alkyl or CN, L is

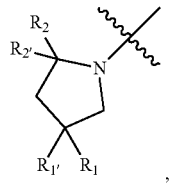

and $R_{2'}$ is H.

In another embodiment, Xi is H, X is F, Y is H, (C1-C3) alkyl or CN, L is

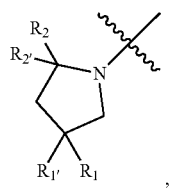

$R_{2'}$ is H, and $R_2$ is phenyl or pyridinyl optionally substituted with one to three $R_7$. In another embodiment, $X_1$ is H, X is F, Y is H, $(C_1\text{-}C_3)$ alkyl or CN, L is

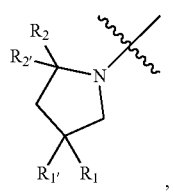

$R_{2'}$ is H, and $R_2$ is phenyl optionally substituted with one to three R?. In another embodiment, $X_1$ is H, X is F, Y is H, $(C_1\text{-}C_3)$ alkyl or CN, L is

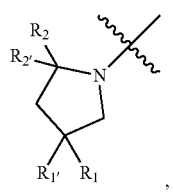

$R_{2'}$ is H, and $R_2$ is pyridinyl optionally substituted with one to three R?.

In another embodiment, $X_2$ is H, X is F, Y is H, (C1-C3) alkyl or CN, L is

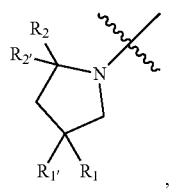

R2' is H, and R2 is phenyl substituted with one to three R?.

In another embodiment, $X_1$ is H, X is F, Y is H, ($C_1$-$C_3$) alkyl or CN, L is

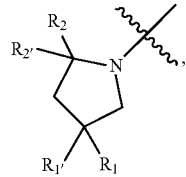

$R_{2'}$ is H, and $R_2$ is pyridinyl substituted with one to three R?.

In another embodiment, $X_1$ is H, X is F, and Y is H. In another embodiment, $X_1$ is H, X is F, Y is H, and L is

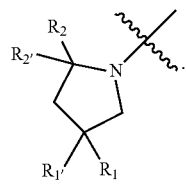

In another embodiment, Xi is H, X is F, Y is H, and L is

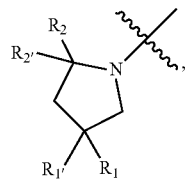

and $R_{2'}$ is H. In another embodiment, Xi is H, X is F, Y is H, and L is

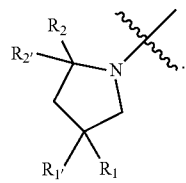

$R_{2'}$ is H, and $R_2$ is phenyl or pyridinyl optionally substituted with one to three s $R_7$.

In another embodiment, $X_1$ is H, X is F, Y is H, and L is

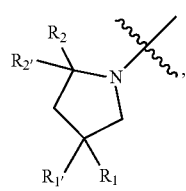

$R_{2'}$ is H, and R?. is phenyl optionally substituted with one to three R?. In another embodiment, Xi is H, X is F, Y is H, and L is

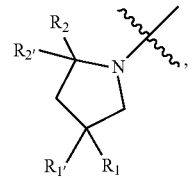

$R_{2'}$ is H, and $R_2$ is pyridinyl optionally substituted with one to three R?. In another embodiment, Xi is H, X is F, Y is H, and L is

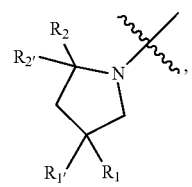

$R_{2'}$ is H, and R? is phenyl substituted with one to three R?. In another embodiment, $X_1$ is H, X is F, Y is H, L is

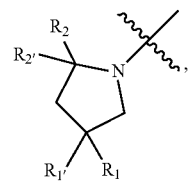

$R_{2'}$ is H, and $R_2$ is pyridinyl substituted with one to three R?.

In another embodiment, Xi is H, X is H or F, Y is H, and L is -0(CR3R4)-phenyl optionally substituted with one or more Re. In another embodiment, Xi is H, X is H or F, and Y is H. In another embodiment, Xi is H, X is H or F, Y is H, and L is -0(CR3R4)-pyridmyl optionally substituted with one or more Re. In another embodiment, Xi is H, X is H or F, and Y is H. In another embodiment, Xi is H, X is H or F, Y is H, and L is -0(CR3R4)-phenyl or —O(CR3RO-pyridi-nyl wherein the phenyl and pyridinyl are optionally substituted with one or more Kr, In another embodiment, Xi is H, X is H, Y is H, and L is -0(CR3R4)-phenyl optionally substituted with one or more Re. In another embodiment, Xi is H, X is H, and Y is H. In another embodiment, Xi is H, X is H, Y is H, and L is -0(CR3R4)-pyridinyl optionally substituted with one or more $II_6$. In another embodiment, Xi is H, X is H, and Y is H. In another embodiment, Xi is H, X is H, Y is H, and L is -0(CR3R4)-phenyl or -0(CR3R4)-pyridinyi wherein the phenyl and pyridinyl are optionally substituted with one or more Re.

In another embodiment, Xi is H, X is F, Y is H, and L is -0(CR3R4)-phenyl optionally substituted with one or more Re. In another embodiment, Xi is H, X is F, Y is H, and L is -0(CR3R4)-pyridinyl optionally substituted with one or more Re. In another embodiment, Xi is H, X is F, and Y is H. In another embodiment, Xi is H, X is F, Y is H, and L is -0(CR3R4)-phenyl or -0(CR3R4)-pyridinyl wherein the phenyl and pyridinyl are optionally substituted with one or more Re.

In another embodiment, Xi is H, X is H or F, Y is H, and L is —$NR_3$—(CR3$R_4$)-phenyl optionally substituted with one or more Re. In another embodiment, Xi is H, X is H or F, and Y is H. In another embodiment, Xi is H, X is H or F, Y is H, and L is —NR5-(CR3R4)-pyridinyl optionally substituted with one or more Re. In another embodiment, $X_1$ is H, X is H or F, and Y is H. In another embodiment, $X_1$ is H, X is H or F, Y is H, and L is —NRs-(CR3R4)-phenyl or —O(CR3R0-pyridinyl wherein the phenyl and pyridinyl are optionally substituted with one or more Re.

In another embodiment, Xi is H, X is H, Y is H, and L is —NR5—(CR3R4)-phenyl optionally substituted with one or more Re. In another embodiment, Xi is H, X is H, Y is H, and L is —NR5-(CR3R4)-pyridinyl optionally substituted with one or more Re. In another embodiment, Xi is H, X is H, and Y is H. In another embodiment, Xi is H, X is H, Y' is H, and L is —NR5-(CR3R4)-phenyl or -0(CR3R4)-pyridinyl wherein the phenyl and pyridinyl are optionally substituted with one or more Re.

In another embodiment, Xi is H, X is F, Y is H, and L is —NR8—(CR3R4)-phenyl optionally substituted with one or more Re. In another embodiment, Xi is H, X is F, and Y is H. In another embodiment, Xi is H, X is F, Y is H, and L is —NR5-(CR3R4)-pyridinyl optionally substituted with one or more Re. In another embodiment, Xi is H, X is F, and Y is H. In another embodiment, Xi is H, X is F, Y is H, and L is -NR5-(CR:<R4)-phenyl or —O(CR3R4)-pyridinyl wherein the phenyl and pyridinyl are optionally substituted with one or more $R_6$.

In another embodiment, Xi is H, X is F, and Y is ($C_1$-$C_3$) alkyl. In another embodiment, Xi is H, X is F, and Y is CN. In another embodiment, $X_1$ s H, X is H, and Y is (C1-C3) alkyl. In another embodiment, Xi is H, X is H, and Y is CN. In another embodiment, Xi is H, X is H or F, and Y is (Ci-Cs) alkyl. In another embodiment, Xi is H, X is H or F, and Y is CN.

Non-limiting illustrative compounds of the application include:

| Cmp No. | Structure |
|---|---|
| I-147 | |
| I-148 | |
| I-149 | 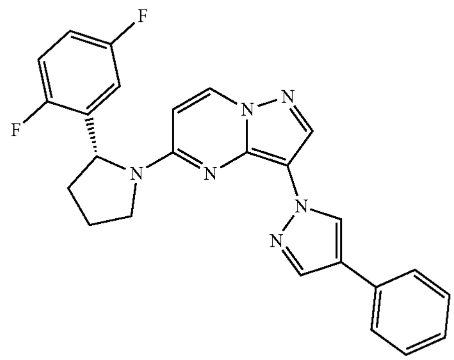 [SMILES: Fc1ccc(F)c([C@H]2CCCN2c2ccn3ncc(-n4cc(-c5ccccc5)cn4)c3n2)c1] |
| I-150 | 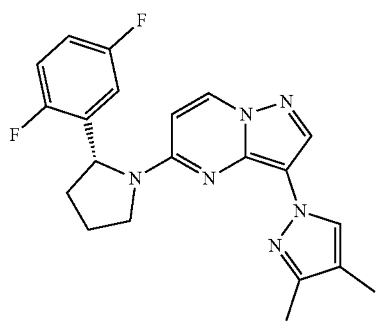 [SMILES: Cc1cn(-c2cnn3ccc(N4CCC[C@@H]4c4cc(F)ccc4F)nc23)nc1C] |
| I-151 | 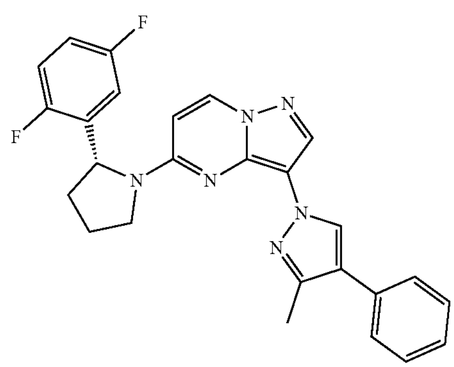 [SMILES: Cc1nn(-c2cnn3ccc(N4CCC[C@@H]4c4cc(F)ccc4F)nc23)cc1-c1ccccc1] |
| I-152 | 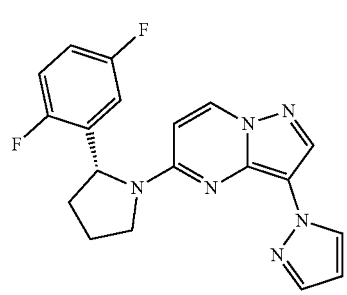 [SMILES: Fc1ccc(F)c([C@H]2CCCN2c2ccn3ncc(-n4cccn4)c3n2)c1] |

| Cmp No. | Structure |
|---|---|
| I-153 | 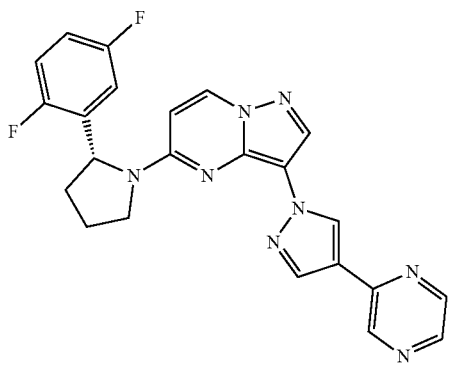 [SMILES: Fc1ccc(F)c([C@H]2CCCN2c2ccn3ncc(-n4cc(-c5cnccn5)cn4)c3n2)c1] |
| I-154 | 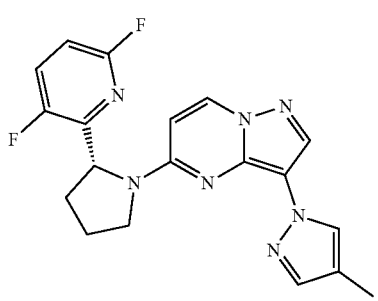 [SMILES: Cc1cnn(-c2cnn3ccc(N4CCC[C@@H]4c4nc(F)ccc4F)nc23)c1] |
| I-155 | 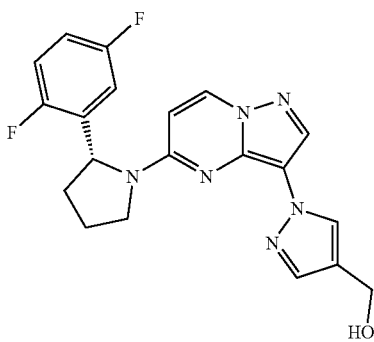 [SMILES: OCc1cnn(-c2cnn3ccc(N4CCC[C@@H]4c4cc(F)ccc4F)nc23)c1] |
| I-156 | 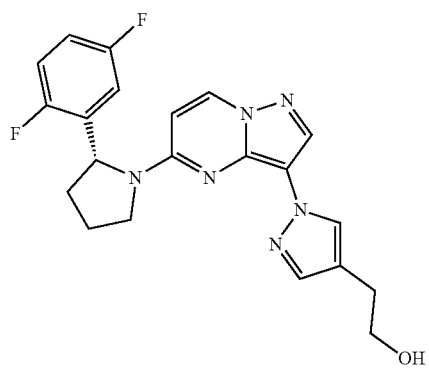 [SMILES: OCCc1cnn(-c2cnn3ccc(N4CCC[C@@H]4c4cc(F)ccc4F)nc23)c1] |
| Cmp No. | Structure |
|---|---|
| I-157 | 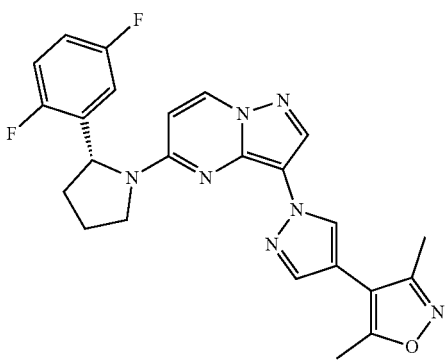 [SMILES: Cc1noc(C)c1-c1cnn(-c2cnn3ccc(N4CCC[C@@H]4c4cc(F)ccc4F)nc23)c1] |
| I-158 | 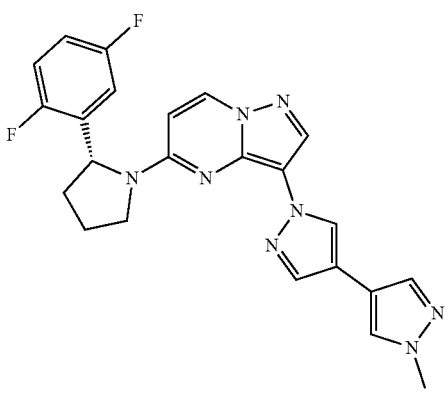 [SMILES: Cn1cc(-c2cnn(-c3cnn4ccc(N5CCC[C@@H]5c5cc(F)ccc5F)nc34)c2)cn1] |
| I-159 | 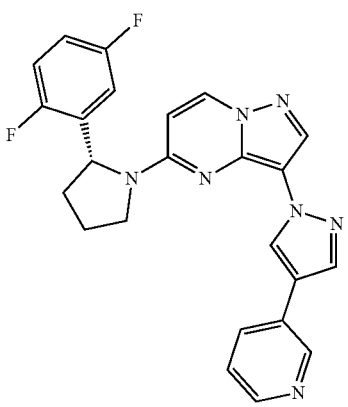 [SMILES: Fc1ccc(F)c([C@H]2CCCN2c2ccn3ncc(-n4cc(-c5cccnc5)cn4)c3n2)c1] |
| I-160 | 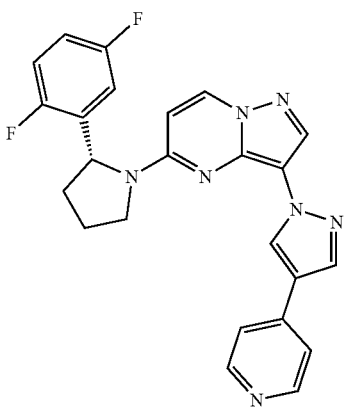 [SMILES: Fc1ccc(F)c([C@H]2CCCN2c2ccn3ncc(-n4cc(-c5ccncc5)cn4)c3n2)c1] |

| Cmp No. | Structure |
|---|---|
| I-161 | 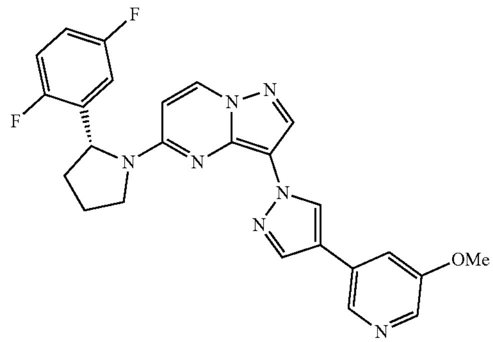 [SMILES: COc1cncc(-c2cnn(-c3cnn4ccc(N5CCC[C@@H]5c5cc(F)ccc5F)nc34)c2)c1] |
| I-162 | 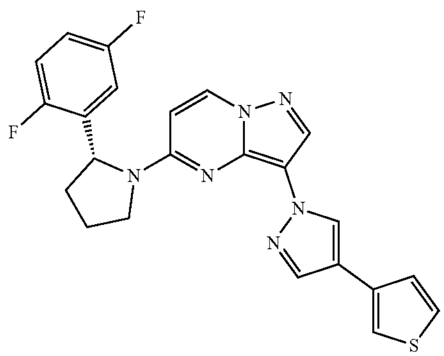 |
| I-163 | 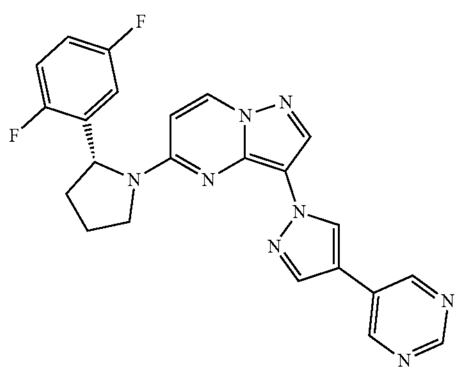 [SMILES: Fc1ccc(F)c([C@H]2CCCN2c2ccn3ncc(-n4cc(-c5cncnc5)cn4)c3n2)c1] |
| I-164 | 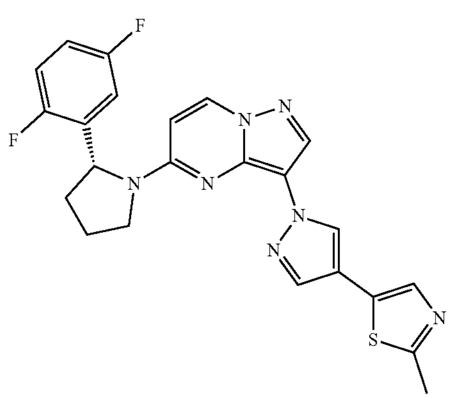 [SMILES: Cc1ncc(-c2cnn(-c3cnn4ccc(N5CCC[C@@H]5c5cc(F)ccc5F)nc34)c2)s1] |
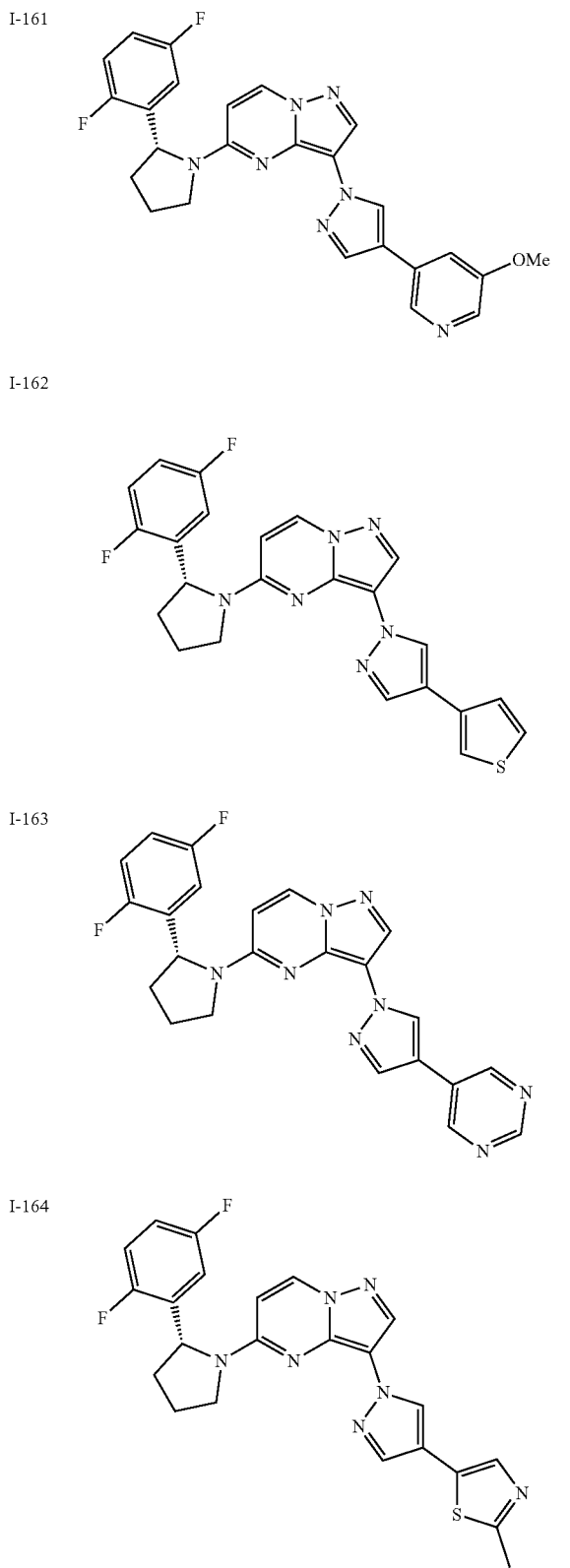
| Cmp No. | Structure |
|---|---|
| I-165 | 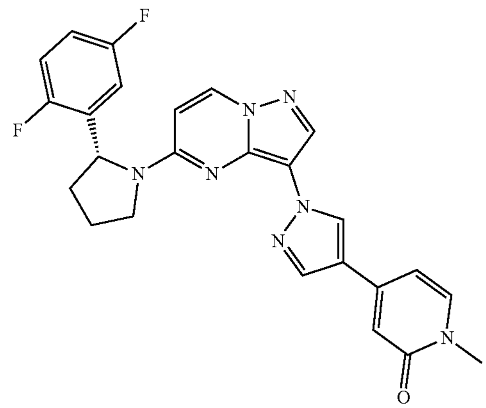 [SMILES: Cn1ccc(-c2cnn(-c3cnn4ccc(N5CCC[C@@H]5c5cc(F)ccc5F)nc34)c2)cc1=O] |
| I-166 | 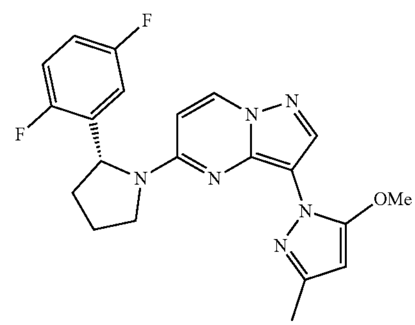 [SMILES: COc1cc(C)nn1-c1cnn2ccc(N3CCC[C@@H]3c3cc(F)ccc3F)nc12] |
| I-167 | 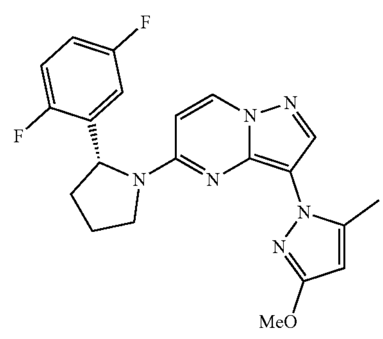 [SMILES: COc1cc(C)n(-c2cnn3ccc(N4CCC[C@@H]4c4cc(F)ccc4F)nc23)n1] |
| I-168 | 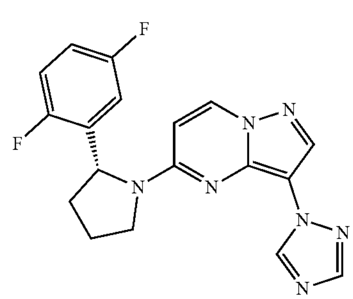 [SMILES: Fc1ccc(F)c([C@H]2CCCN2c2ccn3ncc(-n4cncn4)c3n2)c1] |
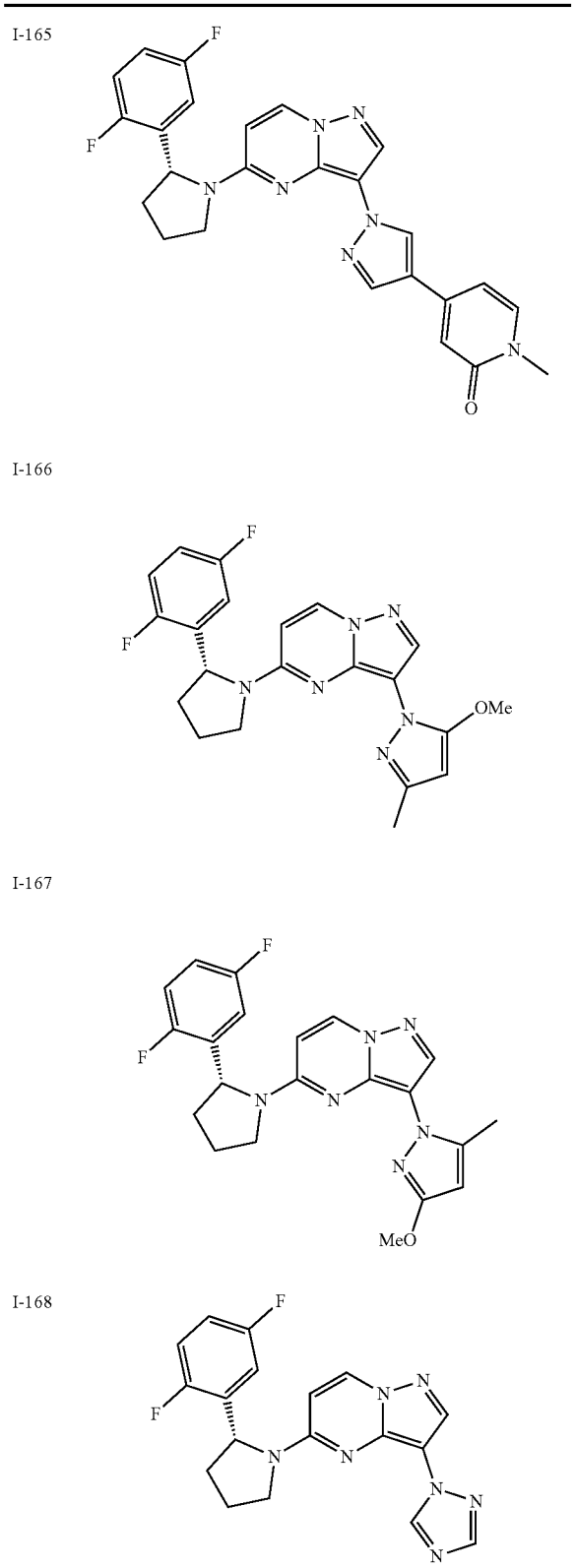

| Cmp No. | Structure |
|---|---|
| I-169 | 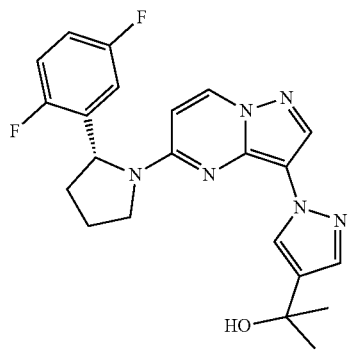 [SMILES: CC(C)(O)c1cnn(-c2cnn3ccc(N4CCC[C@@H]4c4cc(F)ccc4F)nc23)c1] |
| I-170 | 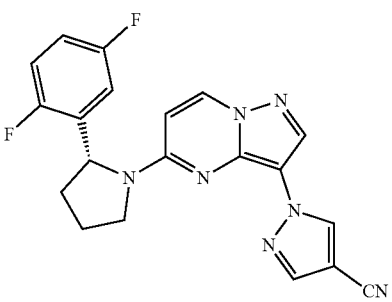 [SMILES: N#Cc1cnn(-c2cnn3ccc(N4CCC[C@@H]4c4cc(F)ccc4F)nc23)c1] |
| I-171 | 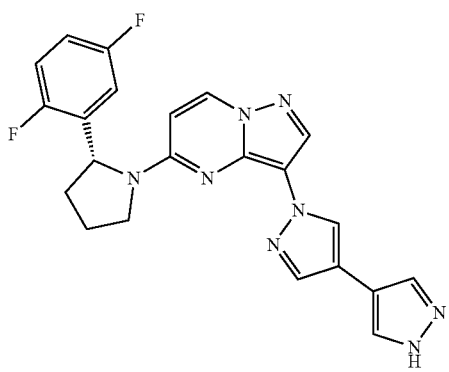 [SMILES: Fc1ccc(F)c([C@H]2CCCN2c2ccn3ncc(-n4cc(-c5cn[nH]c5)cn4)c3n2)c1] |
| I-172 | 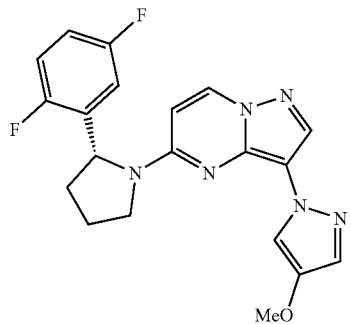 [SMILES: COc1cnn(-c2cnn3ccc(N4CCC[C@@H]4c4cc(F)ccc4F)nc23)c1] |
| I-173 | 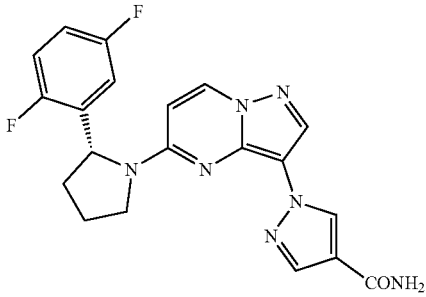 [SMILES: NC(=O)c1cnn(-c2cnn3ccc(N4CCC[C@@H]4c4cc(F)ccc4F)nc23)c1] |
| I-174 | 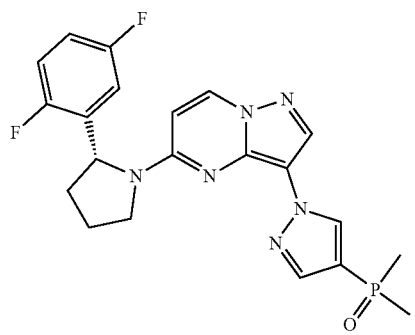 [SMILES: CP(C)(=O)c1cnn(-c2cnn3ccc(N4CCC[C@@H]4c4cc(F)ccc4F)nc23)c1] |
| I-175 | 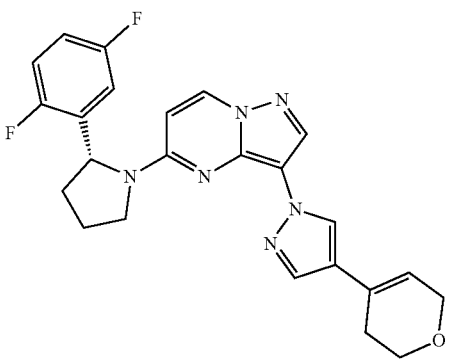 [SMILES: Fc1ccc(F)c([C@H]2CCCN2c2ccn3ncc(-n4cc(C5=CCOCC5)cn4)c3n2)c1] |
| I-176 | 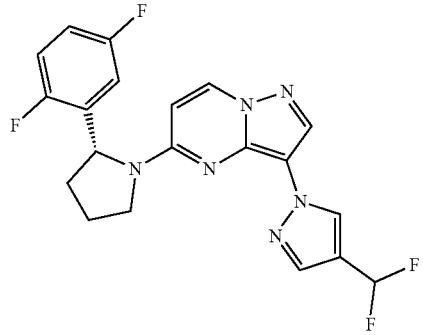 [SMILES: Fc1ccc(F)c([C@H]2CCCN2c2ccn3ncc(-n4cc(C(F)F)cn4)c3n2)c1] |

| Cmp No. | Structure |
|---|---|
| I-177 | 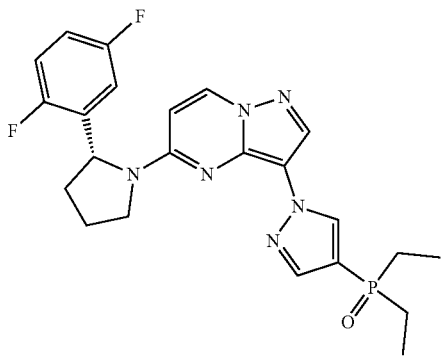 [SMILES: CCP(=O)(CC)c1cnn(-c2cnn3ccc(N4CCC[C@@H]4c4cc(F)ccc4F)nc23)c1] |
| I-178 | 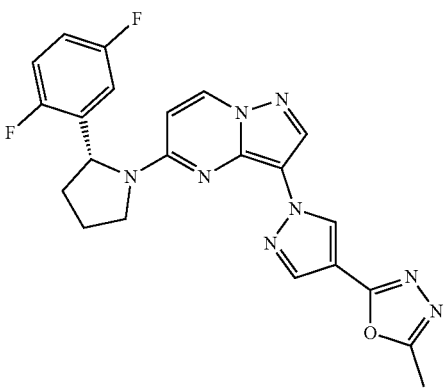 [SMILES: Cc1nnc(-c2cnn(-c3cnn4ccc(N5CCC[C@@H]5c5cc(F)ccc5F)nc34)c2)o1] |
| I-179 | 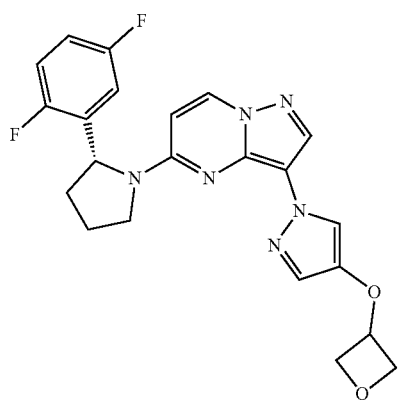 [SMILES: Fc1ccc(F)c([C@H]2CCCN2c2ccn3ncc(-n4cc(OC5COC5)cn4)c3n2)c1] |
| I-180 | 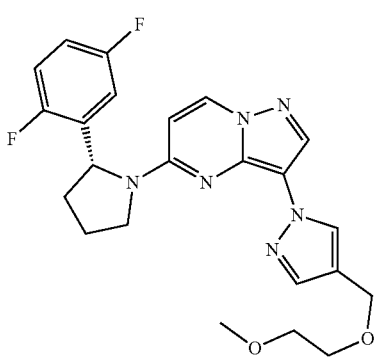 [SMILES: COCCOCc1cnn(-c2cnn3ccc(N4CCC[C@@H]4c4cc(F)ccc4F)nc23)c1] |
| Cmp No. | Structure |
|---|---|
| I-181 | 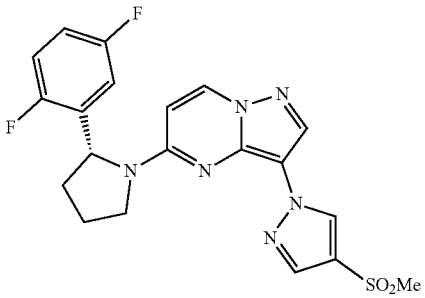 |
| I-182 | 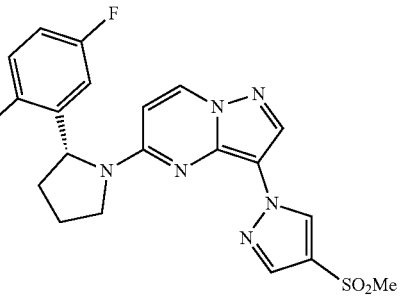 |
| I-183 | 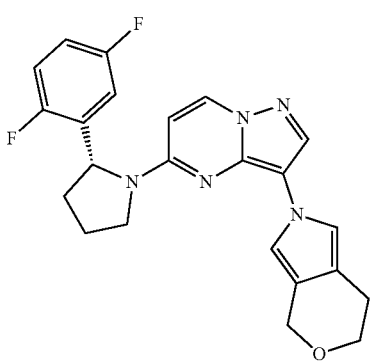 [SMILES: Fc1ccc(F)c([C@H]2CCCN2c2ccn3ncc(-n4cc5c(c4)COCC5)c3n2)c1] |
| I-184 | 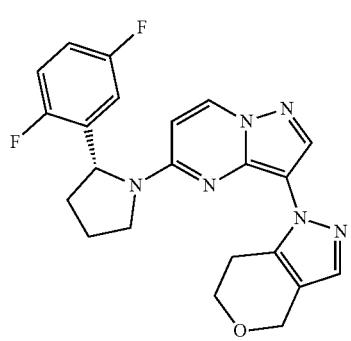 [SMILES: Fc1ccc(F)c([C@H]2CCCN2c2ccn3ncc(-n4ncc5c4CCOC5)c3n2)c1] |

| Cmp No. | Structure |
|---|---|
| I-185 | 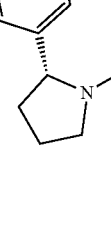 |
| I-186 | |
| I-187 | |
| I-188 | |
| Cmp No. | Structure |
|---|---|
| I-189 | 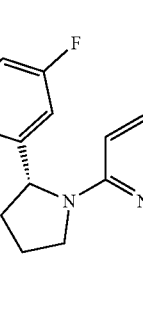 |
| I-190 | |
| I-191 | |
| I-192 | |

-continued
| Cmp No. | Structure |
|---|---|
| I-193 | 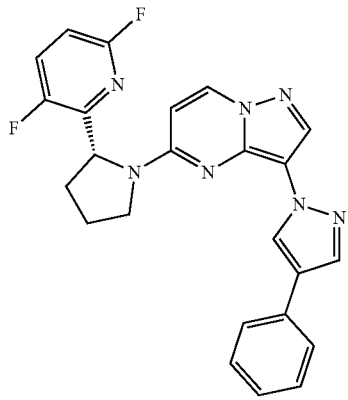 [SMILES: Fc1ccc(F)c([C@H]2CCCN2c2ccn3ncc(-n4cc(-c5ccccc5)cn4)c3n2)n1] |
| I-194 | 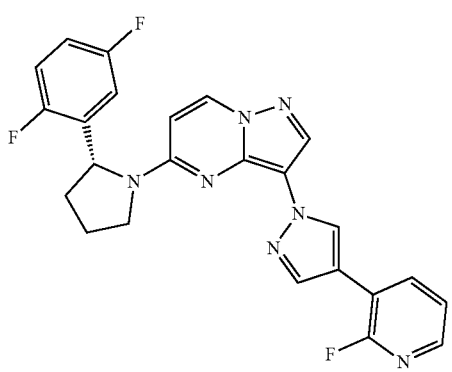 [SMILES: Fc1ccc(F)c([C@H]2CCCN2c2ccn3ncc(-n4cc(-c5cccnc5F)cn4)c3n2)c1] |
| I-195 | 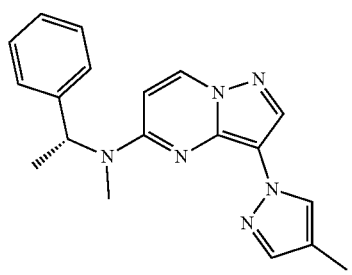 [SMILES: Cc1cnn(-c2cnn3ccc(N(C)[C@H](C)c4ccccc4)nc23)c1] |
| I-196 | 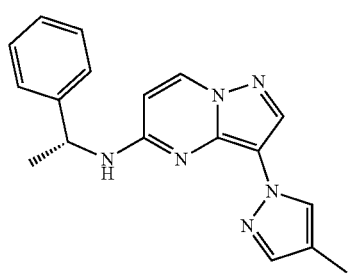 [SMILES: Cc1cnn(-c2cnn3ccc(N[C@H](C)c4ccccc4)nc23)c1] |
-continued
| Cmp No. | Structure |
|---|---|
| I-197 | 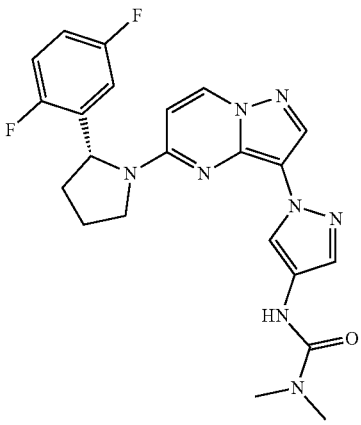 [SMILES: CN(C)C(=O)Nc1cnn(-c2cnn3ccc(N4CCC[C@@H]4c4cc(F)ccc4F)nc23)c1] |
| I-198 | 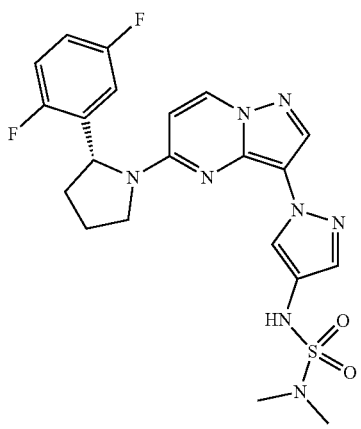 |
| I-199 | 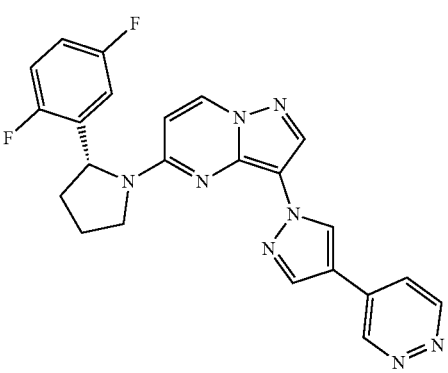 [SMILES: Fc1ccc(F)c([C@H]2CCCN2c2ccn3ncc(-n4cc(-c5ccnnc5)cn4)c3n2)c1] |
| I-200 | 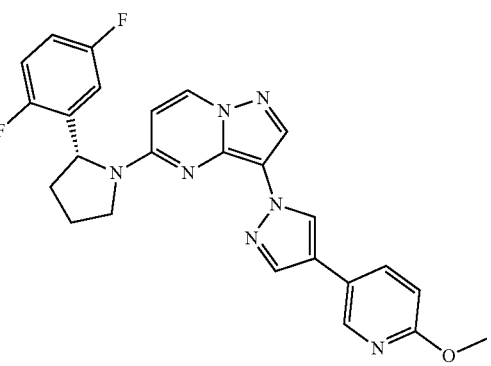 |

-continued
| Cmp No. | Structure |
|---|---|
| I-201 | 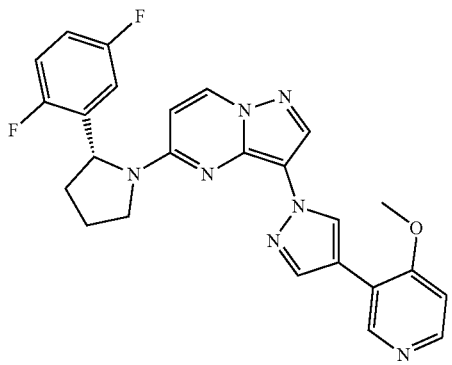 [SMILES: COc1ccncc1-c1cnn(-c2cnn3ccc(N4CCC[C@@H]4c4cc(F)ccc4F)nc23)c1] |
| I-202 | 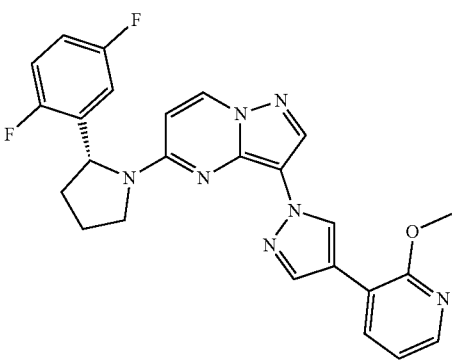 [SMILES: COc1ncccc1-c1cnn(-c2cnn3ccc(N4CCC[C@@H]4c4cc(F)ccc4F)nc23)c1] |
| I-203 | 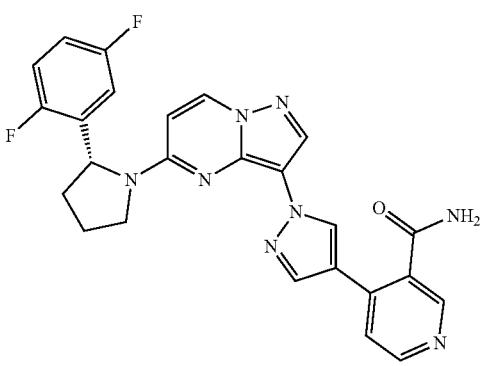 [SMILES: NC(=O)c1cnccc1-c1cnn(-c2cnn3ccc(N4CCC[C@@H]4c4cc(F)ccc4F)nc23)c1] |
| I-204 | 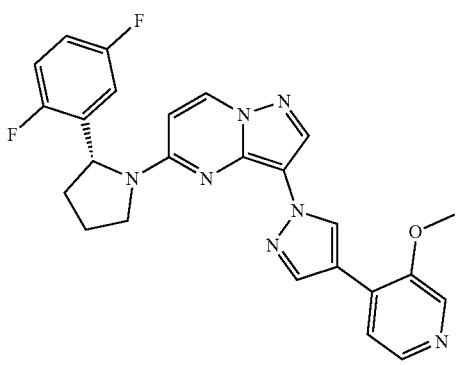 [SMILES: COc1cnccc1-c1cnn(-c2cnn3ccc(N4CCC[C@@H]4c4cc(F)ccc4F)nc23)c1] |
-continued
| Cmp No. | Structure |
|---|---|
| I-205 | 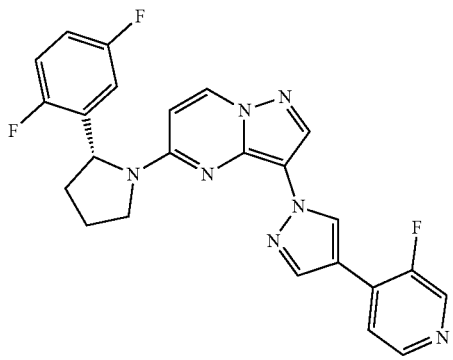 [SMILES: Fc1ccc(F)c([C@H]2CCCN2c2ccn3ncc(-n4cc(-c5ccncc5F)cn4)c3n2)c1] |
| I-206 | 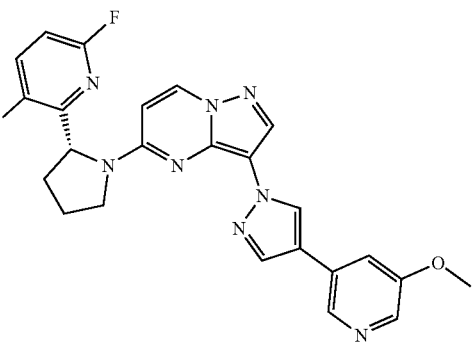 |
| I-207 | 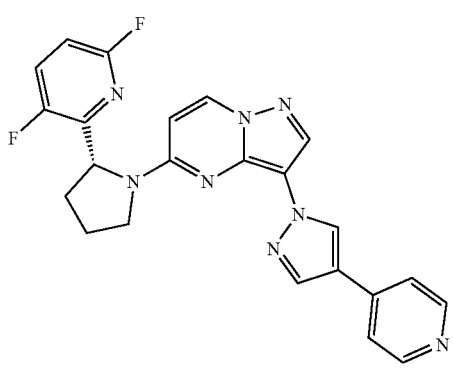 [SMILES: Fc1ccc(F)c([C@H]2CCCN2c2ccn3ncc(-n4cc(-c5ccncc5)cn4)c3n2)n1] |
| I-208 | 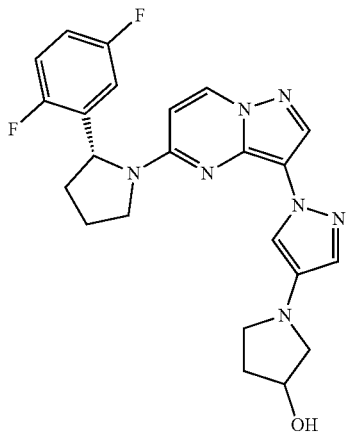 |

| Cmp No. | Structure |
|---|---|
| I-209 | 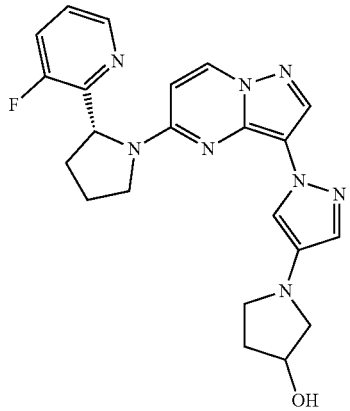 [SMILES: OC1CCN(c2cnn(-c3cnn4ccc(N5CCC[C@@H]5c5ncccc5F)nc34)c2)C1] |
| I-210 | 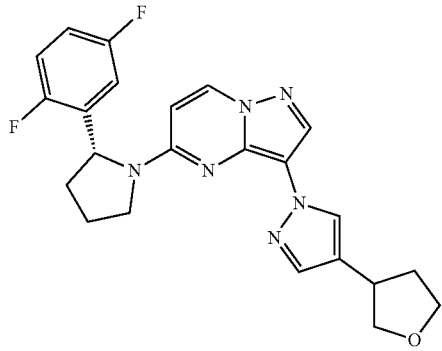 [SMILES: Fc1ccc(F)c([C@H]2CCCN2c2ccn3ncc(-n4cc(C5CCOC5)cn4)c3n2)c1] |
| I-211 | 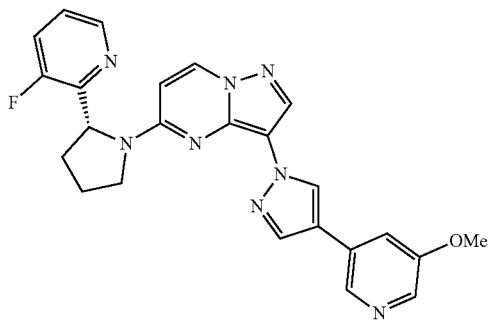 [SMILES: COc1cncc(-c2cnn(-c3cnn4ccc(N5CCC[C@@H]5c5ncccc5F)nc34)c2)c1] |
| I-212 | 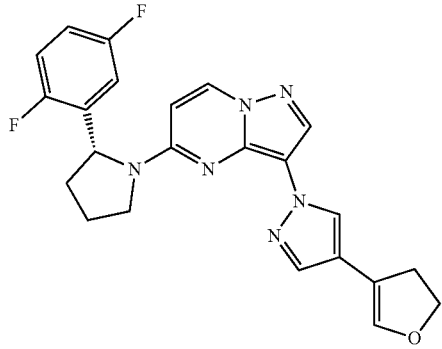 [SMILES: Fc1ccc(F)c([C@H]2CCCN2c2ccn3ncc(-n4cc(C5=COCC5)cn4)c3n2)c1] |
| I-213 | 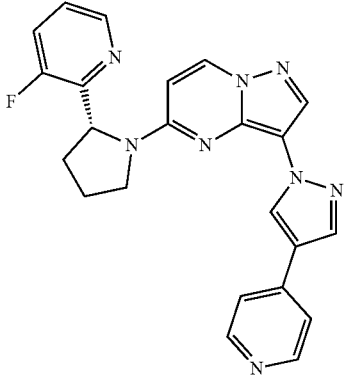 [SMILES: Fc1cccnc1[C@H]1CCCN1c1ccn2ncc(-n3cc(-c4ccncc4)cn3)c2n1] |
| I-214 | 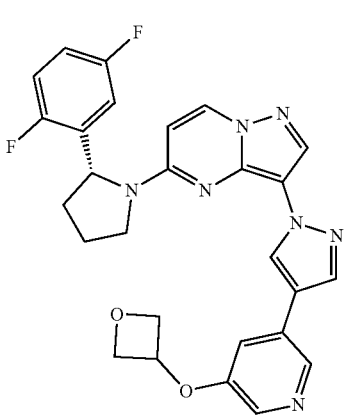 |
| I-215 | 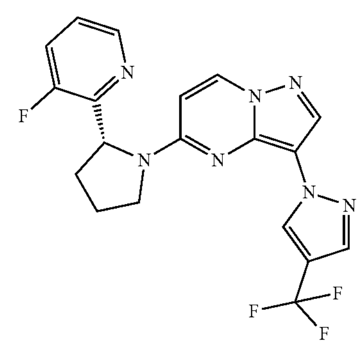 [SMILES: Fc1cccnc1[C@H]1CCCN1c1ccn2ncc(-n3cc(C(F)(F)F)cn3)c2n1] |
| I-216 | 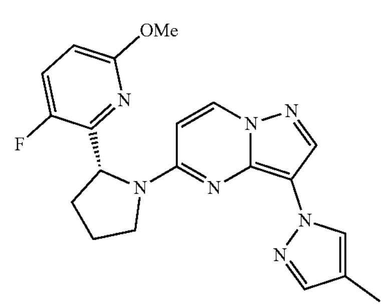 [SMILES: COc1ccc(F)c([C@H]2CCCN2c2ccn3ncc(-n4cc(C)cn4)c3n2)n1] |

| Cmp No. | Structure |
|---|---|
| I-217 | 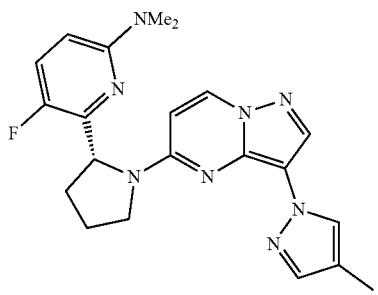 |
| I-218 | 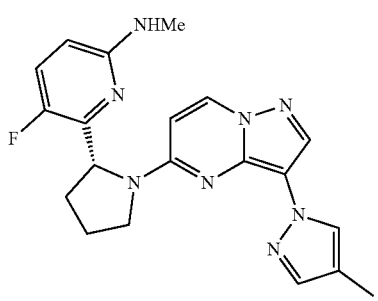 [SMILES: CNc1ccc(F)c([C@H]2CCCN2c2ccn3ncc(-n4cc(C)cn4)c3n2)n1] |
| I-219 | 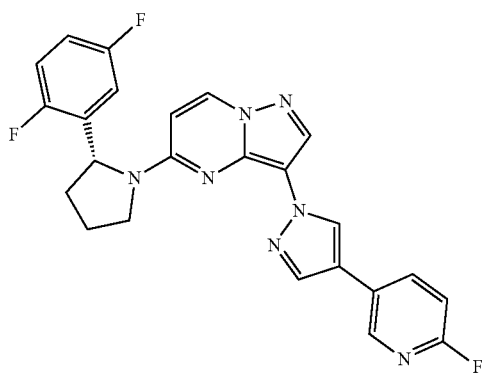 [SMILES: Fc1ccc(F)c([C@H]2CCCN2c2ccn3ncc(-n4cc(-c5ccc(F)nc5)cn4)c3n2)c1] |
| I-220 | 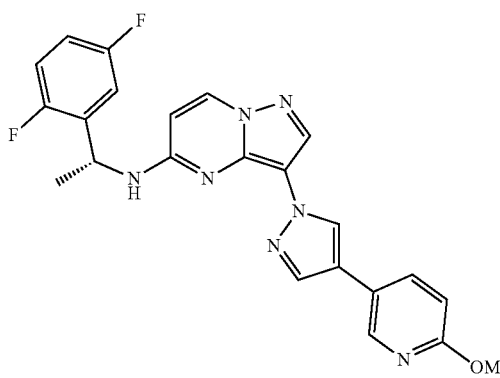 |
| I-221 | 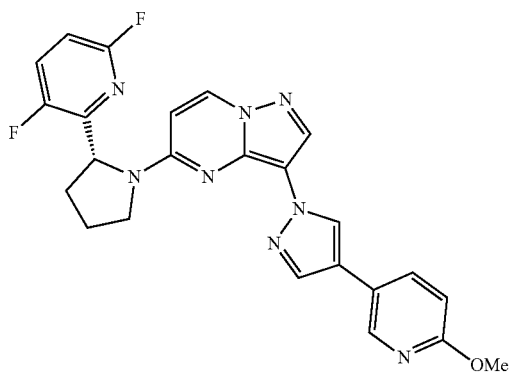 [SMILES: COc1ccc(-c2cnn(-c3cnn4ccc(N5CCC[C@@H]5c5nc(F)ccc5F)nc34)c2)cn1] |
| I-222 | 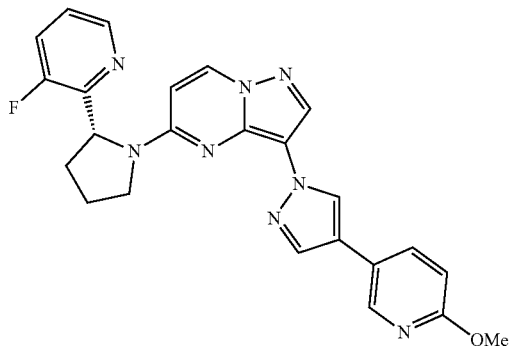 [SMILES: COc1ccc(-c2cnn(-c3cnn4ccc(N5CCC[C@@H]5c5ncccc5F)nc34)c2)cn1] |
| I-223 | 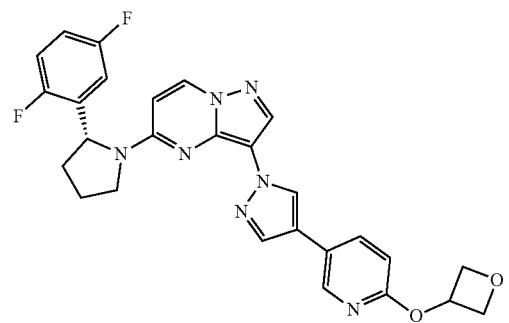 [SMILES: Fc1ccc(F)c([C@H]2CCCN2c2ccn3ncc(-n4cc(-c5ccc(OC6COC6)nc5)cn4)c3n2)c1] |
| I-224 | 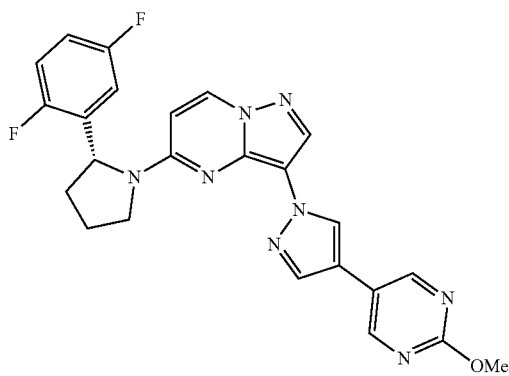 |

| Cmp No. | Structure |
|---|---|
| I-225 | ![structure with difluorophenyl-pyrrolidinyl-pyrazolopyrimidine-pyrazole acetyl] |
| I-226 | ![structure with difluorophenyl-pyrrolidinyl-pyrazolopyrimidine-pyrazole-CH2OMe] |

In another embodiment of the application, the compounds of Formula (IV) are enantiomers. In some embodiments the compounds are the (<5)-enantiomer. In other embodiments the compounds are the (i?)-enantiomer. In yet other embodiments, the compounds of Formula (IV) may be (+) or (−) enantiomers.

It should be understood that all isomeric forms are included within the present application, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the application, and pharmaceutically acceptable salts, hydrates, solvates, stereoisomers and prodrugs thereof may exist in their tautomeric form (for example, as an amide or imino ether). All such tautomeric forms are contemplated herein as part of the present application.

The compounds of the application may contain asymmetric or chiral centers, and, therefore, exist in different stereoisomeric forms. It is intended that all stereoisomeric forms of the compounds of the application as well as mixtures thereof, including racemic mixtures, form part of the present application. In addition, the present application embraces all geometric and positional isomers. For example, if a compound of the application incorporates a double bond or a fused ring, both the cis- and trans-forms, as well as mixtures, are embraced within the scope of the application. Each compound herein disclosed includes all the enantiomers that conform to the general structure of the compound. The compounds may be in a racemic or enantiomerica!ly pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Moshers acid chloride), separating the diastereomers and converting (e.g., hydrolyzing) the individual diastereomers to the corresponding pure enantiomers. Also, some of the compounds of the application may be atropisomers (e.g., substituted biaryls) and are considered as part of this application. Enantiomers can also be separated by use of a chiral HPLC column.

It is also possible that the compounds of the application may exist in different tautomeric forms, and ail such forms are embraced within the scope of the appiication. Also, for example, all keto-enol and imine-enamine forms of the compounds are included in the application.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this application, as are positional isomers (such as, for example, 4-pyridyl and 3-pyridyl). (For example, if a compound of Formula (IV) incorporates a double bond or a fused ring, both the cis- and trans-forms, as well as mixtures, are embraced within the scope of the application. Also, for example, all keto-enol and imine-enamine forms of the compounds are included in the application.) Individual stereoisomers of the compounds of the application may, for example, be substantially free of other isomers, or may be admixed, for example, as racemates or with all other, or other selected, stereoisomers. The chiral centers of the present application can have the S or R configuration as defined by the IUPAC 1974 Recommendations. 'The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula (IV) may form salts which are also within the scope of this application. Reference to a compound of the Formula herein is understood to include reference to salts thereof, unless otherwise indicated.

The present application relates to compounds which are modulators of one or more Trk kinases. In one embodiment, the compounds of the present application are inhibitors of a Trk kinase. In another embodiment, the compounds of the present application are inhibitors of more than one Trk kinase.

The application is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof Method for Preparation of Compounds The compounds of the present application may be made by a variety of methods, including standard chemistry. Suitable synthetic routes are depicted in the Schemes given below.

The compounds of Formula (IV) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (IV).

Those skilled in the art will recognize if a stereocenter exists in the compounds of Formula (IV). Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. When, and L. N. Mander (Wiley -Interscience, 1994).

The compounds described herein may be made from commercially available starting materials or synthesized using known organic, inorganic, and/or enzymatic processes.

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below. Compounds of the present application can be synthesized by following the steps outlined in General Scheme 1 Starting materials are either commercially available or made by known procedures in the reported literature or as illustrated.

Abbreviations used in the following schemes and elsewhere herein are:
DCM dichloromethane
DIPEA A.Wdiisopropylcthylaminc
DMF N, A-dimethylformamide
DMSO dimethyl sulfoxide
DMPAO (2,6-Dimethylanilino)(oxo)acetic Acid
ESI electrospray ionization
EtOAc ethyl acetate
EtOH ethanol
h hours
HCl hydrogen chloride
HPLC high performance liquid chromatography
IPA iso-propyl alcohol
LCMS liquid chromatography-mass spectrometry
MeCN acetonitrile
MeOH methanol
NBS N-bromosuccinimide
NMP N-methyl-2-pyrrolidone
min minutes
MS mass spectrometry
Rf retention factor
Rt retention time
THF tetrahydrofuran
TFA trifluoroacetic acid
LG leaving group
PG protecting group

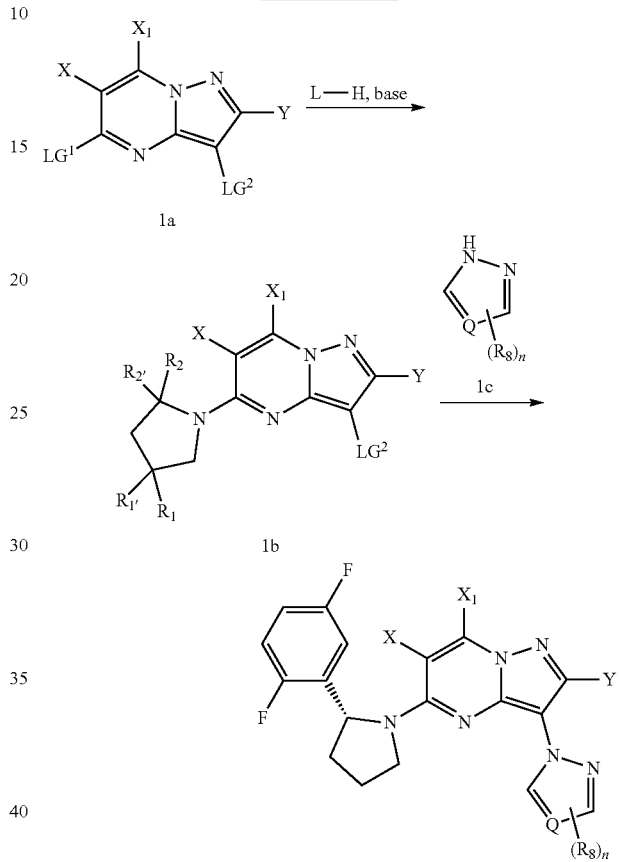

General Scheme 1 wherein X, $X_1$, L, Y, Q, $R_1$, $R_{1'}$, $R_2$, $R_{2'}$, $R_3$, $R_4$, $R_5$, $R_6$, $R_7$, $R_8$, $R_9$, $R^W$, $R^{S1}$, $R^{S2}$, $R^a$, $R^b$, $R^c$, $R^d$, R, $R^g$, $R^h$, $R^i$, R.*, n, and p are defined as in Formula (IV).

The general way of preparing compounds of Formula (IV) wherein L is a pyrrolidine is outlined in General Scheme 1. Amination of aa with L-H using a base, e.g., N,N-diisopropylethylamine (DIPEA) or sodium hydride (NaH), in a solvent, e.g, acetonitrile (MeCN), dioxane, at elevated temperature yields 1b. Nucleophilic addition of 1c to 1b in the presence of metal catalyst (e.g., copper iodide (CuT)), tripotassium phosphate, and (2,6-Dimethylanilino)(oxo)acetic Acid (DMPAO), in a solvent, i.e., dimethylsulfoxide (DMSO), at elevated temperature provides the desired compound of Formula (IV).

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the various groups A, L, Q, X, Xi, Y Ri, Rr, R2, R2, R3-R7, Re, R9, n, and p, and other variables are as defined above, except where otherwise indicated. Furthermore, for synthetic purposes, the compounds of General Scheme 1 are mere representative with elected radicals to illustrate the general synthetic methodology of the compounds of Formula (IV) as defined herein.

Methods of Using the Compounds

Another aspect of the application relates to a method of treating or preventing a disease or disorder associated with modulation of a Trk kinase. The method comprises administering to a patient in need of a treatment for diseases or disorders associated with modulation of a Trk kinase an effective amount the compositions and compounds of Formula (IV), or a pharmaceutically acceptable salt, hydrate, solvate, prodrug, stereoisomer, or tautomer thereof.

In another aspect, the application relates to a method of treating or preventing a disease or disorder associated with modulation of one or more Trk kinases. The method comprises administering to a patient in need of a treatment for diseases or disorders associated with modulation of one or more Trk Kinases an effective amount the compositions and compounds of Formula (IV), or a pharmaceutically acceptable salt, hydrate, solvate, prodrug, stereoisomer, or tautomer thereof.

Another aspect of the present application relates to a method of treating, preven ting, inhibiting or eliminating a disease or disorder in a patient associated with the inhibition of a Trk kinase, the method comprising administering to a patient in need thereof an effective amount of a compound of Formula (IV), or a pharmaceutically acceptable salt, hydrate, solvate, prodrug, stereoisomer, or tautomer thereof. In one embodiment, the disease or disorder is cancer.

In another aspect, the present application relates to a method of treating, preventing, inhibiting or eliminating a disease or disorder in a patient associated with the inhibition of one or more Trk kinases, the method comprising administering to a patient in need thereof an effective amount of a compound of Formula (IV), or a pharmaceutically acceptable salt, hydrate, solvate, prodrug, stereoisomer, or tautomer thereof.

Another aspect of the application relates to a method of inhibiting a Trk kinase. The method involves administering to a patient in need thereof an effective amount of a compound of Formula (IV), or a pharmaceutically acceptable salt, hydrate, solvate, prodrug, stereoisomer, or tautomer thereof.

In another aspect, the application relates to a method of inhibiting one or more Trk kinases. The method involves administering to a patient in need thereof an effective amount of a compound of Formula (IV), or a pharmaceutically acceptable salt, hydrate, solvate, prodrug, stereoisomer, or tautomer thereof.

Another aspect of the present application relates to a compound of Formula (IV), or a pharmaceutically acceptable salt, hydrate, solvate, prodrug, stereoisomer, or tautomer thereof, for use in a method of treating or preventing a disease associated with inhibiting a Trk kinase.

In another aspect, the present application relates to a compound of Formula (IV), or a pharmaceutically acceptable salt, hydrate, solvate, prodrug, stereoisomer, or tautomer thereof, for use in a method of treating or preventing a disease associated with inhibiting one or more Trk kinases.

Another aspect of the present application relates to the use of a compound of Formula (IV), or a pharmaceutically acceptable salt, hydrate, solvate, prodrug, stereoisomer, or tautomer thereof, in the manufacture of a medicament for treating or preventing a disease associated with inhibiting a Trk kinase.

Another aspect of the present application relates to the use of a compound of Formula (IV), or a pharmaceutically acceptable salt, hydrate, solvate, prodrug, stereoisomer, or tautomer thereof, in the manufacture of a medicament for treating or preventing a disease associated with inhibiting one or more Trk kinases.

The present application also relates to the use of an inhibitor of a Trk kinase for the preparation of a medicament used in the treatment, prevention, inhibition or elimination of a disease or condition mediated by a Trk kinase, wherein the medicament comprises a compound of Formula (IV).

The present application also relates to the use of an inhibitor of one or more Trk kinases for the preparation of a medicament used in the treatment, prevention, inhibition or elimination of a disease or condition mediated by one or more Trk kinases, wherein the medicament comprises a compound of Formula (IV).

In another aspect, the present application relates to a method for the manufacture of a medicament for treating, preventing, inhibiting, or eliminating a disease or condition mediated by a Trk kinase, wherein the medicament comprises a compound of Formula (IV).

In another aspect, the present application relates to a method for the manufacture of a medicament for treating, preventing, inhibiting, or eliminating a disease or condition mediated by one or more Trk kinases, wherein the medicament comprises a compound of Formula (IV).

Another aspect of the application relates to a method of treating or preventing a disease or disorder associated with modulation of a Trk kinase fusion. Tire method comprises administering to a patient in need of a treatment for diseases or disorders associated with modulation of a Trk kinase fusion an effective amount the compositions and compounds of Formula (IV), or a pharmaceutically acceptable salt, hydrate, solvate, prodrug, stereoisomer, or tautomer thereof.

In another aspect, the application relates to a method of treating or preventing a disease or disorder associated with modulation of one or more Trk kinase fusions. The method comprises administering to a patient in need of a treatment for diseases or disorders associated with modulation of one or more Trk kinase fusions an effective amount the compositions and compounds of Formula (IV), or a pharmaceutically acceptable salt, hydrate, solvate, prodrug, stereoisomer, or tautomer thereof.

Another aspect of the present application relates to a method of treating, preventing, inhibiting or eliminating a disease or disorder in a patient associated with the inhibition of a Trk kinase fusion, the method comprising administering to a patient in need thereof an effective amount of a compound of Formula (IV), or a pharmaceutically acceptable salt, hydrate, solvate, prodrug, stereoisomer, or tautomer thereof. In one embodiment, the disease or disorder is cancer.

In another aspect, the present application relates to a method of treating, preventing, inhibiting or eliminating a disease or disorder in a patient associated with the inhibition of one or more Trk kinase fusions, the method comprising administering to a patient in need thereof an effective amount of a compound of Formula (TV), or a pharmaceutically acceptable salt, hydrate, solvate, prodrug, stereoisomer, or tautomer thereof.

Another aspect of the application relates to a method of inhibiting a Trk kinase fusion. The method involves administering to a patient in need thereof an effective amount of a compound of Formula (IV), or a pharmaceutically acceptable salt, hydrate, solvate, prodrug, stereoisomer, or tautomer thereof.

In another aspect, the application relates to a method of inhibiting one or more Trk kinase fusions. Tire method involves administering to a patient in need thereof an effective amount of a compound of Formula (IV), or a pharmaceutically acceptable salt, hydrate, solvate, prodrug, stereoisomer, or tautomer thereof.

Another aspect of the present application relates to a compound of Formula (IV), or a pharmaceutically acceptable salt, hydrate, solvate, prodrug, stereoisomer, or tautomer thereof, for use in a method of treating or preventing a disease associated with inhibiting a Trk kinase fusion.

In another aspect, the present application relates to a compound of Formula (IV), or a pharmaceutically acceptable salt, hydrate, solvate, prodrug, stereoisomer, or tautomer thereof, for use in a method of treating or preventing a disease associated with inhibiting one or more Trk kinase fusions.

Another aspect of the present application relates to the use of a compound of Formula (IV), or a pharmaceutically acceptable salt, hydrate, solvate, prodrug, stereoisomer, or tautomer thereof, in the manufacture of a medicament for treating or preventing a disease associated with inhibiting a Trk kinase fusion.

Another aspect of the present application relates to the use of a compound of Formula (IV), or a pharmaceutically acceptable salt, hydrate, solvate, prodrug, stereoisomer, or tautomer thereof, in the manufacture of a medicament for treating or preventing a disease associated with inhibiting one or more Trk kinase fusions.

The present application also relates to the use of an inhibitor of a Trk kinase fusion for the preparation of a medicament used in the treatment, prevention, inhibition or elimination of a disease or condition mediated by a Trk kinase fusion, wherein the medicament comprises a compound of Formula (IV).

The present application also relates to the use of an inhibitor of one or more Trk kinase fusions for the preparation of a medicament used in the treatment, prevention, inhibition or elimination of a disease or condition mediated by one or more Trk kinase fusions, wherein the medicament comprises a compound of Formula (IV).

In another aspect, the present application relates to a method for the manufacture of a medicament for treating, preventing, inhibiting, or eliminating a disease or condition mediated by a Trk kinase fusion, wherein the medicament composes a compound of Formula (IV).

In another aspect, the present application relates to a method for the manufacture of a medicament for treating, preventing, inhibiting, or eliminating a disease or condition mediated by one or more Trk kinase fusions, wherein the medicament comprises a compound of Formula (IV).

In some embodiments of the methods above, the disease or disorder is selected from inflammatory diseases, infections, autoimmune disorders, stroke, ischemia, cardiac disorder, neurological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma, and wade angle glaucoma.

In some embodiments, the cancer is selected from lung adenocarcinoma, intrahepatic cholangicarcinoma, colon, papillary thyroid cancer, pediatric glioma, sarcoma, glioblastoma, spitzoid neoplasms, astrocytoma, head and neck squamous cell carcinoma, low grade glioma, high grade glioma, acute myeloid leukemia, congenital mesoblastic nephroma, mammary analogue secretory carcinoma, thyroid cancer, Ewing sarcoma, adenoid cystic carcinoma, and cylindromas.

In other embodiments, the present application relates to the use of an inhibitor of a Trk kinase for the preparation of a medicament used in treatment, prevention, inhibition or elimination of a disease or disorder associated with cancer.

In other embodiments, the present application relates to the use of an inhibitor of one or more Trk kinases for the preparation of a medicament used in treatment, prevention, inhibition or elimination of a disease or disorder associated with cancer.

In another embodiment, the present application relates to a compound of Formula (IV) or a pharmaceutical composition comprising a compound of the present application and a pharmaceutically acceptable carrier used for the treatment of cancers.

In some embodiments of the methods described herein, the cancer is selected from adrenocortical carcinoma, A anal cancer, cerebellar astrocytoma, extrahepatic bile duct cancer, bladder cancer, osteo sarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypophaiyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, rnerkel cell carcinoma, metastatic squamous neck cancer with occult primary', multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity' and paranasal sinus cancer, nasopharyngeal cancer, neuroblastoma, glioblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastema, prostate cancer, rectal cancer, renal cell (kidney) cancer, transitional cell cancer (e.g., renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous t-cell!ymphoma, testicular cancer, malignant thymoma, thyroid cancer, gestational trophoblastic tumor, urethral cancer, uterine sarcoma, vaginal cancer, vulvar cancer, and Wilms' tumor. In other embodiments, the cancer is a non-small cell lung cancer. In other embodiments of the methods described herein, the cancer is a dedifferentiated ID-driven cancer. In yet other embodiments, the cancer is a hematologic cancer. In other embodiments, the cancer is a cancer that is sensitive to Trk kinase inhibiton.

In some embodiments of the methods described herein, the cancer is selected from prostate cancer, pancreatic cancer, breast cancer, colorectal cancer, lung cancer, neuroblastoma, glioblastoma, medulloblastoma, adenocarcinomas, Ewing sarcoma, and leukemias.

In any of the embodiments of the application, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In any of the embodiments of the application, the cancer can develop through the action of one or more gene fusions. Such gene fusions are often known as "driver fusions" or "driver gene fusions" and can include, but are not limited to, gene fusions involving genes that encode Trk kinases. Exemplary gene fusions include, but are not limited to, TPM3-NTRK1, ETV6-NTRK3, MPRIP-NTRK1, CD74-NTRK1, RABGAP1L-NTRK1, TPR-NTRK1, TFG NTRK1, PPL-NTRK1, CHTOP-NTRK1, ARH-GEF2-NTRK1, NFASC-NTRK1 BCAN-NTRK1, LMNA-NIRK1, TP53-NTRK1, QK1-NTRK2, NACC2-NTRK2, VCL-NIRK2, AGBL4-NIRK2, TRIM24-NIRK2, PAN3-NIRK2, AFAP1-NTRK2, SQSTM1-NTRK2, BTB1-NTRK3, LYN-NTRK3, and RBPMS-NTRK3.

In other embodiments, the cancer is selected from liposarcoma, neuroblastoma, glioblastoma, bladder cancer, adrenocortical cancer, multiple myeloma, colorectal cancer, non-small cell lung cancer, gastric cancer, rectal cancer, thyroid cancer, Hodgkin lymphoma and diffuse large B-cell lymphoma.

Another aspect of the application is directed to pharmaceutical compositions comprising a compound of Formula (IV), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

In one embodiment, methods of treating a disease or disorder associated with modulation of one or more Trk kinases including, inflammatory, diseases, infections, autoimmune disorders, stroke, ischemia, cardiac disorder, neurological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma, and wide angle glaucoma, comprise administering to a patient suffering from at least one of said diseases or disorder a compound of Formula (IV).

One therapeutic use of the compounds or compositions of the present application which inhibit one or more Trk kinases is to provide treatment to patients or subjects suffering from inflammatory' diseases, infections, autoimmune disorders, stroke, ischemia, cardiac disorder, neurological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma, or wide angle glaucoma.

The disclosed compounds of the application can be administered in effective amounts to treat or prevent a disorder and/or prevent the development thereof in subjects.

Compounds of the application can be administered in therapeutically effective amounts in a combinational therapy with one or more therapeutic agents (pharmaceutical combinations) or modalities, e.g., non-drug therapies. For example, synergistic effects can occur with other anti -proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent or a second agent that targets a Trk kinase-independent mechanism of DNA repair) and non-drug therapies (such as, but not limited to, surgery' or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Application and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DMA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TOPS or other acceptable emulsifier; and/or g) an agent that enhances absorption of the compound such as cyclodextrin, hydroxypropyl-cyclodextrin, PEG400, and PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or scrum proteins can be used to solubilize the disclosed compounds.

The disclosed compounds can be also formulated as a suppository that can be prepared from fatty emulsions or suspensions; using polyalkylene glycols such as propylene glycol, as the earner.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the application is directed to pharmaceutical compositions comprising a compound of Formula (IV) and a pharmaceutically acceptable carrier. The pharmaceutical acceptable carrier may further include an excipient, diluent, or surfactant.

The dosage regimen utilizing the disclosed compound is selected in accordance with a variety of factors including type, species, age, weight, sex and medical condition of the patient; the severity' of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 or 400 MHz. Spectra are given in ppm (δ) and coupling constants, J, are reported in Hertz. Tetramethylsilane (TMS) was used as an internal standard. Mass spectra wore collected using a Waters ZQ Single Quad Mass Spectrometer (ion trap ESI). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, ELSD and ESI Column: Acquity UPLC BEH C18 1.7 μm, 2.1×50 mm; Flow rate 0.6 mL/min; Solvent A (95/5/0. 1 10 mM ammonium formate/acetonitrile/formic acid), Solvent B (95/5/0.09 acetonitrile/water/formic acid); gradient: 5-100% B from 0 to 2 min, hold 100% B to 2.2 min, then 5% B at 2.21 min.

Example 1: (R)-5-(2-(2,5-difluorophenyl)pyrrolidin-1-yl)-3-(1H-pyrazol yl)pyrazolo[1,5-a]pyrimidine (1-152)

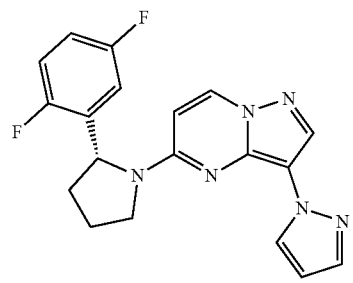 [SMILES: Fc1ccc(F)c([C@H]2CCCN2c2ccn3ncc(-n4cccn4)c3n2)c1]

Step 1. (R)-5-(2-(2,5-difluorophenyl)pyrrolidin-1-yl)-3-iodopyrazolo[1,5-a]pyrimidine

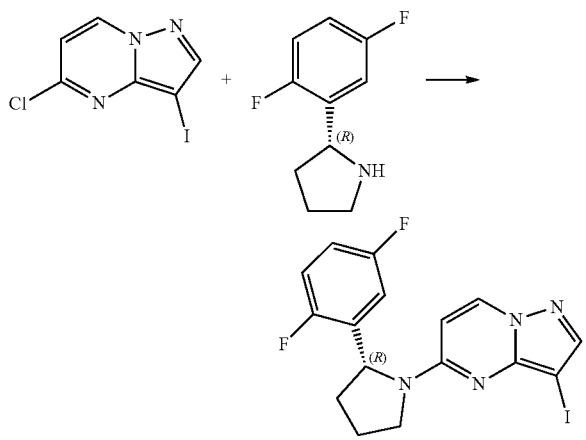

To a solution of (R)-2-(2,5-difluorophenyl)pyrrolidine hydrochloride (4040 mg, 18.393 mmol) and 5-chloro-3-iodopyrazolo[1,5-a]pyrimidine (4.67 g, 16.721 mmol) in DMF (33 mL) was added DIPEA (1E7 mL, 66.88 mmol). The mixture was stirred at 90° C. for 3 hour and then cooled to it. The mixture was poured over 1.2 L of water and the precipitate was collected by filtration. The filtrate was also extracted with AcOEt and concentrated and the materials were combined to afford product as a yellow solid (7.1 g, 100%) which was used such as.

Step 2. (R)—S-(2-(2,5-difluorophenyl)pyrrolidin-J-yl)-3-(1H-pyrazol-1-yl)pyrazolo[J5-a]pyrimidine

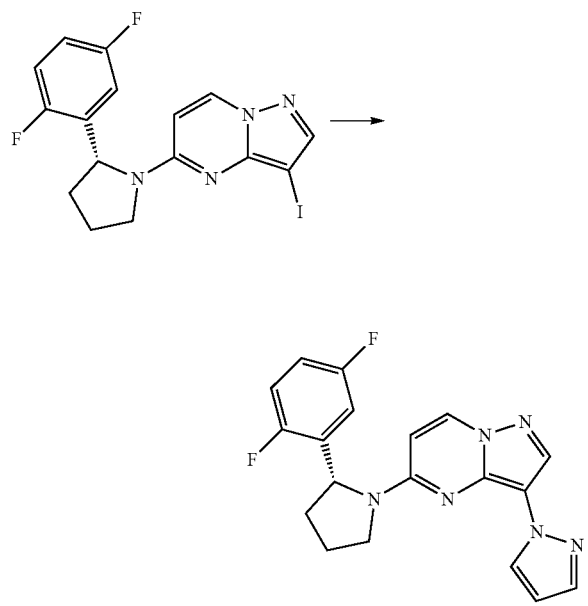

A solution of trans-N,N'-dimethylcyclohexane-1,2-diamine (7.0 mg, 0.049 mmol) in DMF (degassed, 1.2 mL) was added to (R)-5-(2-(2,5-difluorophenyl)pyrrolidin-1-yl)-3-iodopyrazolo[1,5-a]pyrimidine (104 mg, 0.244 mmol), 1H-pyrazole (33 mg, 0.485 mmol), copper iodide (9.3 mg, 0.049 mmol) and potassium carbonate (67 mg, 0.485 mmol). The mixture was degassed with $N_2$ (10 min) then stirred at 120° C. for 16 h. Additional portions of in pyrazole (33 mg, 2 eq), copper iodide (9.3 mg, 0.2 eq), potassium carbonate (67 mg, 2 eq) and trans-N,N'-dimethylcyclohexane-1, 2-diamine (7.0 mg, 0.2 eq) were added. The reaction mixture was degassed with $N_2$ (10 min) then stirred at 120° C. for 16 h. Water was added. The mixture was extracted with EtOAe (3×). Combined organic layers were washed with water (1×) and with brine (1×), dried over MgSO4, filtered and concentrated under reduced pressure. The product was purified by normal chromatography using 30-100% EtOAe in hexanes and then by reverse chromatography using 30-80% MeCN in AmFor 10 mM buffer to afford title compound as a pale yellow-solid (37 mg, 41%). 1H NMR (400 MHz, DMSO) δ 8.77-8.41 and 7.80-7.51 (m, 3H), 8.17 (s, 1H), 7.37-6.87 (m, 3H), 6.69-6.44 (m, 1H), 6.33 (s) and 6.11-5.96 (m) 11H), 5.46-5.29 (m, 1H), 4.01 (dt, I=11.4, 5.8 Hz, 1H), 3.82-3.62 (m, 1H). 2.56-2.38 (m, 1H), 2.16-1.81 (m, 3H); MS (m/z): 367.2 [M+1]+, >99%, Example 2: (R)-5-(2-(3,6-difluoropyridin-2-yl)pyrrolidin-1-yl)-3-(4-methyl-1H-pyrazol-1-yl)pyrazolo[1,5-a]pyrimidine (1-154)

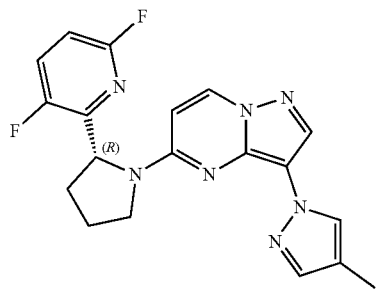

Step 1. 4-chloro-1-(3,6-difluoropyridm-2-y!)butan-1-one

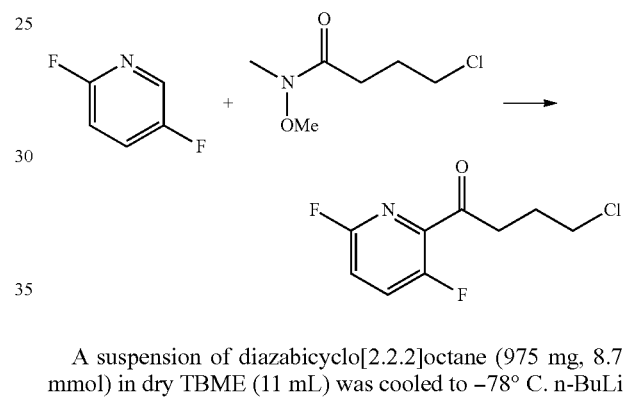

A suspension of diazabicyclo[2.2.2]octane (975 mg, 8.7 mmol) in dry TBME (11 mL) was cooled to −78° C. n-BuLi (3.5 mL, 2.5 M in hexane, 8.7 mmol) was added dropwise to the suspension. The mixture was stirred for approximately 30 min at −78° C. and then treated dropwise with 2,5-difluoropyridine (1000 mg, 8.7 mmol) in dry TBME (0.5 mL). After 1 h, 4-chloro-N-methoxy-N-methylbutanamide (1439 mg, 8.7 mmol) in dry TBME (0.9 mL) was added dropwise to the mixture at −78° C. The solution was stirred for 1 h, and the reaction was quenched with saturated aqueous NH4Cl (10 mL). The mixture was diluted with EtOAe (20 mL) and allowed to warm to room temperature overnight. The aqueous phase was extracted further with EtOAe (3×20 mL), and the combined organic phases were washed with saturated aqueous NaHCO3 (50 mL) and brine (50 mL), dried over MgSO4, and concentrated under reduced pressure to afford title compound as orange oil (1900 mg, 100%»). Used without further purification.

Step 2. (S,E)-N-(4-chloro-1-(3,6-difluoropyridin-2-yl)butylidene)-2-methylpropane sulfinamide

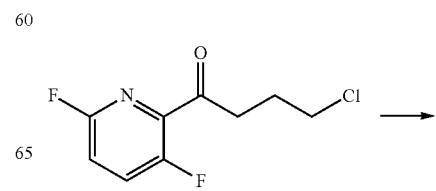

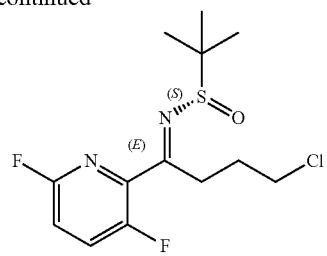

In a 50 mL RBF containing 4-chloro-1-(3,6-difluoropyridin-2-yl)butan-1-one (500 mg, 2.3 mmol) under nitrogen at room temperature was added THF (5.6 mL) followed by (S)-2-methylpropane-2-sulfinamide (414 mg, 3.4 mmol) and titanium ethoxide (0.72 mL, 3.4 mmol). Mixture stirred in a 70° C. oil bath for 20h and the reaction was done by TLC. The flask was cooled with icy-water bath and saturated aqueous NH4Cl added (~50 mL, white solid formation); diluted with EtOAc, sonicated and solid was filtered off. Filtrate diluted in EtOAc, washed with w³/⁴ter and brine. Organic layer was dried over anh. Na2SO4, filtered and solvent evaporated to give as yellow oil. Crude purified on SiO₂ using Combiflash (40 g column, w³/⁴tload, 0→30% EtOAc/Hex) to afford title compound as yellowish oil (365 mg, 50%).

Step 3. 2—(R)-1-((S)-tert-butylsulfinyl)pyrrolidin-2-yl)-3,6-difluoropyridine

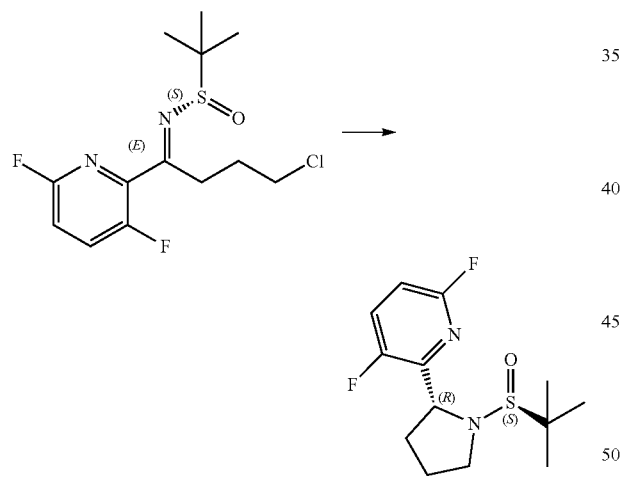

(S,E)-N-(4-chloro-1-(3,6-difluoropyridin-2-yJ)butyhdene)-2-methylpropane-2-sulfmamide (365 mg, 1.1 mmol) was dissolved in THF (4.2 mL) under nitrogen in a round bottom flask. Mixture cooled at −78° C. and slowly Super-H (1.1 mL, 1.1 mmol) was added dropwise (temperature never reach higher that −70° C.). Mixture stirred at −78° C. After 3 hour, LiHMDS (1.3 mL, 1.3 mmol) was then added dropwise at −78° C., the mixture w³/₄s stirred 30 min at −78° C. and the mixture w³/₄s allowed to warm at 0° C. over 30 min. After 1 hour at 0° C., the reaction w-as cooled back to −78° C. and saturated aqueous NH4Cl was added. The mixture was allowed to warm to rt and EtOAc was added. The aqueous layer was extracted 3 times with EtOAc, Combined organic layers were dried over anh. MgSO4, filtered. Then, silica is added and solvent evaporated. The residue was purified using a gradient of 0 to 25% acetone in hexanes to afford title compound (141 mg, 43%) as transparent oil.

Step 4. (R)-3,6-difluoro-2-(pyrrolidin-2-yl)pyridine

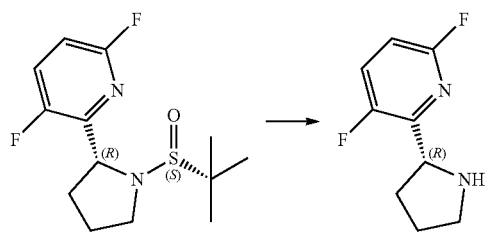

To a solution of 24(R)-14(S)-tert-butylsulfmyl)pyrrolidin-2-yl)-3,6-difluoropyridine (138 mg, 0.048 mmol) in methanol (10 mL) was added HCl (480 uL, 1.91 mmol) in dioxane. The mixture was stirred 60 min at 0° C. and it was concentrated to give (R)-3,6-difluoro-2-(pyrrolidin-2-yl) pyridine: (88 mg, 100%) which was used without further purification.

Step 5. (R)-3-bromo-5-(2-(3,6-difluoropyridin-2-yl) pyrrolidin-1-yl)pyrazolo[J5-ajpyrimidine

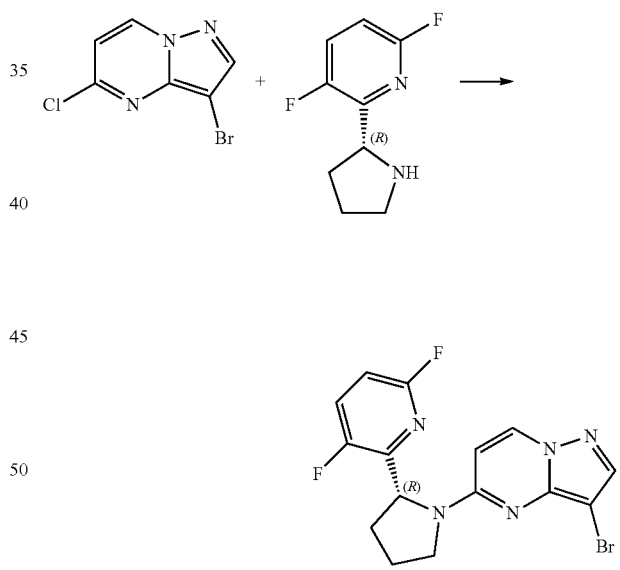

A mixture of 3-bromo-5-chloropyrazolo[1,5-a]pyrimidine (111 mg, 0.48 mmol), (R)-3,6-difluoro-2-(pyrrolidin-2-yl) pyridine (88 mg, 0.48 mmol) and DIPEA (34 μL, 1.91) in DMF (5 mL) was stirred at 20° C. for 3 days. The mixture was diluted with NH4C1, the aqueous layer was extracted three times with EtOAc, and the organic layer was dried over Na2SO4, filtered and concentrated. The residue was purified by normal phase chromatography using a gradient of 0 to 25% acetone in hexanes and by reverse phase chromatography using a gradient of 0 to 100% MeCN in a solution of 10 mM AmForm to afford title compound as white solid (140 mg, 77%).

Step 6. (R)—S-(2-(3,6-difluoropyridin-2-yl)pyrrolidin-1-yl)-3-(4-methyl-1H-pyrazol-1-yl]pyrazolo[1,5-a]pyrimidine

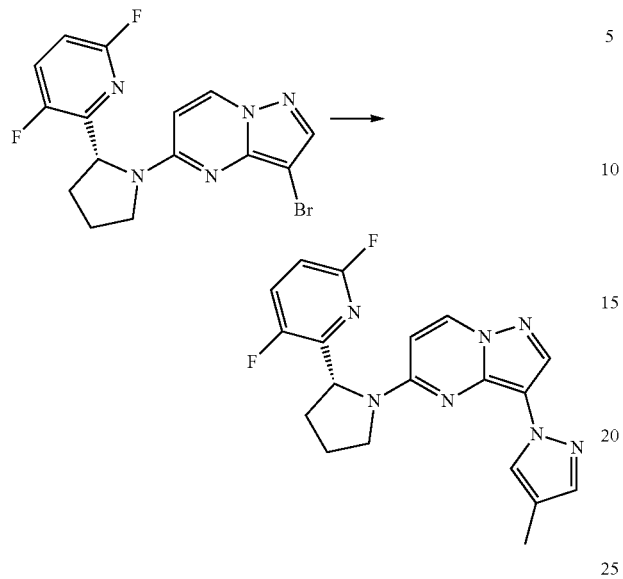

A mixture of copper iodide (2.8 mg, 0.015 mmol), potassium carbonate (30 nig, 0.217 mmol) and trans-N,N'-dimethyicyclohexane-1,2-diamine (4.7 mg, 0.033 mmol) in DMF (degassed, 0.10 mL) was stirred at room temperature for 10 min. 4-Methyl-1H-pyrazole (12 mg, 0.146 mmol) was added followed by a solution of (R)-3-bromo-5-(2-(3,6-difluoropyridm-2-yi)pyrroloidin~1-yflpyrazoloj 1,5-a]pyrimidme (31 mg, 0.073 mmol) in DMF (degassed, 0.26 mL). The reaction mixture was stirred at 120° C. for 16 h. Water was added to quench reaction. The mixture was extracted with EtOAc (3×), Combined organic layers were washed with water (1×) and with brine (1×), dried over MgSQ4, fdtered and concentrated under reduced pressure. The product was purified using normal chromatography using 30-80% AcOEt in hexanes and the by reverse chromatography using 40-70% MeCN in AmFor buffer to afford title compound as a pale yellow' solid (3.5 mg, 13%) after lyophilisation.

1H NMR (400 MHz, DMSO) δ 8.68 (d, J=7.5 Hz, 1H), 8.11 (s, 1H), 7.92 (dd, J=15.7, 8.6 Hz, 1H), 7.68 (s, 1H), 7.37 (s, 1H), 7.12-7.05 (m, 1H), 6.60 (d, J=7.7 Hz, 1H), 5.45 (dd, J=8.5, 3.8 Hz, 1H) 3.89-3.80 (m, 1H), 3.79-3.71 (m, 1H) 2.31-2.19 (m, 1H), 2.12 (s, 3H), 2.17-2.04 (m, 2H), 2.00-1.90 (m, 1H): MS (m/z): 382.2 [M+I]+, >99%

Example 3, (R)-4-(1-(5-(2-(2,5-difluorophenyl)pyrrolidin-1-yl)pyrazolo[1,5-a]pyrimidin-3-yl)-1H-pyrazol-4-yl)-3,5-dimethylisoxazole (1-157)

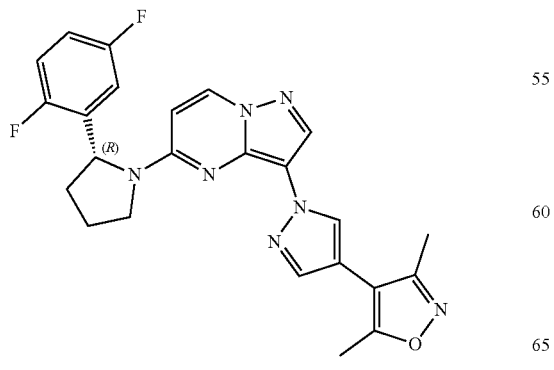

Step 1. (R)-3-(4-bromo-1H-pyrazol-1-yl)-5-(2-(2,5-difluorophenyl)pyrrolidin-1-yl]pyrazoio[1,5-a]pyrimidine

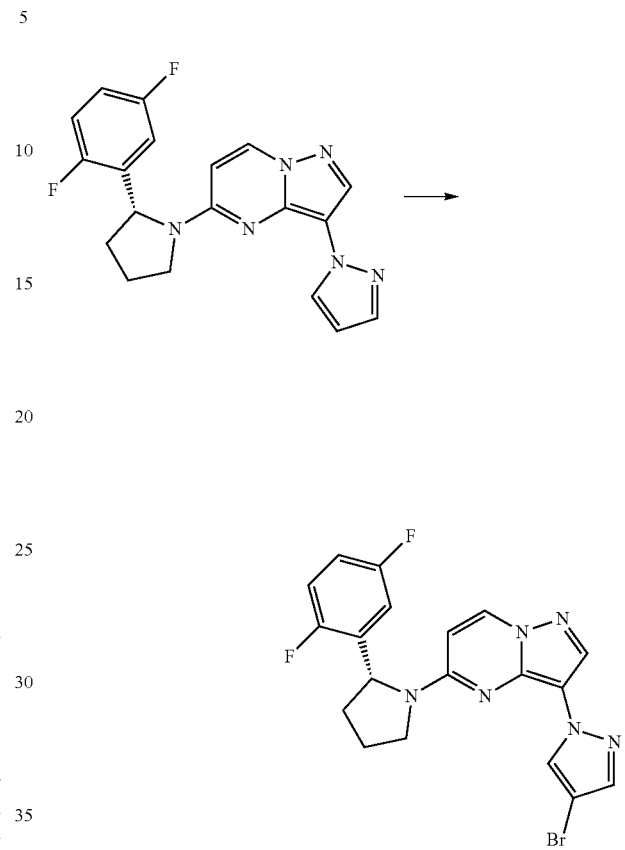

(R)-5-(2-(2,5-difluorophenyl)pyrrolidin-1-yl)-3-(1H-pyrazol-1-yl)pyrazolo[T,5-a]pyrimidine (500 mg, 1.36 mmol) was dissolved in MeCN (14 mL) to which was added NBS (267 mg, 1.50 mmol) and the mixture was stirred at rt. Upon completion, the reaction diluted with ethyl acetate and washed (1×) with water/brine, dried over sodium sulfate, filtered and concentrated to dryness. The product was purified by normal chromatography using 0-3% MeOH in DCM to afford product as a yellow solid (434 mg, 72%).

Step 2. (R)-4-(1-(5-(2-(2,5-difluoropheny!)pyrrolidin-1-yl)pyrazolo[1,5-a]pyrimidin-3-yl)-1H-pyrazol-4-yl)-3,5-dimethylisoxazole

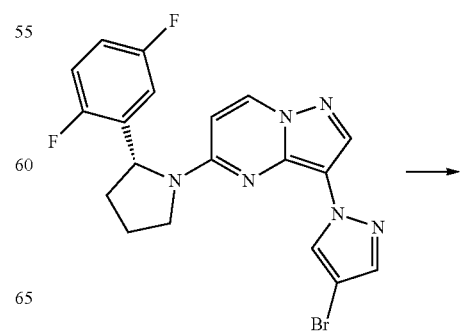

73

-continued

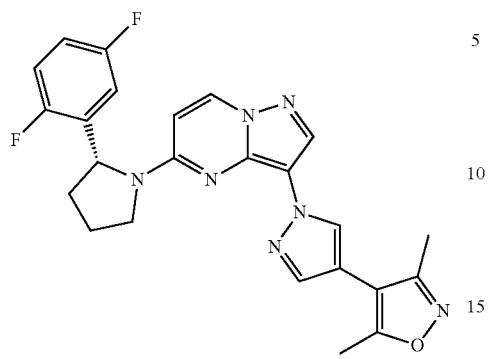

(R)-3-(4-bromo-1H-pyrazol-1-yl)-5-(2-(2,5-difluorophenyl)pyrrolidin-1 yl)pyrazolo[1,5-a]pyrimidine (25 mg, 0.056 mmol), Cs$_2$CO$_3$ (55 mg, 0.168 mmol), Pd(dppf)Cl2.dcm (8.2 mg, 0.012 mmol) and 3,5-dimethylisoxazole-4-boronic acid (12 mg, 0.084 mmol) were charged in a sealed tube. A solution of degassed dioxane/water (10/1, 0.6 mL) was added and the reaction was heated at 130° C. for 1 hour. The reaction mixture was concentrated to dryness and the product was purified by reverse phase chromatography using 0-100% MeCN in water and the by normal phase chromatography using 0-5% MeOH in DCM. The product was lyoplulized to afford a white solid (11.7 mg, 45%). 1H NMR (500 MHz, DMSO) δ 8.85-8.63 (m, 1H), 8.62-8.50 (m, 1H), 8.35-8.14 (m, 1H), 7.99-7.82 (m, 1H), 7.81-7.66 (m, 1H), 7.43-6.73 (m, 3H), 6.72-6.56 (m, 1H), 6.17-5.96 (m, 1H), 5.60-5.27 (m, 1H), 4.11-3.95 (m, IID. 3.87-3.57 (m, 1H), 2.48-1.77 (m, 10H); MS (m/z): 462.2 [M+i]+, 0.96%.

Example 4. (R)-1-(5-(2-(2,5-difluorophenyl)pyrrolidiii-1-yl)pyrazolo[1,5-a]pyrimidin yl)-1H-pyrazole-4-carbonitrile (I-170)

Step 1. (R)-1-(5-(2-(2,5-difluorophenyl)pyrrolidin-1-yl)pyrazolo[J5-a]pyrimidin-3-yl)-1H-pyrazole-4-carbonitrile

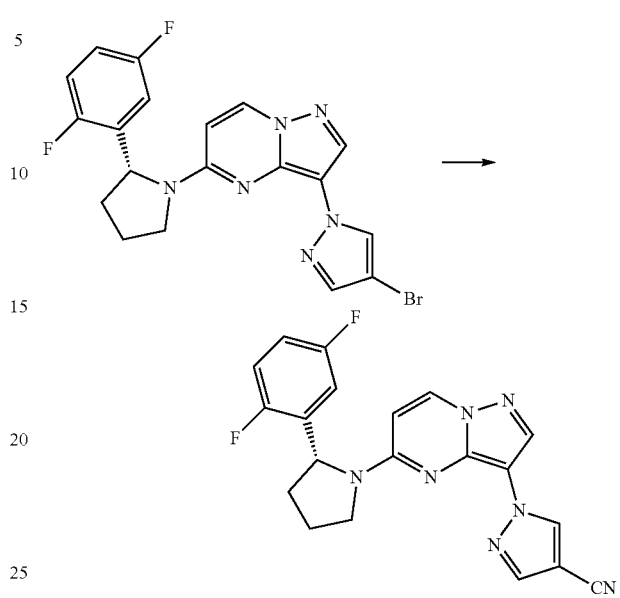

A mixture of (R)-3-(4-bromo-1H-pyrazol-1-yl)-5-(2-(2,5-difluorophenyl)pyrrolidin-1-yl)pyrazolo[1,5-a]pyrimidine (50 mg, 0.112 mmol), zinc cyanide (8 mg, 0.068 mmol), tris(dibenzylideneacetone)-dipalladium(0) (6.2 mg, 0.007 mmol) and 1,1-bis(diphenylphosphino)ferrocene (8.1 mg, 0.015 mmol) in DMF (1.2 mL, degassed) was stirred at at 120° C. for 16 h. Water was added and the mixture was extracted with EtOAc (3×). Combined organic layers were washed with water (1×) and with brine (1×), dried over MgSO4, filtered and concentrated under reduced pressure. The product was purified by normal chromatography using 30-80% AcOEt in hexanes and then by reverse chromatography using 20-80% MeCN in AmFor 10 mM buffer to afford product as an off-white solid (22 mg, 49%) after lyophilisation. 1H NMR (400 MHz, DMSO) δ 9.16-9.07 (m) and 8.77 (d, J=7.8 Hz) (1H), 8.65-8.54 and 8.36-8.19 (m, 3H), 7.39-7.05 and 6.99-6.86 (m, 3H), 6.68 (d, J 7.6 Hz) and 6.14-6.05 (m) (1H), 5.48-5.31 (m, 1H), 4.11-3.96 (m, 1H), 3.87-3.64 (m, 1H), 2.57-2.40 (m, 1H), 2.21-1.81 (m, 3H); MS (m/z): 392.2 [M+1]+, >99%.

Example 5, (R)-1-(5-(2-(2,5-difluorophenyl)pyrrolidin-1-yl)pyrazolo[1,5-a]pyrimidin yl)-1H-pyrazole-4-carboxamide (I-173)

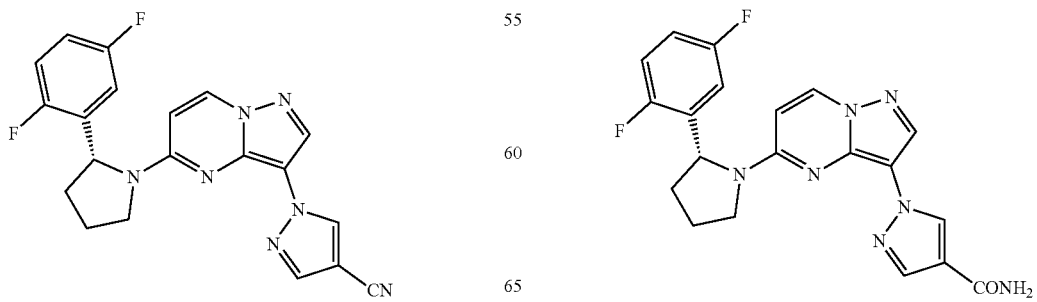

Step 1. (R)-1-(5-(2-(2,5-difluorophenyl)pyrrolidin-1-yl)pyrazolo[1,5-c]pyrimidin-3-yl)-1H pyrazole-4-carboxamide Step 1. (R)-(1-(5-(2-(2,$-difluorophenyl)pyrrolidin-1-yl)pyrazolo[1,5-a]pyrimidin-3-yl)-1H pyrazol-1-yl)dimethylphosphine oxide

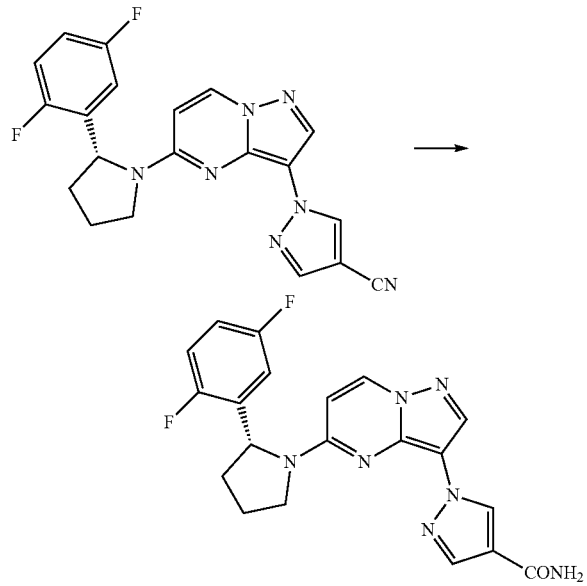

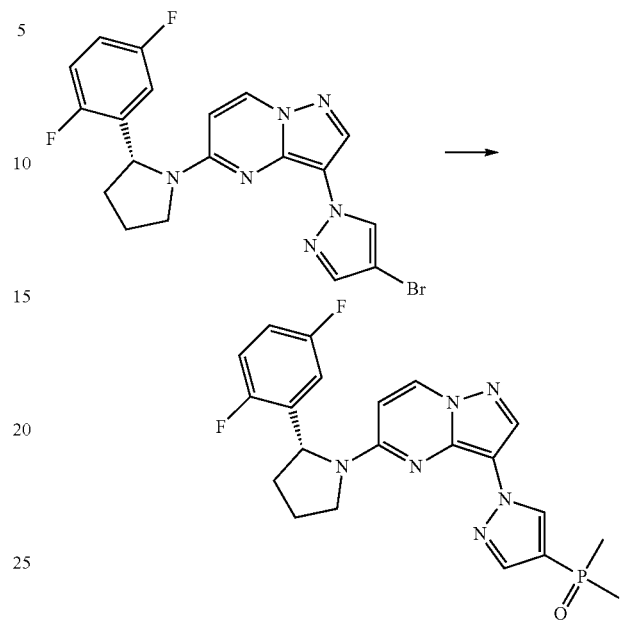

2.5 M aqueous NaOH (0.5 mL) was added to a mixture of (R)-1-(5-(2-(2,5-difluoroplienyl)pyrrolidm-1-yl)pyrazolojT,5-a]pyrimidm-3-yl)-1H-pyrazole-4-carbonitrile (31 mg, 0.079 mmol) in ethylene glycol (1.6 mL). The reaction mixture was stirred at 100° C. for 16 h. IN aqueous HCl (4 mL) was added. Precipitate was collected by filtration and washed with water. The product was purified by reverse chromatography using 5-60% MeCN in ArnFor 10 mM buffer to afford product as an off-white solid (1.7 mg, 5%) after lyophilisation. 1HNMR (400 MHz, DMSO) δ 8.84-8.67 (m, 1H), 8.63-8.50 and 8.31-8.15 (m, 2H), 8.10-7.92 (m, 1H), 7.80-7.69 and 7.55-7.44 and 7.39-6.89 (m, 5H), 6.69-6.58 and 6.13-6.02 (m, 1H), 5.58-5.29 (m, 1H), 4.11-3.95 (m, 1H), 3.87-3.60 (m, 1H). 2.58-2.40 (m, 1H), 2.16-1.82 (m, 3H); MS (m/z): 410.1 [M+1]+, >99%.

Example 6, (R)-(1-(5-(2-(2,5-difluorophenyl)pyrrolidm-1-yl)pyrazolo[1,5-a]pyrimidin-3-yl)-1H-pyrazol-4-yl)dimethylphosphine oxide (1-174)

A solution of dimethylphosphine oxide (12 mg, 0.154 mmol) in DMF (0.4 mL, degassed) was added to a mixture of (R)-3-(4-bromo-1H-pyrazol-1-yl)-5-(2-(2,5-difluorophenyl)pyrrolidin-1-yl)pyrazolo[1,5-a]pyrimidine (56 mg, 0.126 mmol), palladium acetate (1.4 mg, 0.006 mmol), Xantphos (7.2 mg, 0.012 mmol) and K3PO4 (32 mg, 0.151 mmol) in DMF (0.2 mL, degassed). The reaction mixture was then stirred at 150° C. (MW) for 45 min. Some drops of water were added and the product was purified by reverse chromatography using 5-70% MeCN in AmFor 10 mM buffer to afford product as an off-white solid (12.5 mg, 22%) after lyophilization. 1H NMR (400 MHz, DMSO) δ 8.81-8.66 (m, 1H), 8.64-8.53 and 8.14-8.06 (m, 1H), 8.30-8.20 (m, 1H), 7.99-7.82 (m, 1H), 7.40-7.26 (m, 1H), 7.24-6.91 (m, 2H), 6.71-6.58 and 6.13-6.02 (m, 1H), 5.61-5.49 and 5.41-5.31 (m, 1H), 4.11-3.98 (m, 1H), 3.85-3.57 (m, 1H), 2.56-2.38 (m, 1H), 2.15-1.82 (m, 3H), 1.76-1.56 (m, 6H); MS (m/z): 443.2 jM+iJ+, >99%.

Example 7. (R)-5-(2-(2,5-difliiorophenyl)pyrrolidin-1-yl)-3-(4-(3,6-dihydro-2H-pyran-4-yl)-1H-pyrazol-1-yl)pyrazolo[1,5-a]pyrimidine (I-175)

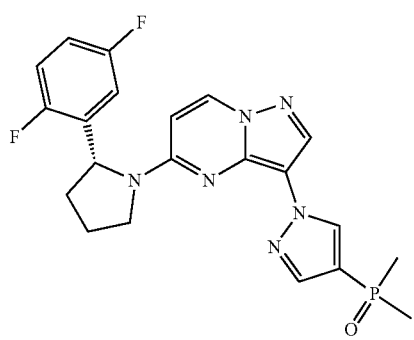 [SMILES: CP(C)(=O)c1cnn(-c2cnn3ccc(N4CCC[C@@H]4c4cc(F)ccc4F)nc23)c1]

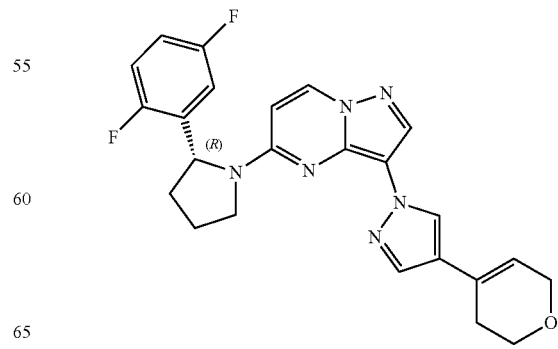

Step 1. (R)-5-(2-(2,5-difluorophenyl)pyrrolidin-1-yl)-3-(4-(3,6-dihydro-2H-pyran-4-yl-1H-pyrazol-1-yl)pyrazolo[1,5-a]pyrimidine

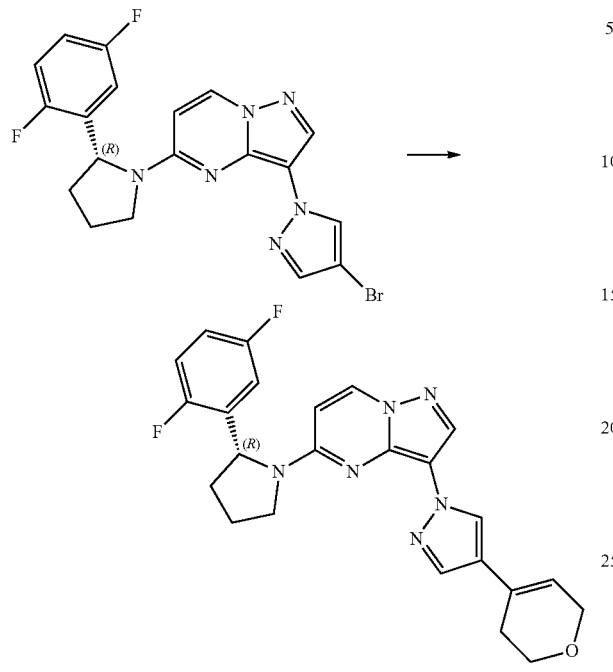

A mixture of (R)-3-(4-bromo-1H-pyrazol-1-yl)-5-(2-(2,5-difluorophenyl)pyrrolidin-1-yl)pyrazolo[1,5-a]pyrimidine (100 mg, 0.225 mmol), 3,6-dihydro-2H-pyran-4-boronic acid pinacol ester (57 mg, 0.270 mmol), Pd(PPh3)4 (26 mg, 0.022 mmol) and Na2CO3 (119 mg, 1.123 mmol) was stirred under atmosphere of N2 and in degassed solution of dioxane and water (4:1; 2.25 mL) at 85° C. for 18 h. The mixture was diluted with EtOAc, washed with NH4Cl dried over MgSO4, filtrated and concentrated. The residue was purified by normal phase chromatography using a gradient of 0 to 100% acetone in hexanes to afford title compound as yellow solid (45 mg, 45%). 1H NMR (500 MHz, CDCl3) δ 8.63-7.83 (m, 3H), 7.74-7.57 (m, 1H), 7.10-6.82 (m, 2H), 6.76-6.64 (m, 6.41-6.14 (m, 1H), 6.06-5.73 (m, 1H), 5.75-5.13 (m, 1H), 4.33 (q, J=2.7 Hz, 2H), 3.99-3.58 (m, 4H), 2.56-2.26 (m, 3H), 2.17-2.02 (m, 3H); MS (m/z): 449.3 jAM]+, >99%.

Example 8. (R)-5-(2-(2,5-difluorophenyl)pyrrolidln-1-yl)-3-(4-(tetrahydro-2H-pyrasi-4-yl)-1H-pyrazoM-yl)pyrazolo[1,5-a]pyrsmidine (1-187)

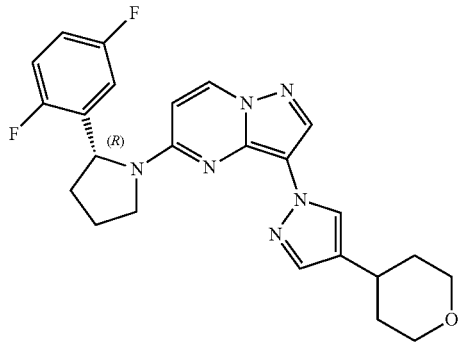

Step 1. (R)-5-(2-(2,5-difluorophenyi)pyrrolidin-1-yl)-3-(4-(tetrahydro-2H-pyran-4-yl)-1H-pyrazol-1-yl)pyrazolo[1,5-a]pyrimidine

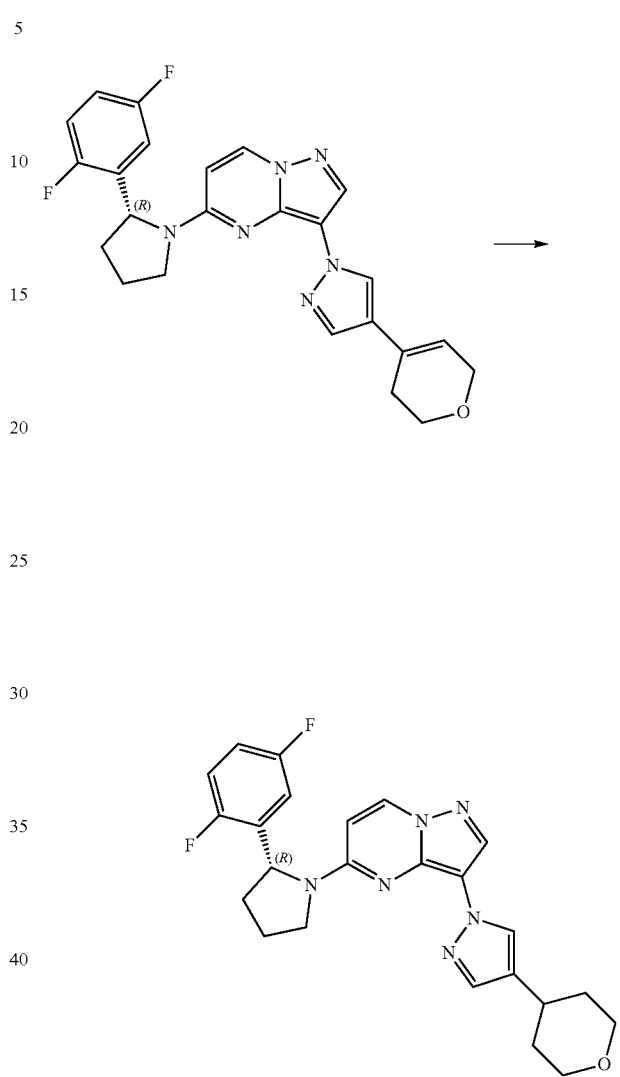

In a vial, (R)-5-(2-(2,5-difluorophenyl)pyrrolidin-1-yl)-3-(4-(3,6-dihydro-2H-pyran-4-yl)-1H-pyrazol-1-yl)pyrazolo[1,5-a]pyrimidine (30 mg, 0.067 mmol) was dissolved in MeOH (2 mL) to which was added 0.1 mL AcOH. Pd/C (10% per weight, 20 mg) and a balloon of hydrogen was fitted to the vial. The mixture is stirred for multiple days with refilling hydrogen as needed and the reaction is followed by 1 cms (7 min runs). After 5 days of stirring with hydrogen, 60% conversion had occurred and the reaction was stopped. The palladium was filtered out and the solvent evaporated. The product was purified by semi-prep HPLC using 40-55% MeCN in AmFor to afford product as an off-white solid (4.1 mg, 14%) after lyophilisation. NMR (500 MHz, CDCl$_3$) δ 8.37-8.08 (m, 2H), 7.73 (br s, 7.45 (br s, 1H), 7.11-6.68 (m, 3H), 6.42-5.79 (m, 1H) 5.72-5.09 (m, iH) 4.14-4.01 (m, 2H), 3.99-3.61 (m, 2H), 3.62-3.50 (m, 2H), 2.92-2.59 (m, 2H) 2.55-2.39 (m, 1H), 2.20-1.98 (m, 3H), 1.90-1.69 (m, 3H); MS (m/z): 451.3 [M+1]+, >99%.

Example 9. (R)-3-(4-(Difluoro methyl)-1H-pyrazol-1-yl)-5-(2-(2,5-difluorophenyl)pyrrolidin-1-yl)pyrazolo[1,5-a]pyrimidine (1-176)

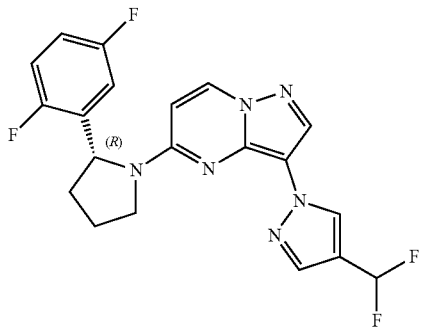

Step 1. (R)-1-(5-(2-(2,5-difluorophenyl)pyrrolidin-1-yl)pyrazolo[1,5-a]pyrimidin-3-yl)-1H-pyrazole-4-carbaldehyde

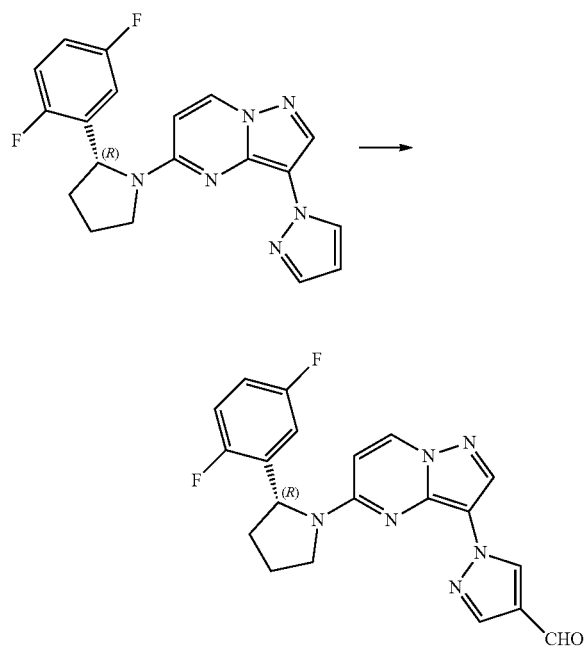

A vial with a magnetic stir bar was charged with DMF (1.7 mL). The vial was then cooled in an ice bath, and POCl3 (0.05 mL, 0.478 mmol) was added dropwise. The mixture was stirred for 30 min at 0° C., followed by dropwdse addition of a solution of (R)-5-(2-(2,5-difiuorophenyl)pyrrolidin-1-yl)-3-(1H-pyrazol-1-yl)pyrazolo[1,5-a]pyrimidine (5.0 g, 61 mmol) in DMF (1 mL) over 5 min. The mixture is then stirred at 70° C. for 18 h. The solution was then chilled to 0° C., and saturated aqueous NaHCO3 was added until the reaction was no longer acidic. The resulting mixture was extracted with EtOAc (3×200 mL), and the extracts were dried over MgSCM and concentrated in vacuo. The product (70.5 mg, 95%) was not purified further and W³/₄S used such as.

Step 2. (R)-3-(4-(difluoromethyl)-1H-pyrazol-1-yl)-5-(2-(2,5-difluorophenyl)pyrrolidin-1-yl)pyrazolo[1,5-a pyrimidine

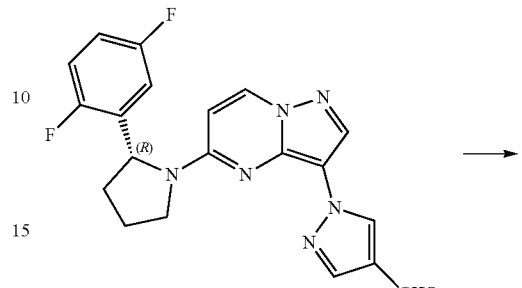

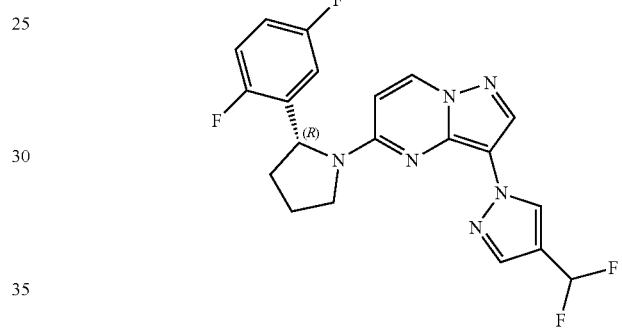

A solution of DAST (26 mg, 0,161 mmol) was added to a solution of (R)-1-(5-(2-(2,5-difluoroplienyl)py rrolidin-1-yl)pyrazolo[1,5-a]pyrimidm-3-yl)-1H-pyrazole-4-carb aldehyde (52.8 mg, 0.134 mmol) in DCM (2 mL) at 0° C. The reaction mixture was stirred at room temperature for 7 h then an additional portion of DAST (53 μL, 3 eq) was added. The reaction mixture was stirred at room temperature for 16 h then an additional portion of DAST (90 pL, 5 eq) was added. The reaction mixture was stirred at room temperature for 16 h then an additional portion of DAST (180 pL, 10 eq) was added. Then reaction mixture was stirred at room temperature for 16 h. Water was added and the mixture was extracted with DCM (3×). Combined organic layers were dried over MgSO4, filtered and concentrated under reduced pressure. The product was purified by normal chromatography using 30-100% AcOEt in hexanes and then by reverse chromatography using 20-70% MeCN in AmFor 10 mM buffer to afford product as an off-white solid (16 mg, 28%) after lyophilisation. 1H NMR (400 MHz, DMSO) δ 8.81-8.69 (m, 1H), 8.64-8.52 (m) and 8.03 (s) (1H), 8.32-8.19 (m, 1H), 7.96-7.79 (m, 1H), 7.41-6.89 (m, 4H), 6.70-6.58 and 6.12-6.02 (m, 1H), 5.51-5.30 (m, 1H). 4.03 (dt, J=11.4, 5.7 Hz, 1H), 3.82-3.63 (m, 1H), 2.57-2.39 (m, 1H), 2.18-1.82 (m, 3H): MS (n/z): 417.2 [M+1]+, >99%.

Example 10. (R)-2-(1-(5-(2-(2,5-difluorophenyl)pyrrolidin-1-yl)pyrazolo[1,5-a]pyrimidin-3-yl)-1H-pyrazol-4-yl)-5-methyl-1,3,4-oxadiazole (I-178)

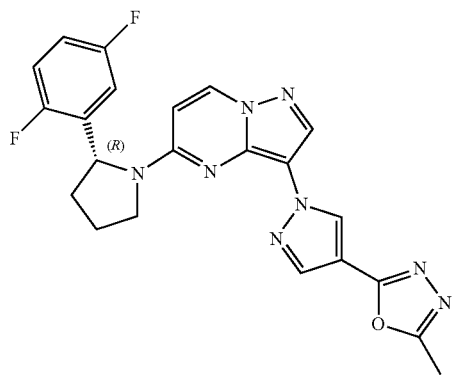

Step 1. (R)-1-(5-(2-(2,5-difluorophenyl)pyrrolidin-1-yl)pyrazolo[J5-a]pyrimidin-3-yl)-1H-pyrazole-4-carboxylic acid

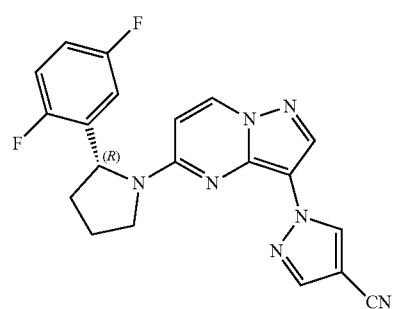

2.5 M aqueous NaOH (0.5 mL) was added to a mixture of (R)-1-(5-(2-(2,5-difluorophenyl)pynOlidin-1-yl)pyrazolo[1,5-a]pyrimidin-3-yl)-1H-pyrazole-4-carbonitrile (31 mg, 0.079 mmol) in ethylene glycol (1.6 mL). The reaction mixture was stirred at 100° C. for 16 h. IN aqueous HCl (4 mL) was added. Precipitate was collected by filtration and washed with water. The product was purified by reverse chromatography using 5-60% MeCN in AmFor 10 mM buffer to afford product as an off-white solid (6. 3 mg, 19%) after lyophilisation.

Step 2. (R)-2-(1-(5-(2-(2,5-difluorophenyl)pyrrolidin-1-yl)pyrazolo[J 5-a]pyrimidin-3-yl)-1H-pyrazol-4-yl)-5-metkyl-1, 3,4-oxadiazole

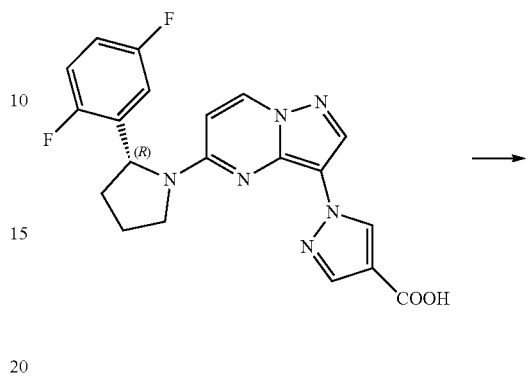

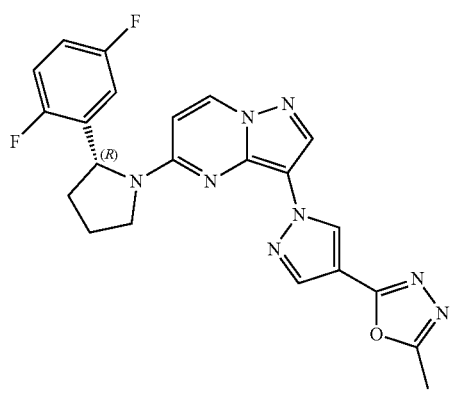

HATH (48 mg, 0.126 mmol) was added to a solution of (R)-1-(5-(2-(2,5-difluoroplienyl)pyiTolidm-1-yl)pyrazolo[1,5-a]pyrimidin-3-yl)-1H-pyrazole-4-carboxy e acid (52 mg, 0.127 mmol), acethydrazide (14 mg, 0.189 mmol) and DIPEA (44 uL, 0.253 mmol) in THF (2.5 The reaction mixture was stirred at room temperature for 3 h. Desired intermediate (R)—N'-acetyl-1-(5-(2-(2,5-difluorophenyl)pyrrolidin-1-yl)pyrazolo[1,5-a]pyrimidin-3-yl)-1H-pyrazole-4-carbohydrazide had formed with 80% as well as carboxamide side product. Burgess reagent (152 mg, 0.635 mmol) was added and the reaction mixture was stirred at room temperature for 2 h. The mixture was diluted with EtOAc then washed with water (1×) and with brine (1×), dried over MgSO4, filtered and concentrated under reduced pressure. The product was purified using reverse chromatography with 10-70% MeCN in AmFor 10 mM buffer to afford product as an off-white solid (24 mg, 43%) after lyophilisation. 1H NMR (400 MHz, DMSO) δ 9.05-8.97 and 8.84-8.74 cm, 1H), 8.65-8.56 and 8.45-8.15 (m, 3H), 7.40-7.17 (m, 1H) 7.09-6.94 (m, 2H) 6.68 (d, J=7.9 Hz) and 6.17-6.05 (m) (1H), 5.55-5.33 (m, 1H), 4.11-3.98 (m, 1H), 3.83-3.64 (m, 1H), 2.65 is, 3H), 2.71-2.39 (m, 1H), 2.16-1.82 (m, 3H); MS (m/z): 449.2 [M+1]+, >99%.

Example 11 (R)-5-(2-(2,5-difluorophenyl)pyrrolidin-1-yl)-3-(4-(oxetan-3-yloxy)-1H-pyrazol-1-yl)pyrazolo[1,5-a]pyrimidine (I-179)

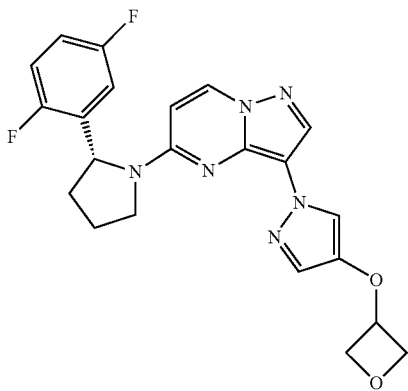 [SMILES: Fc1ccc(F)c([C@H]2CCCN2c2ccn3ncc(-n4cc(OC5COC5)cn4)c3n2)c1]

4-(oxetan-3-yloxy)-1H-pyrazole

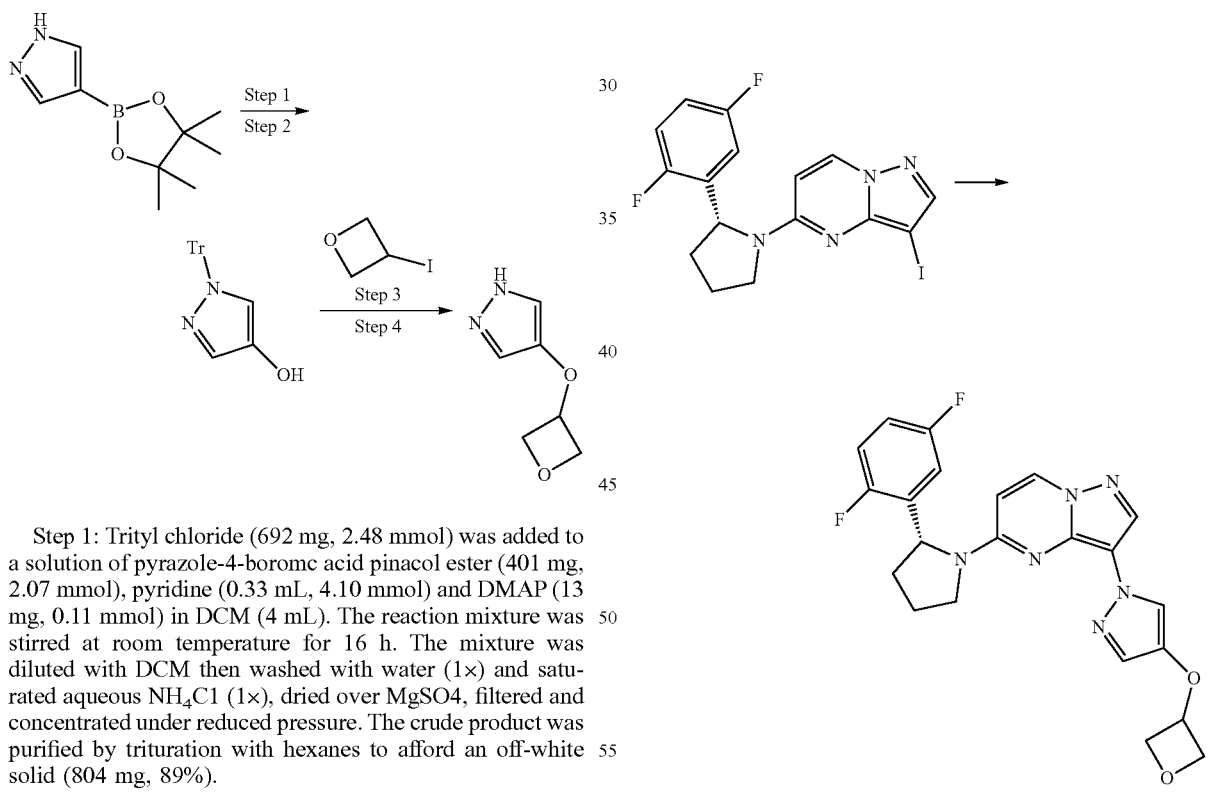

Step 1: Trityl chloride (692 mg, 2.48 mmol) was added to a solution of pyrazole-4-boronic acid pinacol ester (401 mg, 2.07 mmol), pyridine (0.33 mL, 4.10 mmol) and DMAP (13 mg, 0.11 mmol) in DCM (4 mL). The reaction mixture was stirred at room temperature for 16 h. The mixture was diluted with DCM then washed with water (1×) and saturated aqueous NH4Cl (1×), dried over MgSO4, filtered and concentrated under reduced pressure. The crude product was purified by trituration with hexanes to afford an off-white solid (804 mg, 89%).

Step 2: A solution of 2.5 M aqueous NaOH (1.28 mL) and H2O2 (30% in water, 0.37 mL) were added to a solution of 4-(4,4,5,5-tetramethyl-1,3,2-dioxaborolan-2-yl)-1-trityl-M-pyrazole (699 mg, 1.6 mmol) in THF at 0° C. The reaction mixture was stirred at room temperature for 2 h. IN aqueous HC 1 was added and the mixture was extracted with EtOAc (3×). Combined organic layers were dried over MgSO4, filtered and concentrated under reduced pressure. The product was purified by normal chromatography using 0-50% EtOAc in hexanes to afford 1-trityl-1H-pyrazol-4-ol (425 mg, 81%) as an off-white solid.

Step 3: 3-Iodooxetane (0.2 mL, 2.27 mmol) was added to a solution of -trity!-1H-pyrazol-4-ol (356 mg, 1.09 mmol) and cesium carbonate (889 mg, 2.73 mmol) in DMF (5.5 mL) at room temperature. The reaction mixture was stirred for 64 h. The reaction mixture was diluted with EtOAc then washed with H2O 2O (2×) and brine (1×). Organic layer was dried over MgSO4, filtered and concentrated under reduced pressure. The product was purified by normal chromatography using 0-30% AcOEt in hexanes to afford 4-(oxetan-3-yloxy)-1-trityl-1H-pyrazole (295 mg, 71%) as a white solid.

Step 4: TFA was added to a solution of 4-(oxetan-3-yloxy)-1-trityl-1H-pyrazole (199 mg, 0.520 mmol) in DCM (2.6 mL) and MeOH (1.3 mL) at 0° C. The reaction mixture was then stirred at room temperature for 1 h. Saturated aqueous NaHCO$_3$ was added. Tire mixture was extracted with EtOAc (4×). Combined organic layers were dried with MgSO4, filtered and concentrated under reduced pressure. Crude material was used such as in next step.

Step 1. (R)-5-(2-(2,5-difluorophenyl)pyrrolidin-1-yl)-3-(4-(oxetan-3-yloxy)-1H-pyrazol-1-yl)pyrazolofJ5-a]pyrimidine Prepared using procedure described in Example 001 using 4-(oxetan-3-yloxy)-1H-pyrazole prepared above to afford desired product as an off-white solid (17 mg, 4%). 1HNMR (400 MHz, DMSO) δ 8.77-8.66 and 8.59-8.44 (m, 1H), 8.22-8.06 (m, 1H), 7.51-7.26 (m, 3H), 7.21-6.89 (m, 2H), 6.74-6.58 and 6.09-5.98 (m, 1H), 5.56-5.30 (m, 1H), 5.23-5.11 and 4.99-4.74 (m, 3H), 4.63-4.47 (m, 2H) 4.07-3.95 (m, 1H), 3.82-3.57 (m, 1H), 2.56-2.37 (m, 1H), 2.12-1.83 (m, 3H); MS (m/z); 439.2 [M+!]+, >99%.

Example 12 (R)-5-(2-(2,5-difluerophenyl)pyrrolidin-1-yl)-3-(4-((2-methoxyethoxy)methyl)-1H-pyrazol-1-yl)pyrazolo[1,5-a]pyrimidine (I-180)

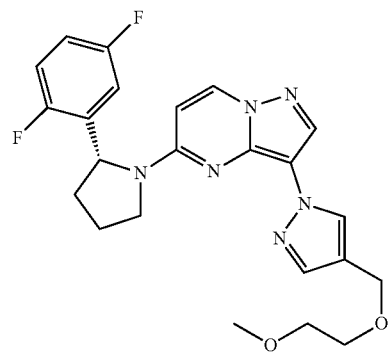 [SMILES: COCCOCc1cnn(-c2cnn3ccc(N4CCC[C@@H]4c4cc(F)ccc4F)nc23)c1]

(R)-(1-(5-(2-(2,5-difluorophenyl)pyrrolidin-1-yl)pyrazolo[J5-a]pyrimidin-3-yl)-1H-pyrazol-4-yl)methanol

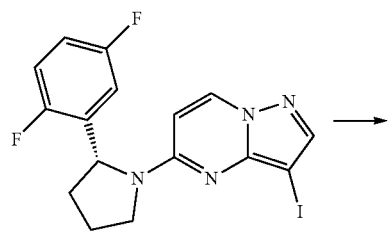

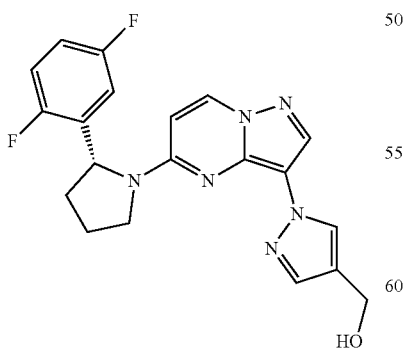

Prepared using procedure described in Example 001 using (1H-pyrazol yl)methanol to afford title compound as a pale yellow solid (24 mg, 51%) after lyophilization.

(R)-5-(2-(2,5-difluorophenyl)pyrrolidin-1-yl)-3-(4-((2-methoxyethoxy)methyl)-1H-pyrazol-1-yl)pyrazolo[1,5-a]pyrimidine

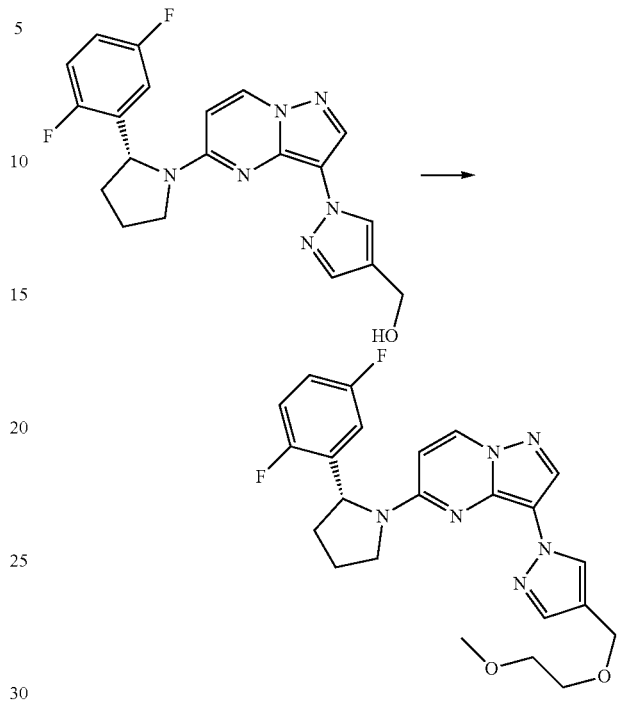

NaH (7.6 mg, 0.190 mmol) was added to a solution of (R)-(1-(5-(2-(2,5-difluorophenyl)pyrrolidin-1-yl)pyrazolo[1,5-a]pynmidin-3-yl)-1H-pyrazol-4-yl)methanoi (50 mg, 0.126 mmol) in DMF (0.85 mL) at 0° C. The reaction mixture was then stirred at room temperature for 20 min then 2-bromoethyl methyl ether was added. The reaction mixture was stirred at room temperature for 16 h. Water was added (some drops to quench NaH excess) then the mixture was directly loaded on C18 and was purified using 5-70% MeCN in AmFor 10 rnM buffer to afford product as an orange solid (19 mg, 33%) after lyophilization. 1H NMR (400 MHz, DMSG) δ 8.72 (d, J=7.3 Hz) and 8.61-8.51 (m) (1H), 8.48-8.36 (m) and 7.74 (s) (1 r) 8.26-8.13 (m, 1H), 7.66-7.50 (m, 1H), 7.39-6.89 (M, 3H, 6.62 (d, J=7.1 Hz) and 6.12-5.98 (m) (1H), 5.48-5.29 (m, 1H), 4.54-4.25 (m, 2H), 4.06-3.98 (m, 1H), 3.82-3.61 (m, 1H), 3.59-3.44 (m, 4H), 3.27 (s, 3H), 2.55-2.40 (m, 1H), 2.15-1.80 (m, 3H); MS (m/z): 455.2 [M+Tj+,>99%.

Example 13. (R)-5-(2-(2,5-difluorophenyl)pyrrolidin-1-yl)-3-(4-(methylsulfonyl)-1H-pyrazobl-yl)pyrazolo[1,5-a]pyrimidine (1-181)

87

(R)-5-(2-(2,5-difluorophenyl)pyrrolidin-1-yl)-3-(4-(methylsulfonyl)-1H-pyrazol-1-yl)pyrazolo[1,5-a]pyrimidine

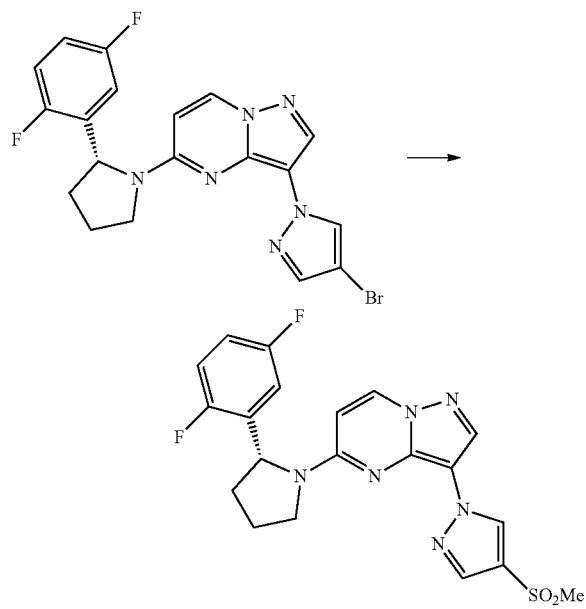

In a small vial (R)-3-(4-bromo-1H-pyrazol-1-y 1)-5-(2-(2,5-difluorophenyl)pyrroiidin-1-yl)pyrazolo[1,3-aJpyrimidine (50 mg, 0.11 mmol) in NMP (1. 1 mL) was treated with CuI (83 mg, 0.44 mmol) and sodium methyl sulfinate (46 mg, 0.45 mmol). Nitrogen was bubbled through the reaction mixture for approximately one minute and then the mixture in a sealed vial was heated at 140° C. in the oil bath. After 5 h, heating was stopped and the reaction was diluted with EtOAc. The organic layer was washed 3× with NH4QH/ 'water 1:2 and the aqueous layer was extracted 3× with EtOAc. The organic layer w³/₄s washed with NH4CJ, brine, dried over MgSO4 and concentrated. The residue was purified by normal phase chromatography using a gradient of 0 to 40% acetone in hexane and by reverse phase chromatography using a gradient of 0 to 100% MeCN in 10 mM AmForm to afford title compound as white solid (11.2 mg, 22%) after lyophilization. 1H NMR (500 MHz, CDCl₃) δ 8.96 (s, 0.5H), 8.30 (s, 2H), 8.15 (s, 0.5H), 7.93 (s, 1H), 7.24-7.06 (m, 1H), 6.91 (s, ill), 6.73 (ddd, J=8.9, 5.9, 3.2 Hz, 1H), 6.37 (s, 0.6H), 5.91 (s, 0.4H), 5.61 (s, 0.6H), 5.22 (s, 0.4H), 4.15-3.83 (m, 2H), 3.71 (s, J=4.7 Hz, 1H), 3.16 (s, 3H), 2.52 (s, 1H), 2.29-2.00 (m, 3H); MS (m/z): 445.2 [M+1]+, >99%.

Example 14 (R)-5-(2-(3-fluoropyridin-2-yl)pyrrolidin-1-yl)-3-(4-methyl-1H-pyrazol-1-yl)pyrazolo[1,5-a]pyrimidine (I-152)

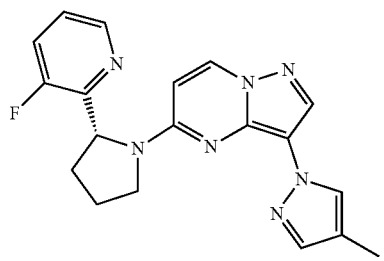 [SMILES: Cc1cnn(-c2cnn3ccc(N4CCC[C@@H]4c4ncccc4F)nc23)c1]

88

(R)-3-fluoro-2-(pyrrolidin-2-yl)pyridine

Prepared using procedure described in Example 002 using 3-fluoropyridine to afford title compound as a colorless oil (1.06 g, 1%).

(R)-5-(2-(3-fluoropyridin-2-yl)pyrrolidin-J-yi)-3-iodopyrazolo[J5-a]pyrimidine

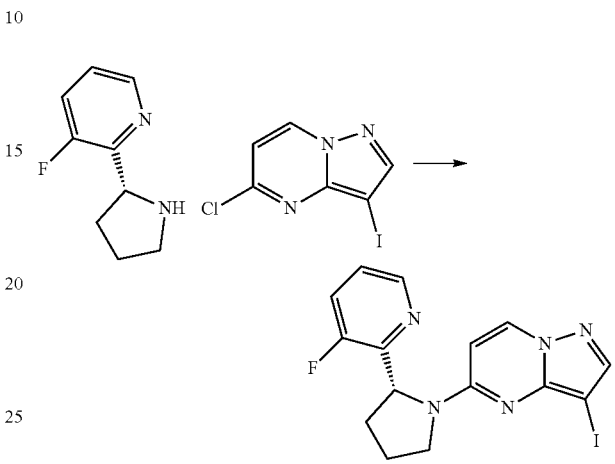

To a solution of (R)-3-iluotO-2-(pyrrolidin-2-yl)pyridine (1163 mg, 4.302 mmol) and 5-chloro-3-iodopyrazolo[1,5-a] pyrimidine (1.76 g, 6.298 mmol) in DMF (15 mL) was DIPEA (4.9 mL, 27.99 mmol). The mixture was stirred at 110° C. for 1 hour and then cooled to rt overnight. The mixture was extracted with AcOEt, dried and concentrated. The product was purified by column chromatography using 0-100% acetone in hexane. Product was isolated as an orange oil (1.42 g, 50%).

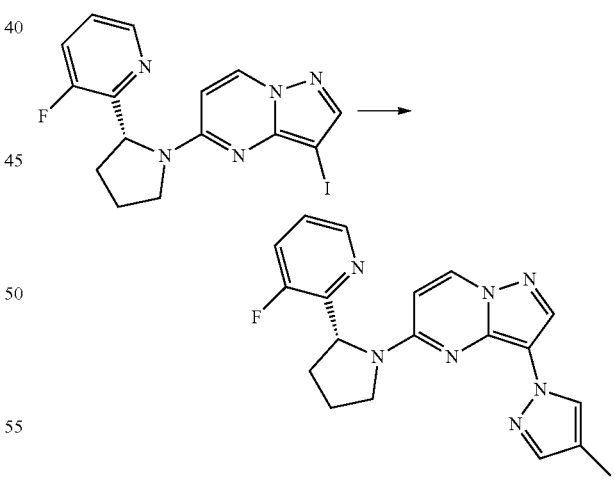

Prepared using procedure described in Example 002 using (R)-5-(2-(3-fluoropyridin-2-yl)pyrrolidin-1-yl)-3-iodopyrazolo[T,5-a] pyrimidine and 4-methyl-1H-pyrazole to afford title compound as an off-white solid (11.4 mg, 43%) after lyophilization. 1H NMR (500 MHz, CDCl₃) δ 8.34-8.13 Cm. 3H), 7.78 (br s, 1H), 7.42-7.31 (m, 2H), 7.14 (br s, 1H), 6.27 (br s, 1H), 5.70 (br s, 1H), 4.02-3.92 (m, 1H), 3.81-3.67 (m, 1H), 2.57-2.35 (m, 2H) 2.18 (s, 3H), 2.17-2.00 (m, J=24.4 Hz, 2H), MS (m/z): 364.2 j+J+, 98%.

Example 15 (R)-2-(5-(2-(2,5-difluorophenyl)pyrrolidiii-1-yl)pyrazolo[1,5-a]pyrimidin-3-yl)-2,4,6,7-tetrahydropyrano[4,3-c]pyrazole and (R)-1-(5-(2-(2,5-difluorophenyl)pyrrolidin-1-yl)pyrazolo[1,5-a]pyrimidin-3-yl)-1y 4,6,7-tetrahydropyrano[4,3-e]pyrazole (1-183 and 1-184)

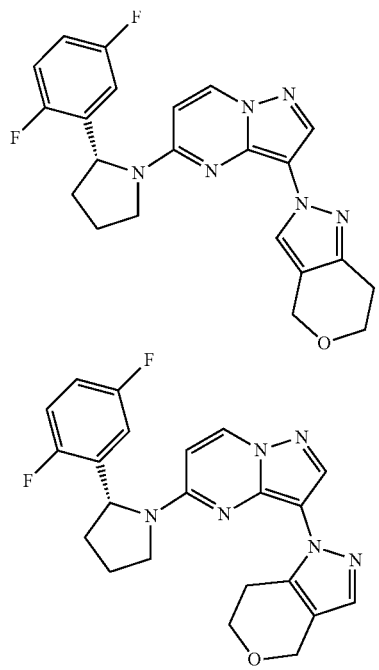

1,4,6, 7-tetrahydropyranof 4, 3-cJpyrazole

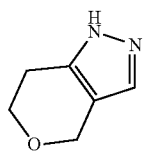

Synthesis of 1,4,6,7-tetrahydropyrano[4,3-c]pyrazole was carried out as reported in US-20 1601 85785-A1

(R)-2-(5-(2-(2,5-difluorophenyl)pyrrolidin-1-yl)pyrazolo[J5-a]pyrimidin-3-yl)-2,4,6, 7-tetrahydropyrano[4,3-c]pyrazole and (R)-1-(5-(2-(2,5-difluorophenyl)pyrrolidin-1-yl)pyrazolo[1,5-a]pyrimidin-3-yl)-1,4,6,7-tetrahydropyrano[4,3-c]pyrazole

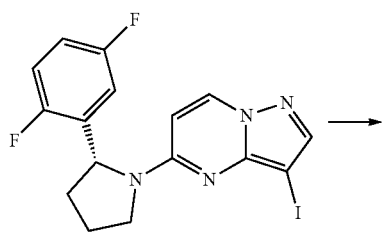

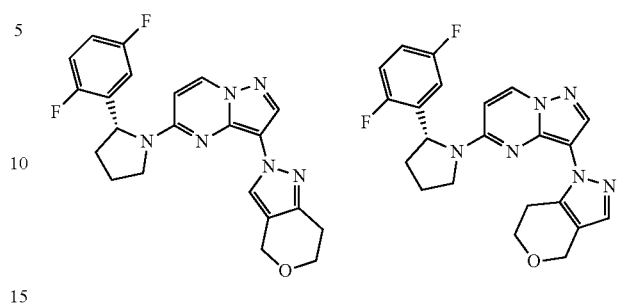

Prepared using procedure described in Example 001 using 1,4,6,7-tetrahydropyrano[4,3-c]pyrazole to afford (R)-2-(5-(2-(2,5-difluorophenyl)pyrrolidin-1-yl)pyrazolo[1,5-a]pyrimidin-3-yl)-2,4,6,7-tetrahydropyrano[4,3-c]pyrazole as a yellow solid (10.6 mg, 18%) after lyophilization: 1H MMR (500 MHz, CDCl$_3$) δ 8.33-8.00 (m, 2H), 7.51 (s, 1H), 7.10-6.69 (m, 3H), 6.42-5.77 (m, 1H), 5.55-5.13 (m, all. 4.89-4.59 (m, 2H), 4.11-3.60 (m, 4H), 2.96-2.79 (m, 2H), 2.60-2.40 (m, 1H), 2.27-1.95 (m, 3G): MS (m/z): 423.3 [M+!]+, >99%, and (R)-1-(5-(2-(2,5-difluorophenyl)pyrrolidin-1-yl)pyrazolo[1,5-a]pyrimidin-3-yl)-1,4,6,7-tetrahydropyrano[4,3-c]pyrazole as a yellow solid (3.2 mg, 5%) after lyophilization: 1H NMR (500 MHz, CDCl$_3$) δ 8.33-8.12 (m, 1H), 8.07 (s, 1H), 7.44 (br s, 1H), 7.10-7.01 (m, 1H), 6.96-6.86 (m, 1H), 6.72-6.62 (m, 1H), 6.39-5.83 (m, 1H), 5.58-5.13 (m, Mi). 4.84-4.59 (m, 2H), 4.00-3.48 (m, 5H), 2.97-2.74 (m, 1H), 2.51-2.34 (m, 114). 2.12-1.94 (m, 3H); MS (m/z): 423.3 [M+!]+, >99%.

Example 16 (R)-(1-(5-(2-(2,5-difluoropheiiyl)pyrrolidin-1-yl)pyrazolo[1-a]pyrimidin-3-yl)-1H-pyrazol-4-yl)(morpholino)methanone (1-185)

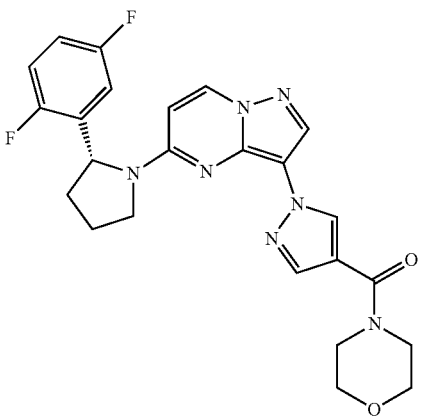 [SMILES: O=C(c1cnn(-c2cnn3ccc(N4CCC[C@@H]4c4cc(F)ccc4F)nc23)c1)N1CCOCC1]

(R)-(1-(5-(2-(2,5-difluorophenyl)pyrrolidin-1-yl)pyrazolo[1,5-a]pyrimidin-3-yl)-1H-pyrazol-4-yl)(morpholino)methanone

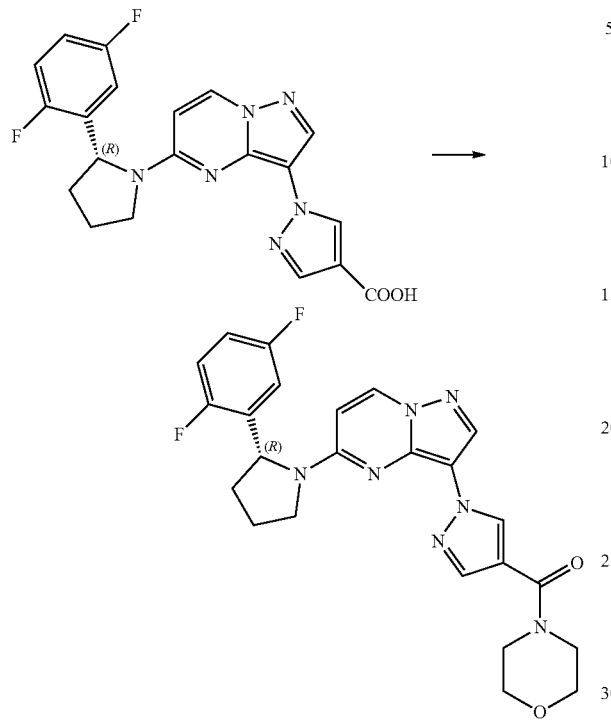

HATU (36 mg, 0.095 mmol) was added to a solution of (R)-1-(5-(2-(2,5-difluorophenyl)pyrrolidin-1-yl)pyrazolo[1,5-a]pyrimidin-3-yl)-1H-pyrazole-4-carboxylic acid (35 mg, 0.085 mmol), morpholine (11 uL, 0.126 mmol) and DIPEA (30 uL, 0.172 mmol) in THF (1.7 mL). The reaction mixture was stirred at room temperature for 16 h. The mixture was diluted with DCM then washed with water (1×) and with brine (1×), dried over MgSO4, filtered and concentrated under reduced pressure. The product was purified by reverse chromatography using 5-50% MeCN in AmFor 10 mM buffer to afford product as an off-white solid (15 mg, 37%) after lyophilisation. 1H NMR (400 MHz, DMSO) δ 8.81-8.68 (m, 1H), 8.65-8.54 and 8.06-7.98 (m, 1H), 8.34-8.18 (m, 1H), 7.96-7.89 and 7.84-7.75 (m, 1H), 7.40-6.91 (m, 3H), 6.71-6.60 and 6.14-6.02 (m, 1H), 5.51-5.31 (m, 1H), 4.07-3.97 (m, 1H), 3.79-3.52 (m, 9H), 2.58-2.39 (m, 1H), 2.13-1.83 (m, 3H); MS (m/z): 480.2 [M+1]+, >99%.

Example 17 (R)-1-(1-(5-(2-(2,5-Difluor® phenyl)pyrrolidin-1-yl)pyrazolo[1,5-a]pyrimidin-3-yl)-1H-pyrazol-4-yl)-N,N-dimethylmethanamine (I-186)

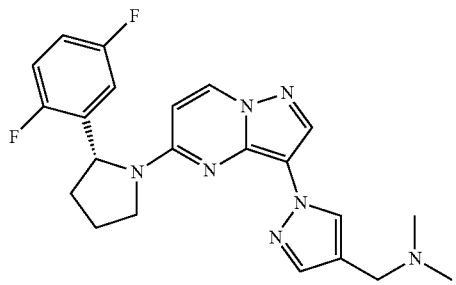 [SMILES: CN(C)Cc1cnn(-c2cnn3ccc(N4CCC[C@@H]4c4cc(F)ccc4F)nc23)c1]

(R)-1-(1-(5-(2-(2,5-difluorophenyl)pyrrolidin-1-yl)pyrazolo[1,5-a]pyrimidin-3-yl)-1H-pyrazol-4-yl)-N,N-dimethylmethanamine

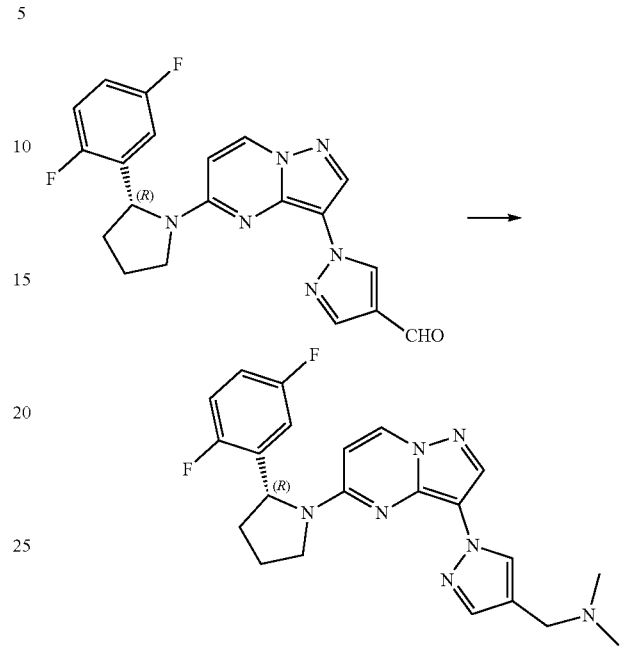

Sodium triacetoxyborohydride (120 mg, 0.566 mmol) was added to a solution of (R)-1-(5-(2-(2,5-difluorophenyl)pyrroiidin-1-yl)pyrazQ!o[1,5-a]pyrimidin-3-yl)-1H-pyrazole-4-carbaldehyde (74 mg, 0.188 mmol) and dimetliylamine (2M in THF, 0.11 mL, 0.22 mmol) in DCM (1 mL) at room temperature. The reaction mixture was then stirred for 2 h. Saturated aqueous NaHCO3 was added. The mixture was extracted with DCM (3×). Combined organic layers were dried over MgSO4, filtered and concentrated under reduced pressure. The product was purified by reverse chromatography using 5-40% MeCN in AmFor 10 mM buffer to afford product as a yellow solid (19 mg, 24%) after lyophilisation. 1HNMR (400 MHz, DMSO) δ 8.72 (d, J=7.4 Hz, 1H), 8.61-8.50 (m) and 7.69 (s) (1H) 8.42-8.30 (m) and 8.16 (s) (1H), 7.59-7.41 (m, 1H), 7.35-6.92 (m, 3H), 6.62 (d, j=7.5 Hz) and 6.09-5.98 (m) (1H), 5.51-5.28 (m, 1H), 4.08-3.96 (ray, 1H), 3.91-3.10 (m, 3H), 2.55-2.37 (m, 1H), 2.29-1.76 (m, 9H); MS (m/z): 424.2 [M+1]+, >99%.

Example 18 (R)—N-methyl-3-(4-methyl-1H-pyrazol-1-yl)-N-(1-phenylethyl)pyrazolo[1,5-a]pyrimidin-5-aniine (1-195)

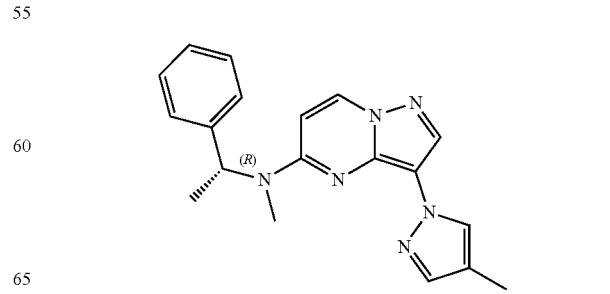

93

(R)-3-Iodo-N-(1-phenylethyl)pyrazolo[1,5-a]pyrimidin-5-amine

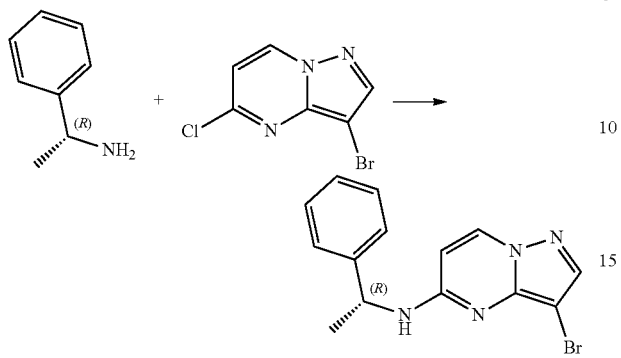

A mixture of 3-bromo-5-chloropyrazo!o[1,5-a]pyrimidine (150 mg, 0.645 mmol), (R)-1-phenethanamine (117 mg, 0.968 mmol) and DIPEA (0.450 mL, 2.581 mmol) in DMF (3.2 mL) was stirred at 110° C. for 4 h. Very clean profile by LCMS. The reaction mixture was directly added to a reverse phase chromatography for purification using 0-100% MeCN in AmF or buffer to afford title compound as a yellow solid.

(R)-3-bromo-N-methyl-N-(1-phenylethyl)pyrazolo[1,5-a]pyrimidin-5-amine

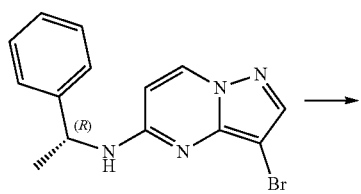

(R)-3-bromo-N-(1-phenylethyl)pyrazolo[1,5-a]pyrimidin-5-amine (135 mg, 0.426 mmol) was dissolved in THF to which NaH (11 mg, 0.468 mmol) was added. The reaction was stirred for 30 min at rt and MeI (0.03 mL, 0.468 mmol) was added. Additional NaH (102 mg, 4.256 mmol) followed by MeI (0.78 mL, 1.234 mmol) was added to the reaction mixture and this was stirred at rt for 18 h. The reaction mixture was directly added to a reverse phase chromatography for purification. The combined desired fractions were frozen and lyophilized to afford product as a yellow semi-solid substance.

94

(R)—N-methyl-3-(4-methyl-1H-pyrazol-1-yl)-N-(1-phenylethyl)pyrazolo[1,5-a]pyrimidin-5-amine

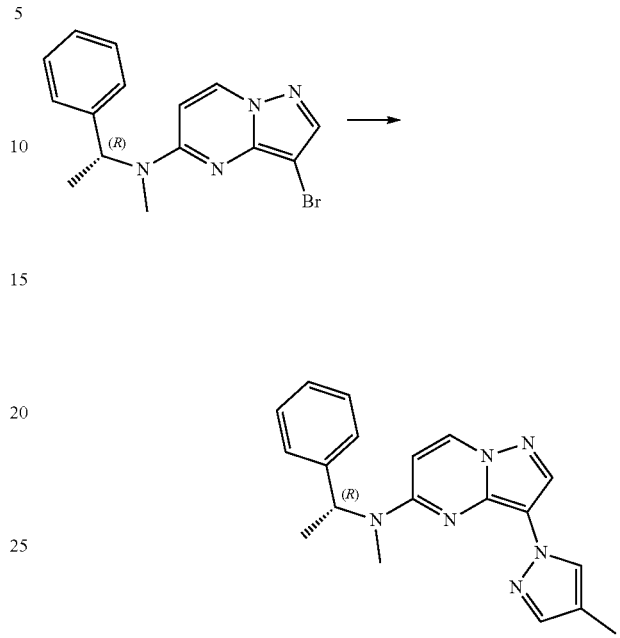

Prepared using procedure described in Example 001 using (R)-3-bromo-N-methyl-N-(1-phenylethyl)pyrazolo[1,5-a]pyrimidin-5-amine and 4-methyl-1H-pyrazole to afford title compound as a yellow solid (32 mg, 24%) after lyophilisation. 1H NMR (500 MHz, CDCl3) δ 8.30 (s, 1H), 8.25 (d, J=7.9 Hz, 1H), 8.07 (s, 1H), 7.45 (s, 1H), 7.40-7.27 (m, 5H), 6.33 id. I=7.9 Hz, 1H), 6.08 (br s, iH), 2.90 (s, 3H), 2.15 (s, 3H) 1.65 id. J=7.0 Hz, 3HK MS (m/z): 333.2 [M+1], >99%.

Example 19 (R)-3-(1-(5-(2-(2,5-difluorophenyl)pyrrolidm-1-yl)pyrazolo[1,S-aJpyrimidm-3-yl)-1H-pyrazol-4-yl)-1,1-dimethyliirea (1-197)

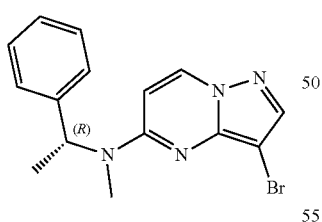

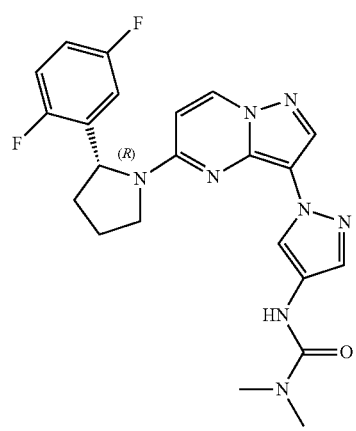

95

(R)-1-(5-(2-(2,5-difluorophenyl)pyrrolidin-1-yl)pyrazolo[J5-a]pyrimidin-3-yl)-1H-pyrazol-4-amine

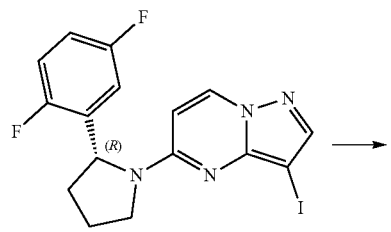

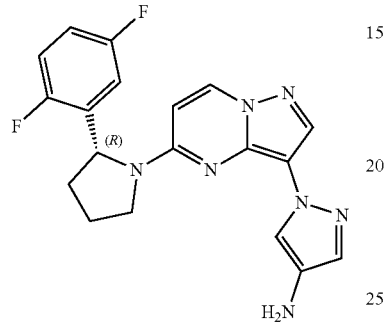

Prepared using procedure described in Example 001 using 1H-pyrazol-4-amine to afford title compound as a yellow oil (68 mg, 76%).

(R)-3-(1-5-(2-(2,5-difluorophenyl)pyrrolidin-1-yl)pyrazolo[1,5-a 1pyrimidin-3-yl)-1H-pyrazol-4-yl)-1-dimethylurea

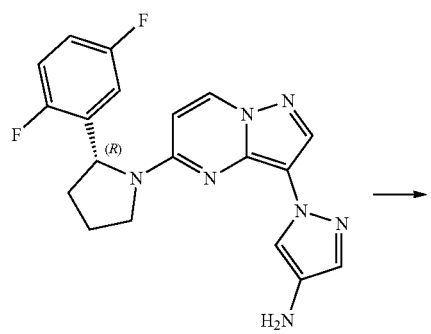

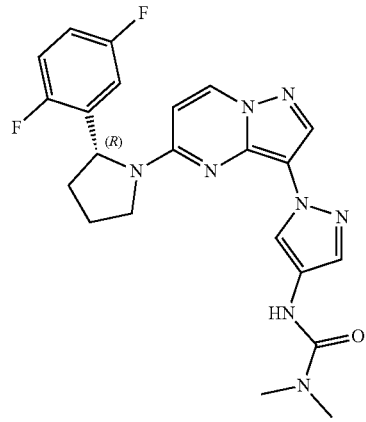

96

Dissolve (R)-1-(5-(2-(2,5-difluorophenyl)pyrrolidin-1-yl) pyrazolol 1,5-a]pyrimidin-3-yl)-!H-pyrazol-4-amine (34 mg, 0.076 mmol) and triethylamine (0.02 mL, 0.152 mmol) in anhydrous CH2C12 (0.8 mL) and add dropwise dimethylcarbamic chloride (40 uL, 0.455 mmol) to the mixture using a syringe. The mixture is stirred at rt for 48 h. The whole was concentrated and the product was purified by column chromatography using acetone in hexanes to afford a light brown solid (9 mg, 26%) after lyophihsation. 1H NMR (500 MHz, CDCl3) δ 8.26 (s, 1H), 8.15 (br s, 1H), 7.76-7.61 (m, 1H), 7.14-6.78 (m, 5H), 6.16 (s, 1H), 5.84 (br s, 1H), 5.33 (br s, i1-11. 4.14-3.90 (m, 2H), 3.07 (s, 6H), 2.58-2.47 (m, 1H), 2.16-1.91 (m, 3), MS (m/z): 453.3 [M+i]+, >97%.

Example 20 (R)—N-(1-(5-(2-(2,5-difluorophenyl)pyrrolidin-1-yl)pyrazolo[1,5-a]pyrimidin-3-yl)-1H-pyrazol-4-yl)-1,1-dimethylsulfonylurea (1-198)

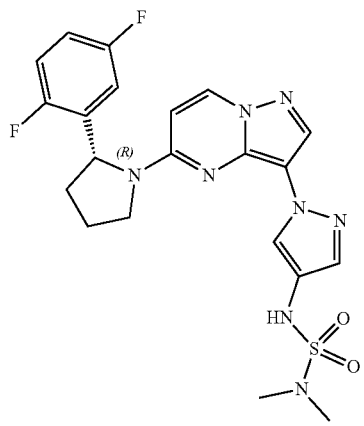

(R)—N-(1-(5-(2-(2,5 difluorophenyl)pyrrolidin-1-yl)pyrazolo[1,5-a]pyrimidin-3-yl)-1H-pyrazol-4-yl)-1,1dimethylsulfonylurea

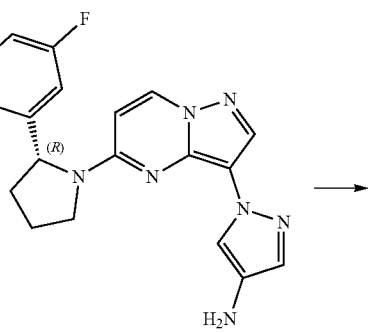

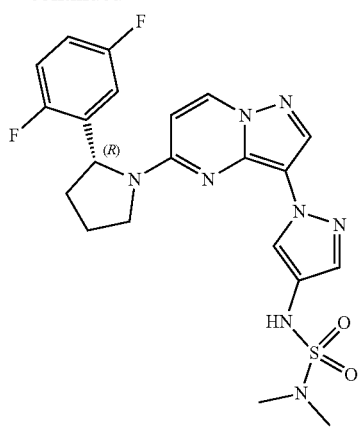

Prepared using procedure described in Example 019 using dimethylsuifamoyl chloride to afford title compound as a white solid (26.7 mg, 68%) after lyophihsation. 1H NMR (500 MHz, CDCl$_3$) δ 8.58 (br s, 0.5H), 8.33-8.09 (m, 2H), 7.86 (br s, 0.5H), 7.56 (s, 1H), 7.15-7.07 (m, 1H), 6.99-6.86 (m, 1H), 6.84-6.73 (m, 1H), 6.39-5.64 (m, 2H), 5.62-5.13 (m, 1H), 4.16-3.60 (m, 2H), 2.86 (s, 6H), 2.60-2.42 (m, 1H), 2.20-1.99 (m, 3H); MS (m/z): 489.3 [M+1]+, >97%.

Example 21. (R)-5-(2-(3,6-difluoropyridin-2-yl) pyrrolidin-1-yl)-3-(4-(5-methoxypyridin-3-yl)-11-1-pyrazol-1-yl)pyrazolo[1,5-a]pyrimidme (I-206)

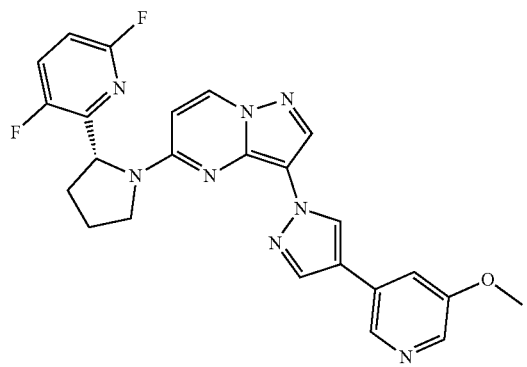 [SMILES: COc1cncc(-c2cnn(-c3cnn4ccc(N5CCC[C@@H]5c5nc(F)ccc5F)nc34)c2)c1]

(R)-5-(2-(3,6-difluoropyridin-2-yl)pyrrolidin-1-yl)-3-iodopyrazolofJ5-a]pyrimidine

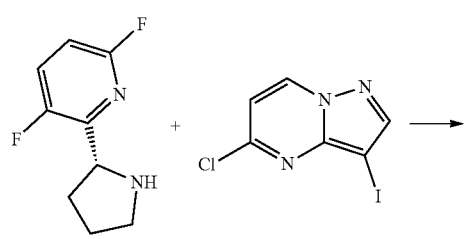

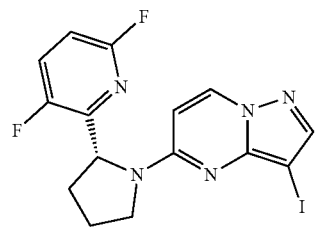

A mixture of (R)-3,6-difluoro-2-(pyrrolidin-2-yl)pyridme (10.3 g, 0.04 mol), 5-chloro-3-iodopyrazolo[1,5-a[pyrimidine (6.8 g, 0.04 mol) and DIPEA (26 mL, 0.15 mol) in DMF (370 mL) was stirred at 20° C. for 3 days. The mixture was slowly dropped into ice/water 1:1 (2L) and a solid was crashed out. The aqueous phase was extracted with EtOAc and washed 3× with water. The organic phase was dried over MgSO4, filtered and concentrated. Both residue were combined and purified by normal phase chromatography using a gradient of 0 to 15% acetone in hexane to afford title compound as off-white solid (11.2 g, 71%).

(R)-5-(2-(3,6-difluoropyridin-2-yl)pyrrolidin-1-yl)-3-(1H-pyrazol-1-yl)pyrazolo[J5-ajpyrimidine

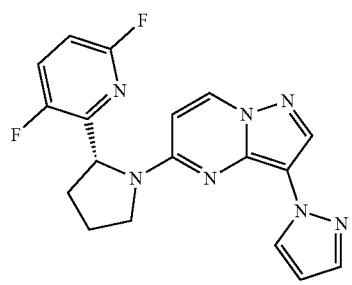

Prepared using procedure described in Example 001 using (R)-5-(2-(3,6-difluoropyridin-2-yl)pyrrolidin-1-yl)-3-iodopyrazolo[1,5-a]pyrimidine with 1H-pyrazole to afford title compound as a white solid (39 mg, 45%).

(R)-3-(4-bromo-1H-pyrazol-1-yl)-5-(2-(3,6-difluoro-pyridin-2-yl)pyrrolidin-1-yl)pyrazolo[1,5-a]pyrimidine

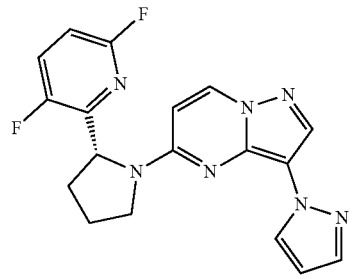

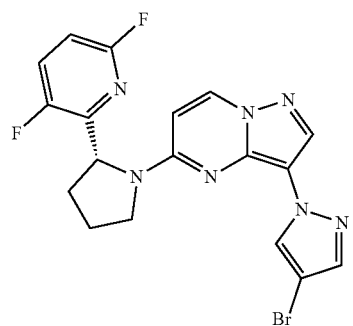

NBS (18.9 mg, 0.11 mmol) was added to a solution of (R)-5-(2-(3,6-difluoropyridin-2-yl)pyrrolidin-1-yl)-3-(1H-pyrazol-1-yl)pyrazolo[1,5-a]pyrimidine (39 mg, 0.11 mmol) in MeCN (3 mL). The mixture was stirred at room temperature for 2 h. The mixture was concentrated and the residue was purified by normal phase chromatography using a gradient of 0 to 60% acetone in hexanes to afford title compound as yellow' solid (45 mg, 95%).

(R)-5-(2-(3,6-difluoropyridine-2-yl)pyrrolidin-1-yl)-3-(4-(5-methoxypyridin-3-yl)-1H-pyrazol-1-yl)pyrazolo[1, 5-a]pyrimidine

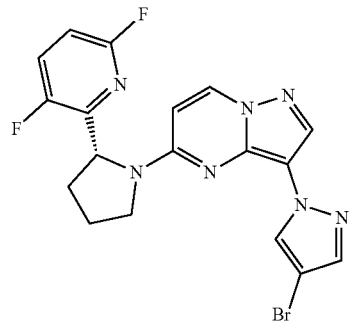

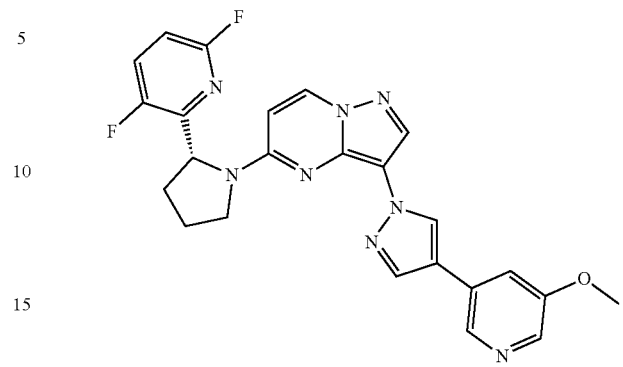

(R)-3-(4-bromo-1H-pyrazol-1-yl)-5-(2-3,6-difluoropyridin-2-yl)pyrrolidin-1-yl)pyrazolo[1,5-a]pyrimidine (26 mg, 0.06 mmol), $Cs_2CG3$ (57 mg, 0.17 mmol), Pd(dppf)Cl2.DCM (4.7 mg, 0.006 mmol) and 3-methoxy-5-(4,4,5,5-tetramethyl-1,3,2-dioxaborolan-2-yl)pyridine (21 mg, 0.09 mmol) charged in a sealed tube. Dioxane/water (5/1) (0.7 mL) degassed charged and reaction heated at 130° C. for 2 hour. The mixture was concentrated and purified by normal phase chromatography using a gradient of 0 to 100% acetone in hexanes and by prep HPLC using a gradient of 35 to 55% MeCN in 10 mM AmForm to afford title compound as white solid (10.8 mg, 39%) after lyophilisation. 1H NMR (500 MHz, CDCl3) δ 8.47 (s, 1H), 8.33 (s, 1H), 8.30 (s, 1H), 8.29-8.17 (m, 2H), 7.88 (s, 1H), 7.39 (s, 1H), 7.33-7.27 (m, 1H), 6.71-6.62 (m, 1H), 6.35-6.25 (m, 1H), 5.70 (s, 1H), 3.97 (s, 3H), 3.71 (s, 1H), 2.46 (s, 2H), 2.19-2.04 (m, 3H); MS (m/z): 475.2 [yI+I], >99%.

Example 22. 1-(1-(5-((II)-2-(2,5-diffliorophenyl)pyrrolidm-1-yl)pyrazolo[1,5-alpyrimidm-3-yI)-1II-pyrazol-4-yi)pyrrolidm-3-0 (1-208)

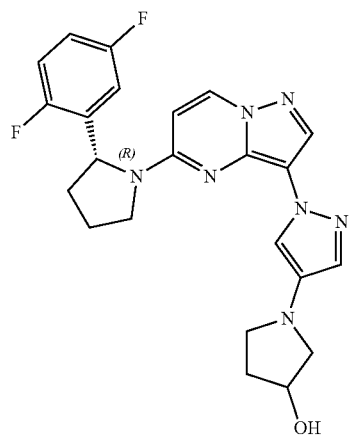

101

1-(1-(5-((R)-2-(2,5-difluorophenyl)pyrrolidin-1-yl)p}razolo[J5-a]pyrimidin-3-yl)-1H-pyrazol-4-yl)pyrrmhdin-3-ol

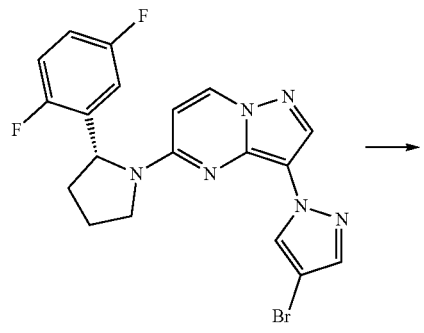

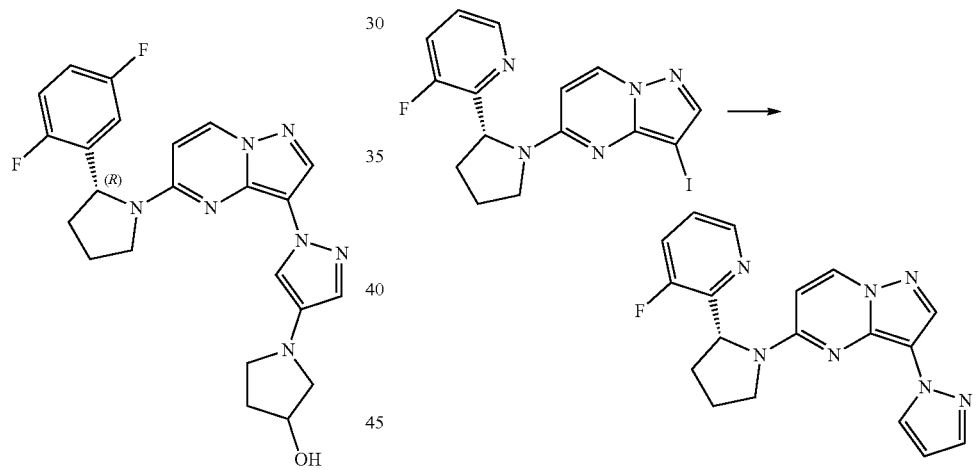

An oven-dried vial was charged with CuI (5 mg, 0.027 mmol), (R)-3-(4-bromo-1H-pyrazo]-1-yl)-5-(2-(2,5-difluorophenyl)pynOlidin-1-yl)pyrazolo[1,5-a]pyriniidine (20 mg, 0.045 mmol), K3PQ4 (29 mg, 0.135 mmol), DMPAO (8 mg, 0.040 mmol) and pyrrolidin-3-ol (16 mg, 0.180 mmol). The vial was evacuated and backfilled with N2, and DMSO (1 mL) was added. The reaction mixture was degassed for 5 min. The reaction is stirred at 100° C. for 36 h. The mixture was extracted with AcOEt and washed with water and brine, dried, and concentrated. The product was purified by column chromatography using 0-100% acetone in hexane. The product was concentrated and lyophilized from MeCN and water to afford desired compound as an off white solid (5.24 mg, 26%). 1H NMR (500 MHz, CDCl3) δ 8.40-8.05 (m, 2H), 7.90-7.38 (m, iH), 7.16-6.64 (m, 4H), 6.45-4.99 (m, 2H), 4.62-3.54 (m, 4H), 3.47-2.77 (m, 2H), 2.58-2.25 (m, 2H), 2.25-1.93 (m, 5H); MS (m/z): 452.2 [Mt 1], >99%.

102

Example 23. 1-(i-(5-((R)-2-(3-fluoropyridin-2-yl)pyrrolidin-1-yl)pyrazolo[1,5-a]pyrimidin-3-yl)-1H-pyrazol-4-yl)pyrrolidin-3-ol (1-209)

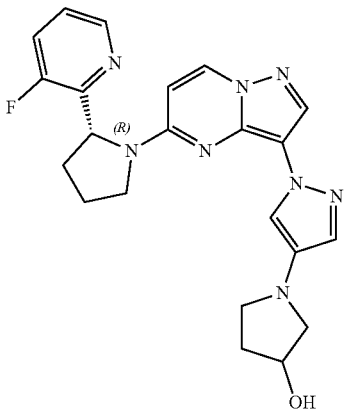

(R)-5-(2-(3-fluoropyridin-2-yl)pyrrolidin-1-yl)-3-(1H-pyrazol-1-yl)pyrazolo[1,5-a]pyrimidine Prepared using procedure described in Example 014 using 1H-pyrazole to afford title compound as a beige solid (115 mg, 54%).

(R)-3-(4-bromo-1H-pyrazol-1-yl)-5-(2-(3-fluoropyridin-2-yl)pyrrolidin-1-yl)pyrazolo[J5-a]pyrimidine

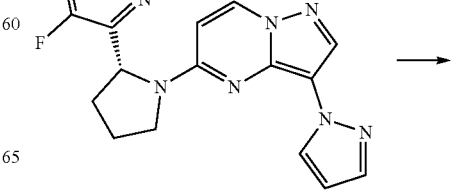

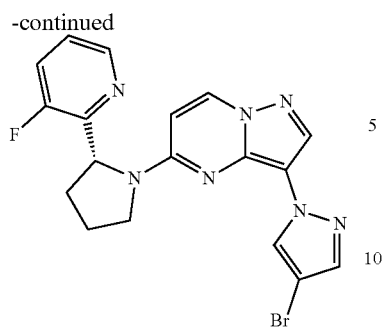

NBS (58 mg, 0.326 mmol) was added to a solution of (R)-5-(2-(3-fluoropyridin-2-yl)pyrrolidin-1-yl)-3-(1H-pyrazol-1-yl)pyrazolo[1,5-a]pyrimidine (110 mg, 0.315 mmol) in MeCN (3 mL). The mixture was stirred at room temperature for 2 h. The reaction mixture was diluted with EtOAc then washed with saturated aqueous sodium bisulfite and with water/brine (1:1), dried over MgSO4, filtered and concentrated under reduced pressure. The product was purified by normal chromatography using 30-100% AcOEt in hexanes to afford product as an off-white solid (81 mg, 60%).

1-(i-(5-((R)-2-(3~fluoropyridin-2-yl)pyrrolidin-1~yl) pyrazolo[J5-a]pyrimidin-3-yl)-1H-pyrazol-4-yl)pyrrolidin-3-ol

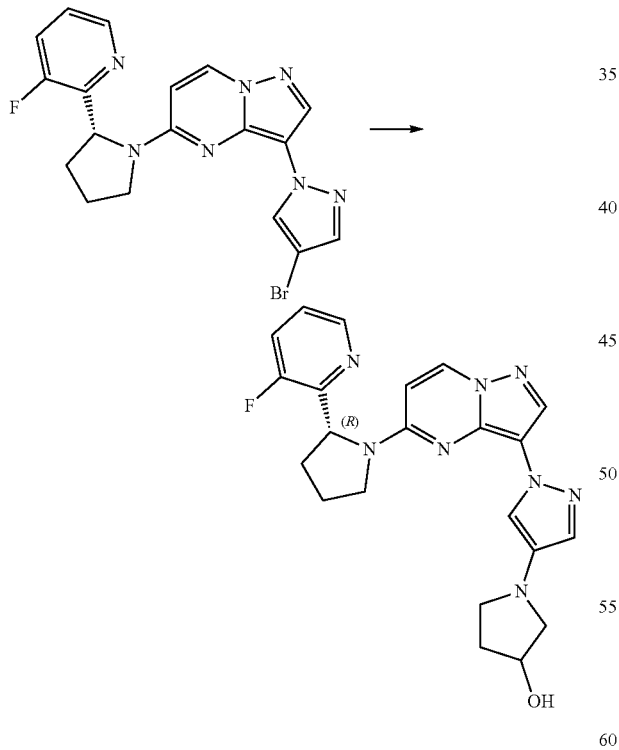

Prepared using procedure described in Example 022 from (R)-3-(4-bromo-1H-pyrazol-1-yl)-5-(2-(3-fluoropyridin-2-yl)pyrrolidm-1-yl)pyrazolo[1,5-a]pyrimidine to afford title compound as a yellow solid (5.4 mg, 36%) after lyophilisation. 1H NMR (500 MHz, CDCl3) δ 8.38-7.93 (m, 3H), 7.63-7.27 (m, 2H), 7.23-7.07 (m, 2H), 6.37-6.15 (m, 1H), 5.88-5.56 (m, 1H), 4.63-4.52 (m, 1H), 4.15-3.57 (m, 3H), 3.47-3.38 (m, 1H), 3.31-3.24 (m, 1H), 3.24-3.17 (m, 1H), 3.11-3.00 (m, 1H), 2.57-2.43 (m, 1H), 2.36-2.25 (m, I=6.6 Hz, 2H), 2.19-1.99 (m, 3H); MS (m/z): 435.3 [M+1]+, >99%.

Example 24. (R)-5-(2-(2,5-difluorophenyl)pyrrolidin-1-yl)-3-(4-(5-(oxetan-3-yloxy)pyridin-3-yl)-1H-pyrazol-1-yl)pyrazolo[1,5-a]pyrimidine (1-214)

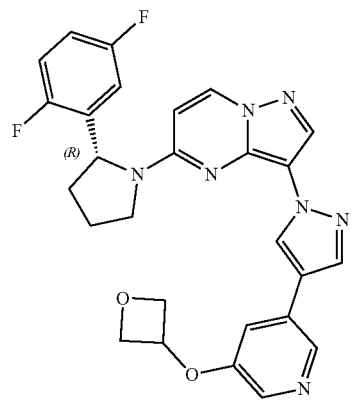

(R)-5-(2-(2,5-difluorophenyl)pyrrolidin-1-yl)-3-(4-(5-(oxetan-3-yloxy)pyridin-3-yl)-1H-pyrazol-1-yl) pyrazolo[L5-a]pyrimidine To a solution of (R)-5-(2-(2,5-difluorophenyl)pyrrolidin-1-yl)-3-(4-(5-methoxypyridin-3-y])-1H-pyrazol-1-y])pyrazolo[1,5-a]pyrimidine (10 mg, 0.02! mmol) in DCM (0.5 ml) at −78° C. was added a solution of BBr3 in DCM 1M (30 uL, 0.030 mmol). The mixture was warmed ON to rt and was stirred 7 days at the same temperature to achieve 70% of conversion. The reaction was diluted with methanol and stirred ON at rt. Next morning, the reaction was concentrated and the residue was used without further purification. To a solution of the above (R)-5-(1-(5-(2-(2,5-difluorophenyl)pyrrolidin-1-yl)pyrazolo[1,5-a]pyrimidin-3-yl)-1H-pyrazol-4-yl)pyridin-3-ol (9.7 mg, 0.02 mmol) in DMF (2 mL) was added K2CQ3 (60 mg, 0.44 mmol) and 3-iodooctane (20 uL, 0.05 mmol). The mixture was stirred at 150° C. for Ih in an oil bath. The mixture was diluted with EtOAc and washed 3 times with water; the organic phase was dried over MgSO4, filtered and concentrated. The residue was purified by normal flash chromatography using a gradient of 10 to 100% acetone in hexanes and by prep HPLC using a gradient of 35 to 55% MeCN in 10 mM AmForm to afford title compound as off-shite solid (1.1 mg, 10%) after !yophi!ization. 1HNMR (500 MHz, CDCl$_3$) δ 8.89-8.10 (m, 4H), 8.00-7.78 (m, 2H), 7.23-7.12 (m, 1H), 7.12-7.01 (m, 1H), 6.97-6.81 (m, 6.79-6.67 (m, 1H), 6.43-6.13 (m, 1H), 5.94-5.56 (m, 1H), 5.40-5.30 (m, 1H), 5.05 (t, J=6.7 Hz, 2), 4.88-4.81 (m, 2H), 4.08-3.61 (m, 2H), 2.58-2.46 (m, 1H), 2.26-2.01 (m, 3H); MS (m/z): 516.1 [M+1+j+, >99%.

Example 25. (R)-5-(2-(3-fluoro-6-methoxypyridin-2-yl)pyrrolidin-1-yl)-3-(4-methyl-1H-pyrazoI-1-yl)pyrazolo[1,5-a]pyrimidine (1-216)

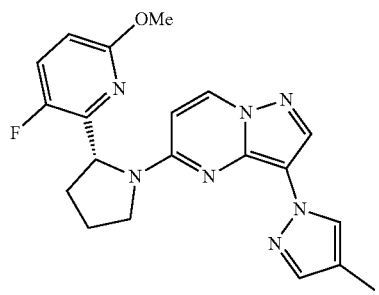

(R)-5-(2-(3-fluoro-6-methoxypyridin-2-yl)pyrrolidin-1-yl)-3-(4-methyl-1H-pyrazol-1-yl)pyrazolo[1,5-a]pyrimidine

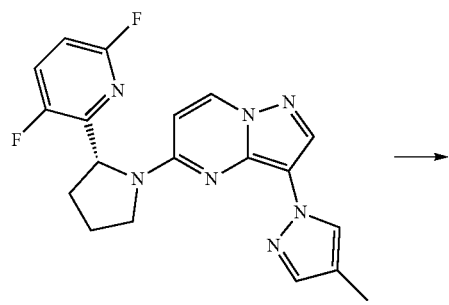

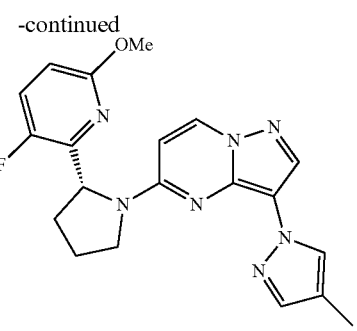

In a vial was added MeOH (1 niL to which was added Na metal (8 mg). Tins was stirred under N2 until a clear solution. A 0.25 mL aliquot of the solution was added to (R)-5-(2-(3,6-difluoropyridin-2-yl)pyrrolidin-1-yl)-3-(4-methyl-1H-pyrazol-1-yl)pyrazolo[1,5-a]pyrimidine (16.7 mg, 0.044 mmol) in MeOH (1 mL) and the mixture is stirred at 100° C. over 2 d. The whole was concentrated and the product was eluted on normal flash chromatography using acetone in hexane and by reverse chromatography using 0-100% MeCN in AmFor. Product was lyophilized to afford title compound (7.28 mg, 42%) as an off-white solid. 1H NMR (500 MHz, CDCT3) δ 8.28-8.14 (m, 2H), 8.10-7.86 (m, 1H), 7.46-7.36 (m, 1H), 7.33-7.27 (m, iH), 6.66-6.48 (m, 1H), 6.30-5.91 (m, iH), 5.73-5.20 (m, iH), 4.09-3.76 (m, 2H), 3.74 (s, 3H), 2.60-2.36 (m, 2H), 2.23-2.04 (m, 5H), MS (m/z): 394.2 [M+i]+. >99%.

Example 26 (R)-5-fluoro-N,N-dimethyl-6-(1-(3-(4-methyl-1H-pyrazol-1-yl)pyrazolo[1,5-a]pyrimidin-5-yl)pyrrolidm-2-yl)pyridin-2-amine (1-217)

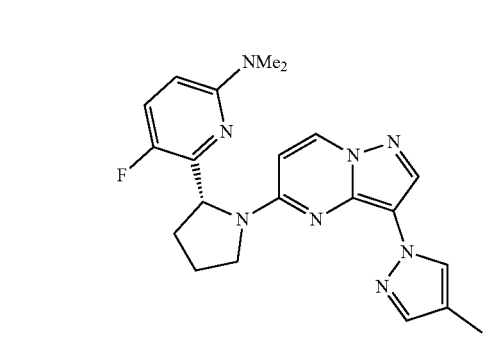 [SMILES: COc1ccc(F)c([C@H]2CCCN2c2ccn3ncc(-n4cc(C)cn4)c3n2)n1]

(R)-5-fluoro-N,N-dimethyl-6-(1-(3-(4-methyl-1H-pyrazol-1-yl)pyrazolo[1,5-a]pyrimidin-5-yl)pyrrolidin-2-yl)pyridin-2-amine

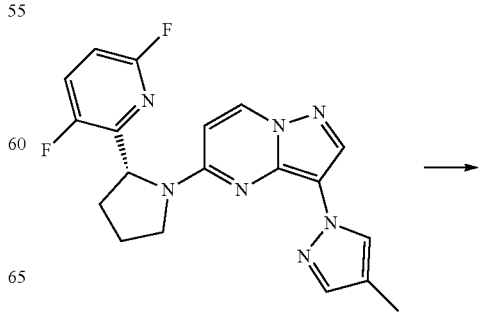

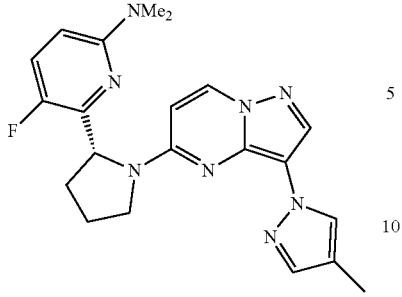

In a vial was added (R)-5-(2-(3,6-difluoropyridin-2-yl)pyrrolidin-1-yl) (4-methyl-1H-pyrazol-1-yl)pyrazolo[1,5-a]pyrimidine (16.7 mg, 0.044 mmol) in DMF (1 mL) to which was added dimethylamine (2M, 0.05 mL, 0.096 mmol). This was stirred under $N_2$ at 140° C. overnight. The whole was directly added to a reverse chromatography column and the product purified using 0-100% MeCN in AmFor. Product was lyophilized to afford an off-white solid (14 mg, 79%). 1H NMR (500 MHz, CDCl3) δ 8.26-8.14 (m, 2H), 8.06-7.94 (m, M1), 7.47-7.36 (m, 1H), 7.21-7.14 (m, 1H), 6.36-6.20 (m, 1H), 6.02-5.95 (m, 0.3H), 5.72-5.63 (m, 0.7H), 5.22-5.16 (m, 0.3H), 4.05-3.67 (m, 2H), 2.92 (s, 6H), 2.58-2.29 (m, 2H), 2.24-2.02 (m, 5H); MS (m/z): 407.3 [M+1]+, >99%.

Example 027 (R)-5-(2-(2,5-difluorophenyl)pyrrolidin-1-yl)-3-(4-(6-fluoropyridin-3-yl)-1H-pyrazol-1-yl)pyrazolo[1,5-a]pyrimidine (I-219)

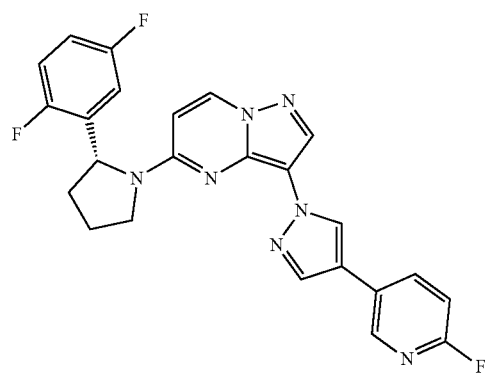

(R)-5-(2-(2,5-difluorophenyl)pyrrolidin-1-yl)-3-(4-(6-fluoropyridin-3-yl)-1H-pyrazol-1-yl]pyrazolo[1,5-a]'pyrimidine

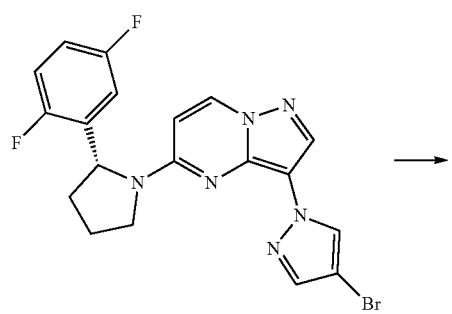

→

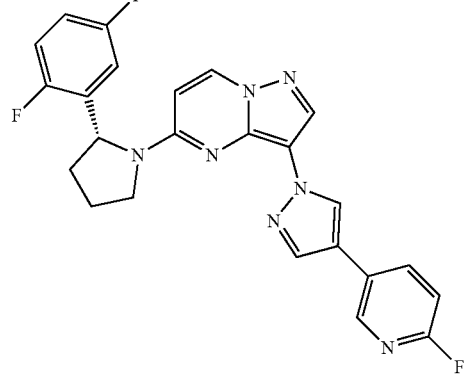

A mixture of (R)-3-(4-bromo-1H-pyrazol-1-yl)-5-(2-(2,5-difluorophenyl)pynOlidm-1-yl)pyrazolo]1,5-a]pyrimidine (100 mg, 0.225 mmol), (6-fluoropyridin-3-yl)boronic acid (71 mg, 0.449 mmol), Pd(PPh3)4 (26 mg, 0.022 mmol) and Na2C03 (71 mg, 0.674 mmol) was stirred under atmosphere of N2 and in degassed solution of dioxane and water (4:1; 2 mL) at 100° C. for 18 h. The mixture was diluted with EtOAc, washed with water dried over MgSG4, filtrated and concentrated. The residue was purified by normal phase chromatography using a gradient of 0 to 100% acetone in hexanes and then purified by reverse chromatography using 0-100% MeCN in AmFor 10 mM buffer and the product was iyophilized to dryness. The product was isolated as an off-white solid (57.2 mg, 55%). 1–1=1 NMR (500 MHz, CDCl3) δ 8.91-7.71 (m, 6H), 7.16-6.67 (m, 4H), 6.44-5.82 (m, 1H), 5.75-5.13 (m, 1H), 4.15-3.60 (m, 2H), 2.60-2.42 (m, 1H), 2.21-1.98 (m, 3H); MS (m/z): 462.3 [M+1]+, >96%.

Example 28. (R)—N-(1-(2,5-Difluor® phenyfl-ethyl)-3-(4-(6-methoxypyridin-3-yl)-1H-pyrazol-1-yl)pyrazolo[1,5-a]pyrimidin-5-amine (1-220)

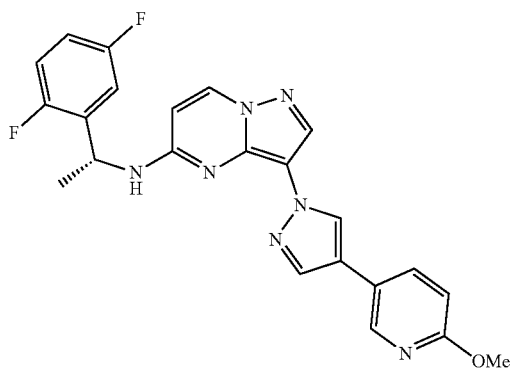 [SMILES: COc1ccc(-c2cnn(-c3cnn4ccc(N[C@H](C)c5cc(F)ccc5F)nc34)c2)cn1]

(R)-(2,5-difluorophenyl)ethanamine

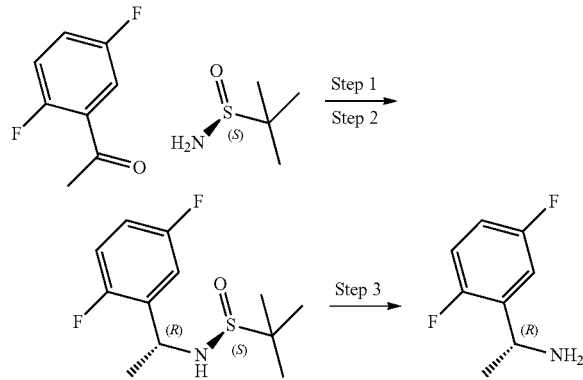

Step 1: In a RBF containing the 1-(2,5-difluorophenyl) ethanone (910 mg, 5.828 mmol) under nitrogen at room temperature was added THF (14 mL) followed by (S)-2-methylpropane-2-sulfinamide (1060 mg, 8.743 mmol) and titanium ethoxide (1.83 mL, 8.743 mmol). Mixture stirred in a 70° C. oil bath for 20 h and the reaction was followed by TLC and LCMS. The flask was cooled with icy-water bath and saturated aqueous NH₄Cl added (250 mL, white solid formation); diluted with EtOAc, sonicated and solid was removed by filtration. Filtrate diluted in EtOAc, washed with water and brine. Organic layer was dried over MgSO4, filtered and solvent evaporated to give as yellow oil (1.45 g).

Step 2: (S,E)-N-(1-(2,5-di fluorophenyl)ethylidene)-2-methylpropane-2-sulfamide (1470 mg, 3.401 mmol) was dissolved in THF (13 mL) under nitrogen in a round bottom flask. Mixture cooled at −78° C. and slowly Super-H (4.1 mL, 4.08 mmol) was added dropwise (temperature never reach higher that −70° C.). Mixture stirred at -78° C. After 2 hour, LCMS showed complete conversion to what seems to be only 1 product. The mixture was quenched with NH4C1 sat. and extracted with AcOEt. The crude material (1.63 g) was used such as in next step. NMR analysis showed a 10.2:1 ratio of diastereoisomers (dr).

Step 3: To a solution of (S)—N—((R)-1-(2,5-difluorophenyl)ethyl)-2-methyipropane-2-sulfinamide (1638 mg, 6.268 mmol) in methanol (30 mL) was added HCl (6.3 mL, 25 mmol) (4N in dioxane). The mixture was stirred 60 min at 0° C. and it was concentrated. The whole was partitioned between HCl 1N and AcOEt and the aqueous layer w' as collected. The organic layer was extracted 3 times with HCl 1M. The combined aqueous layers were basified with NH₄OH and the whole was extracted with fresh AcOEt. The combined organic layers were dried (MgSO4) and concentrated to afford (R)-1-(2,5-difluorophenyl)ethanamine as a yellow oil (990 mg, 90% overall in 3 setps).

(R)—N-(1-(2,5-difluorophenyl)ethyl)-3-iodopyrazolo[J 5-a]pyrimidin-5-amine

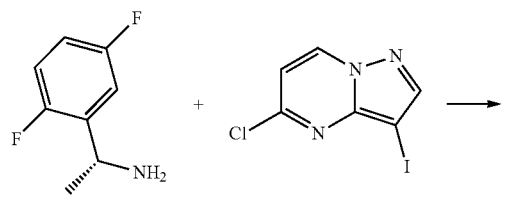

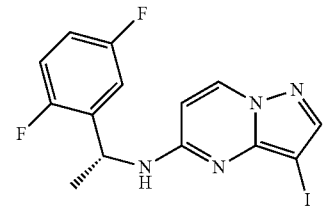

Prepared using procedure described in Example 001 from (R)-1-(2,5-difluorophenyl)ethanamine and 5-chloro-3-iodopyrazolo[1,5-a]pytimidine to afford title compound as an orange oil (713 mg, 33%).

(R)—N-(1-(2,5-difluorophenyl)ethyl)-3-iodopyrazolo[J 5-a]pyrimidin-5-amine

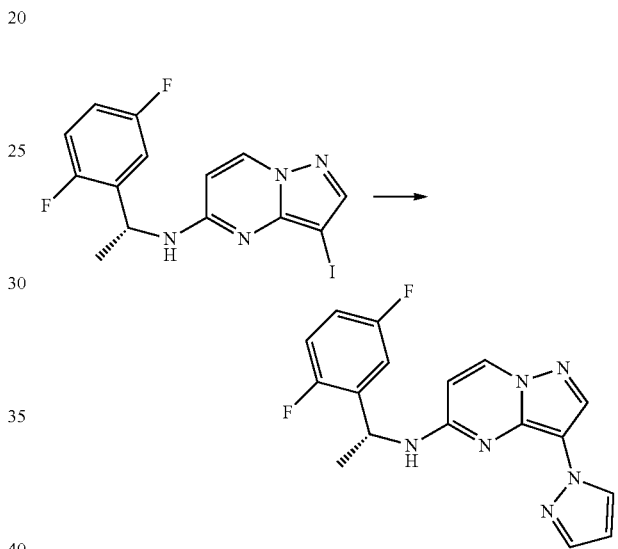

Prepared using procedure described in Example 001 from (R)-1-(2,5-difluorophenyl)ethanamine and 5-chloro-3-iodopyrazolo[1,5-a]pyrimidine to afford title compound as an orange oil (713 mg, 33%).

(R)-3-(4-bromo-1H-pyrazol-1-yl)-N-(1-(2,5-difiuorophenyl)ethyl)pyrazolo[J5-aJpyrimidin-5-amine

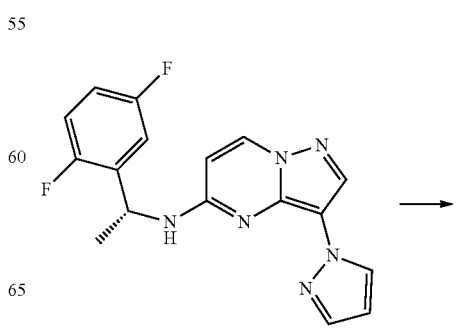

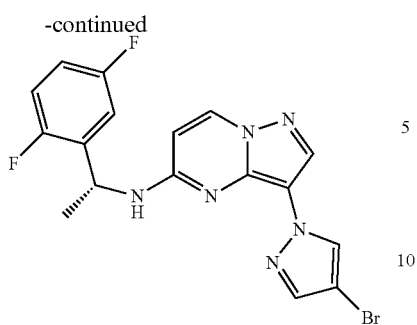

NBS (80 mg, 0.448 mmol) was added to a solution of (R)—N-(1-(2,5-difluorophenyl)ethyl)-3-(1H-pyrazol-1-yl)pyrazolo[1,5-a]pyrimidin-5-amine (139 mg, 0.408 mmol) in MeCN (4 mL). The mixture was stirred at room temperature for 1 h. LCMS indicated complete conversion. The mixture was concentrated and the residue was purified by normal phase chromatography using a gradient of 0 to 100% acetone in hexanes to afford title compound as yellow solid (181 mg, 100%).

(R)—N-(1-(2,5-difluorophenyl)ethyl)-3-(4-(6-methoxypyridin-3-yl)-1H-pyrazol-1-yl)pyrazolo[45-a]pyrimidin-5-amine

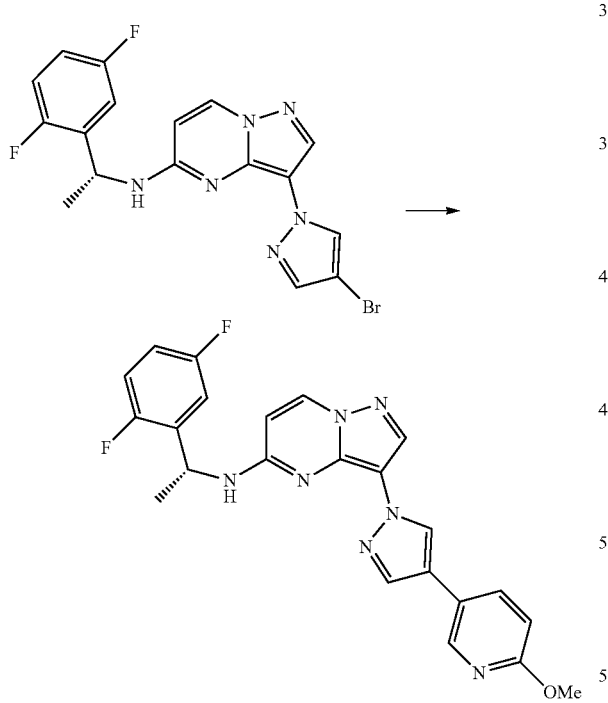

Prepared using procedure described in Example 027 from (R)-3-(4-bromo-1H-pyrazol-1-yl)-N-(1-(2,5-difluorophenyl)ethyl)pyrazolo[1,5-a]pyrimidin-5-amine and using 2-metboxy-5-(4,4,5,5-tetrametbyl-1,3,2-dioxaborolan-2-yl)pyridine to afford title compound as an off-white solid (12.0 mg, 28%) after lyophilisation. 1H NMR (500 MHz, CDCl3) δ 8.39 (d, J=2.3 Hz, 1H), 8.33 (s, 1H), 8.31 (s, 1H), 8.21 (d, J=7.6 Hz, 1H), 7.83 (s, 1H), 7.76 (dd, J=8.5, 2.5 Hz, 1H), 7.03 (ddd, J=8.8, 5.8, 3.1 Hz, 1H), 6.95 (td, J=9.3, 4.4 Hz, iH), 6.89-6.85 (m, 1H), 6.83 (d, J=8.5 Hz, 1H), 6.12 id. J=7.6 Hz, 1H), 5.49-5.39 (m, 1H), 5.38-5.31 (m, 1H), 4.00 (s, 3H), 1.61 (d, J=6.9 Hz, 3H); MS (m/z): 448.3 [M+1]+, >99%.

Example 29. (R)-5-(2-(3,6-difluoropyridin-2-yl)pyrrolidin-1-yl)-3-(4-(6-methoxypyridin-3-yl)-1H-pyrazol-1-yl)pyrazolo[1,5-a]pyrimidine (1-221)

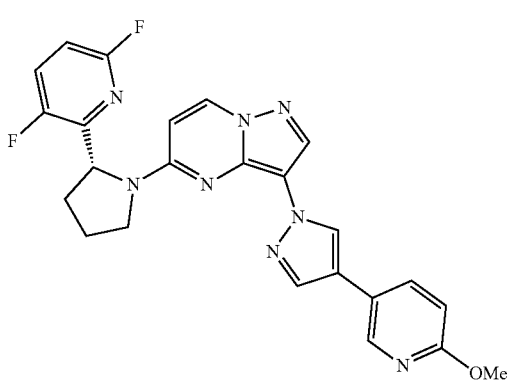 [SMILES: COc1ccc(-c2cnn(-c3cnn4ccc(N5CCC[C@@H]5c5nc(F)ccc5F)nc34)c2)cn1]

(R)-5-(2-(3,6-difluoropyridin-2-yl)pyrrolidin-1-yl)-3-(4-iodo-1H-pyrazol-1-yl)pyrazolo[1,5-a]pyrimidine

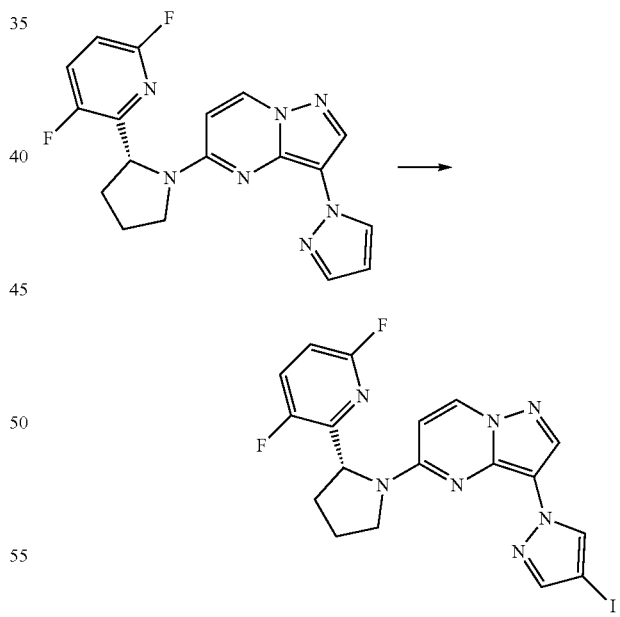

NIS (18.9 mg, 0.11 mmol) was added to a solution of (R)-5-(2-(3,6-difluoropyridin-2-yl)pyrrolidin-1-yl)-3-(1H-pyrazol-1-yl)pyrazolo[1,5-ajpyrimidine (39 mg, 0.11 mmol) in MeCN (3 mL). The mixture was stirred at room temperature for seven days. The mixture was concentrated and the residue was purified by normal phase chromatography using a gradient of 10 to 60% acetone in hexanes to afford title compound as yellow solid (157 mg, 44%).

113

(R)-5-(2-(3,6-difluoropyridin-2-yl)pyrrolidin-1-yl)-3-(4-(6-methoxypyridin-3-yl)-1H-pyrazol-1-yl)pyrazolo[1,5-a]pyrimidim

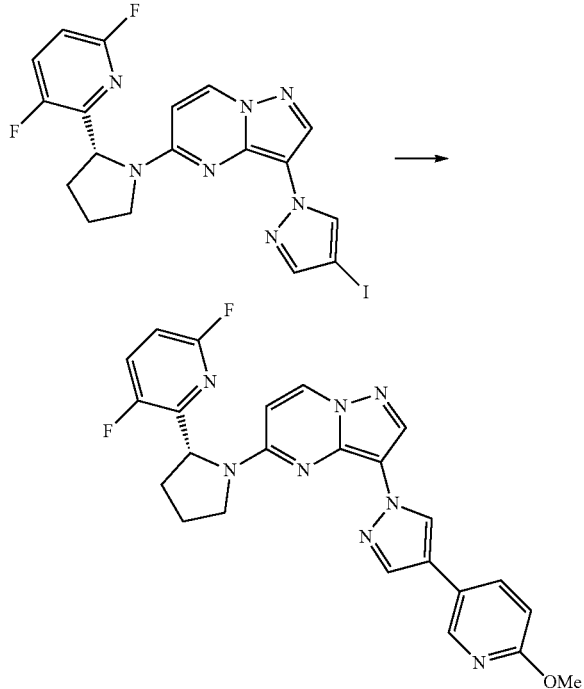

Prepared using procedure described in Example 027 from (R)-5-(2-(3,6-difluoropyridin-2-yl)pyrrolidin-1-yl)-3-(4-iodo-1H-pyrazol-1-yl)pyrazolo[1,5-a]pyrimidine and 2-methoxy-5-(4,4,5,5-tetramethyl-1,3,2-dioxaborolan-2-yl)pyridine to afford title compound as an off-white solid (6.68 mg, 19%). 1H NMR (500 MHz, DMSO) δ 8.78-8.68 (m, 1H), 8.58-8.44 (m, 1H), 8.29-8.23 (m, 1H), 8.23-8.17 (m, 1H), 8.06-7.98 (m, 1H), 7.94-7.86 (m, 1H), 7.64-7.55 (m, 1H), 7.03-6.97 (m, 1H), 6.97-6.91 (m, 1H), 6.67-6.59 (m, 1H), 5.62-5.56 (m, 1H), 3.91 (s, 3H), 3.87-3.83 (m, 1H), 3.78-3.71 (m, 2H), 2.26-2.18 (m, 1H), 2.13-2.05 (m, 1H), 2.00-1.93 (m, 1H): MS (m/z): 475.3 jM+1]+, >99%.

Example 30 (R)-5-(2-(2,5-difluorophenyi)pyrroiidin-1-yl)-3-(4-(6-(oxetan-3-yloxy)pyridm-3-yl)-1H-pyrazol-1-yl)pyrazolo[1,5-a]pyrinildine (I-223)

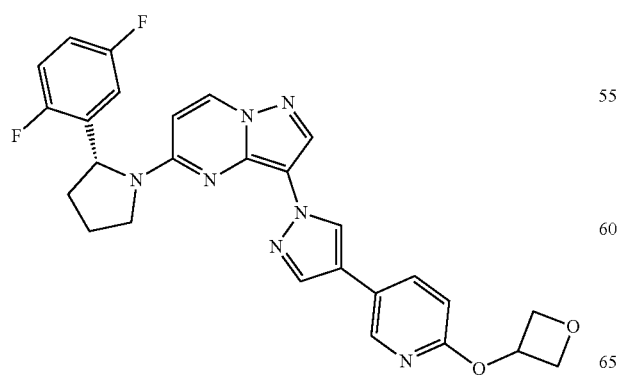

114

2-(oxetan-3-yloxy)-5-(4,4,5,5-tetramethyl-1,3,2-dioxaborolan-2-yl)pyridine

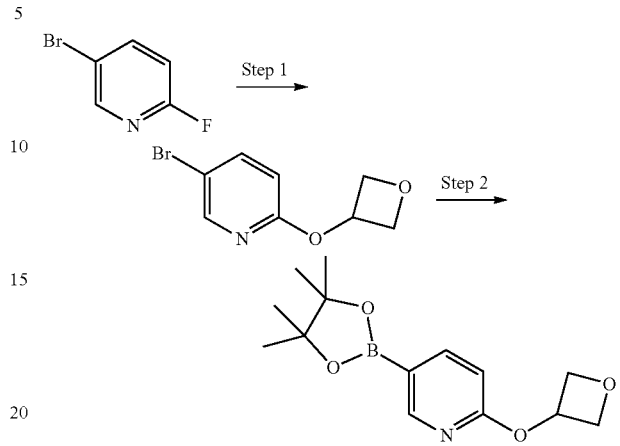

Step 1: To oxetan-3-ol (1.26 g, 17.046 mmol) in DMF (30 mL) under nitrogen at 25° C. was added sodium hydride (60%, 727 mg, 18.183 mmol) portion-wise over 5 minutes. The reaction was stirred for 1 hour and a solution of 5-bromo-2-fluoropyridine (2 g, 11.364 mmol) in DMF (25 mL) was added over 10 minutes. The resulting mixture was heated at 130° C. for 5 hours and cooled to 25° C. and stirred until the next morning. The mixture was diluted with ether and washed with water and brine. The organic layer was dried (MgSO4), filtered, and concentrated to provide slightly over 2.6 g of the title compound (considered 100%) as yellow solid.

Step 2: Tb a solution of 5-bromo-2-(oxetan-3-yloxy)pyridine (1.626 g, 7.068 mole) in anhydrous THF (24 ml) was added dropwise n-BuLi (3.11 mL, 2.5M in THF) at −78° C., the resulting mixture was stirred for 1 h. 2-Isopropoxy-4,4,5,5-tetramethyl-1,3,2-dioxaboro!ane (1.8 mL, 8.835 mmol) was added at −78° C. and the reaction mixture was warmed to room temperature and continued to stir for 2 h. The mixture was quenched with sat NH4Cl and extracted with AcOEt and the organic layer was dried and concentrated to afford product as a slight yellow' oil which was used such as.

(R)-5-(2-(2,5-difluorophenyl)pyrrolidm-1-yl)-3-(4-(6-(oxetan-3-yloxy)pyridin-3-yl)-1H-pyrazol-1-y)pyrazolo[1,5-a]pyrimidine

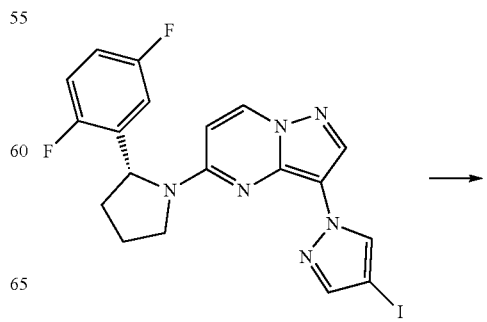

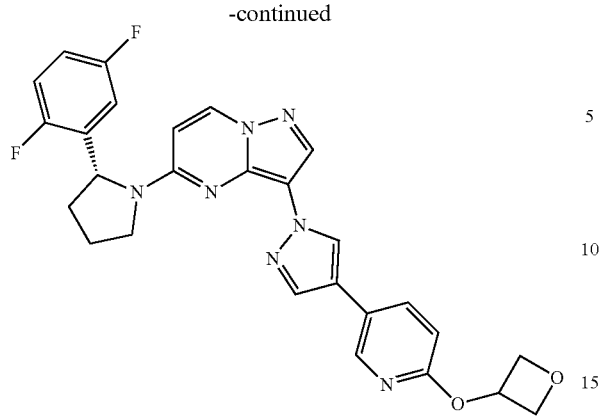

Prepared using procedure described in Example 027 from (R)-5-(2-(2,5-difluoropheny!)pyrrolidin-1-y!)-3-(4-iodo-1H-pyrazoS-1-yl)pyrazolo[1,5-a]pyrimidine and 2-(oxetan-3-yloxy)-5-(4,4,5,5-tetramethyl-L3,2-dioxaborolan-2-yl) pyridine to afford title compound as a yellow solid (468.3 mg, 22%) after !yophi!ization. 1H NMR (400 MHz, CDCl3) δ 8.64 (br s, Q.5H), 8.43-8.01 (m, 3.5H), 7.88-7.62 (m, 2H), 7.13-6.80 (m, 3H), 6.77-6.68 (m, 1H), 6.34 (br s, 0.5H), 5.73-5.59 (m, 1H), 5.04 (t, j=6.8 Hz, 2H) 4.83-4.73 (m, 2H), 4.20-3.55 (m, 2H), 2.50 (s, 1H), 2.20-1.99 (m, 3H); MS (m/z): 516.4 [M+1]+. 95%.

Example 31 (R)-1-(1-(5-(2-(2,5-dilluorophenyl) pyrrolidm-1-yI)pyrazolo[1,S-a]pyrimidm-3-yl)-1H-pyrazoI-4-yl)etliano5ie (I-225)

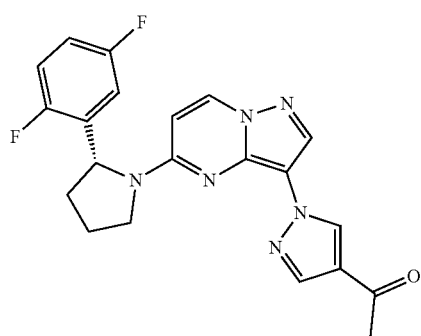 [SMILES: CC(=O)c1cnn(-c2cnn3ccc(N4CCC[C@@H]4c4cc(F)ccc4F)nc23)c1]

(R)-1-(1-(S-(2-(2,5-difluorophenyl)pyrrolidin-1-yl) pyrazolo[1,5-a]pyrimidin-3-yl)-1H-pyrazol-4-yl) ethanone

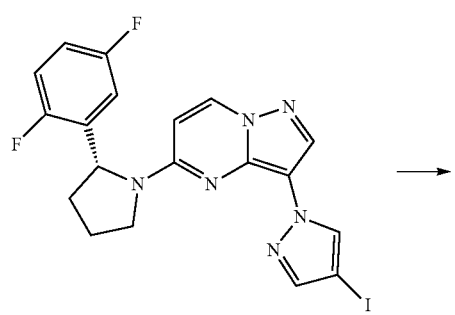

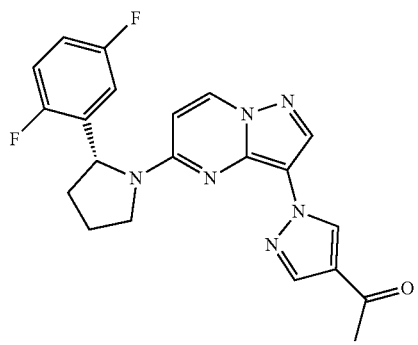

A mixture of (R)-5-(2-(2,5-difluorophenyl)pyrrolidin-1-yl)-3-(4-iodo-1H-pyrazol-1-yl)pyrazolo[1,5-a]pyrimidine (40 mg, 0.081 mmol), tributyl(1-ethoxyvinyl)stannane (32 mg, 0.089 mmol), Pd(PPh3)4 (3 mg, 0.008 mmol) in dioxane was reacted in a sealed microwave vial at 100° C. for 18 hours. Then, the whole was stirred at rt when 2 mL of HCl 5% in water was added. This was stirred for 30 mM to show by LCMS mostly desired product as well as side products. The whole was extracted with AcOEt and worked up. The product is purified by normal chromatography using 0-100% acetone in hexanes. Product was further purified using semi-prep HPLC using 40-60% MeCN in AmFor 10 mM buffer. The product was then lyophilized and isolated as a white solid (5. 1 mg, 25%). 1H NMR (500 MHz, CDCl3) δ 9.06-8.82 (m, 0.1H)M 8.44-7.94 (m, 3.61H), 7.10 (td, J=9.2, 4.3 Hz, 1H), 7.02-6.83 (m, iH), 6.77-6.66 (m, 1H), 6.46-6.27 (m, 0.6H), 5.98-5.81 (m, 0.4H), 5.75-5.56 (m, 0.6H), 5.31-5.12 (m, 0.4H), 4.16-3.60 (m, 2H), 2.50 (s, 4H), 2.22-2.03 (m, iH). MS (m/z); 409.2 [M+1], >99%.

Example 32. (R)-5-(2-(2,5-difluorophenyl)pyrrolidin-1-yl)-3-(4-(methoxymethyl)-1H-pyrazol-1-yl) pyrazolo[1,5-aJpyrimidine (I-226)

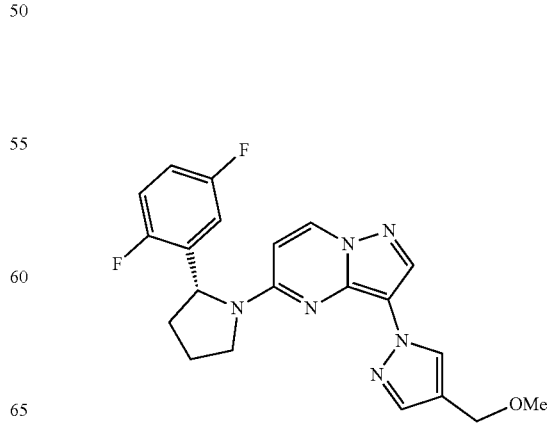

117

(R)-5-(2-(2,5-difluorophenyl)pyrrolidin-1-yl)-3-(4-(methoxymethyl)-1H-pyrazol-1-yl)pyrazolo[1,5-a]pyrimidine

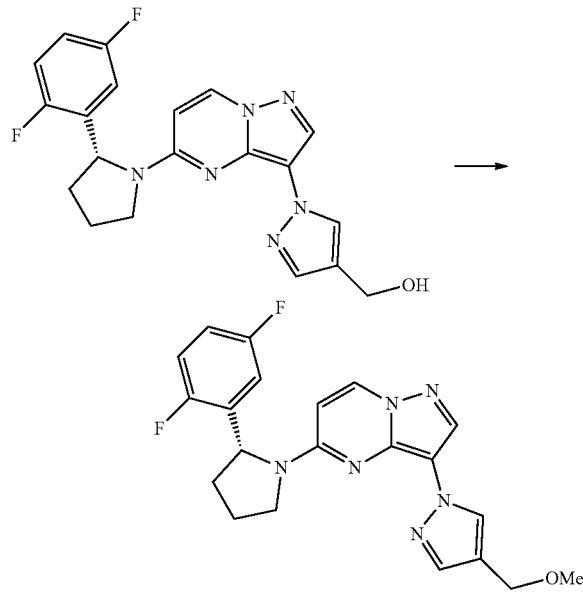

118

To a mixture of DMSO (316 uL, 4.45 mmol) in DCM (10 mL), Oxalylchloride (229 uL, 2.67 mmol) was added and stirred at −78° C. for 15 min. Solution of (R)-(1-(5-(2-(2,5-difluorophenyl)pyrrolidin-1-yl)pyrazolo[1,5-a]pyrimidin-3-yl])-1H-pyrazol-4-yl)methanol (705.5 mg, 1.78 mmol) was then added with 8 mL of DCM and then triethylamine (1.25 mL, 8.899 mmol) was added and the mixture was brought to rt. Upon stirring for 1 h, LCMS indicated many products but no more SM. A major side product is observed at 1.65 min (m/ζ=411) upon quenching with methanol. The whole was extracted with AcOEt and washed with water. The organic layer is dried and concentrated. The side product was purified by normal chromatography using 0-100% acetone hexanes and by reverse chromatography using 0-100% MeCN in ArnFor buffer to afford title compound as an off-white solid (60.4 mg, 8%). 1H NMR (500 MHz, DMSQ) δ 8.70 (d, J=6.7 Hz, 1H), 8.46-8.13 (m, 1H), 7.75 (s, 1H), 7.65-7.46 (m, 1H), 7.28 (s, 1H), 7.20-6.87 (m, 2H), 6.61 (d, J=6.6 Hz, 1H). 5.50-5.25 (m, 1H), 4.49-4.19 (m, 2H, 4.01 (dt, J=11.2, 5.8 Hz, 1H), 3.80-3.59 (m, 1H), 3.25 (s, 3H), 2.48-2.36 (m, 1H), 2.14-1.81 (m, Mh). MS (m/z): 411.3 [M+H]+, >99%.

| Cmp. ID | Prepared as in | ¹H NMR | Purity (%) | MS (m/z) |
|---|---|---|---|---|
| I-147 | Example 1 | ¹H NMR (500 MHz, DMSO) δ 8.74 (d, J = 7.6 Hz, 1H), 8.62-8.17 (m, 2H), 8.03 (s, 1H), 7.39-6.89 (m, 3H), 6.64 (d, J = 7.7 Hz, 0.85H), 6.06 (br s, 0.15H), 5.44 (d, J = 6.9 Hz, 1H), 4.10-3.96 (m, 1H), 3.82-3.57 (m, 1H), 2.48-2.40 (m, 1H), 2.16-1.77 (m, 3H). | 97 | 435.2 |
| I-148 | Example 1 | 1H NMR (400 MHz, DMSO) δ 8.75-8.46 (m, 1H), 8.28-8.10 (m, 1H), 7.55 (s, 1H), 7.48-7.26 (m, 2H), 7.22-6.89 (m, 2H), 6.61 (d, J = 7.4 Hz) and 6.10-5.95 (m) (1H), 5.46-5.29 (m, 1H), 4.05-3.97 (m, 1H), 3.84-3.59 (m, 1H), 2.58-2.39 (m, 1H), 2.22-2.00 (m, 5H), 1.97-1.80 (m, 1H). | 100 | 381.2 |
| I-149 | Example 1 | 1H NMR (400 MHz, DMSO) δ 8.77 (d, J = 7.3 Hz) and 8.63-8.53 (m) (1H), 8.24 (s, 1H), 8.21-8.10 (m, 1H), 8.03 (s, 1H), 7.75-7.63 and 7.52-7.39 (m, 4H), 7.33-6.92 (m, 4H), 6.66 (d, J = 7.7 Hz) and 6.12-6.02 (m) (1H), 5.59 (d, J = 6.5 Hz) and 5.43-5.29 (m) (1H), 4.12-4.00 (m, 1H), 3.86-3.59 (m, 1H), 2.57-2.40 (m, 1H), 2.15-1.82 (m, 3H). | 99 | 443.1 |
| I-150 | Example 1 | 1H NMR (400 MHz, DMSO) δ 8.74-8.64 (m, 1H), 8.14-8.05 (m, 1H), 7.47 (s, 1H), 7.37-7.25 (m, 1H), 7.17-7.00 (m, 2H), 6.66-6.56 (m, 1H), 5.44-5.33 (m, 1H), 4.04-3.96 (m, 1H), 3.76-3.61 (m, 1H), 2.55-2.41 (m, 1H), 2.18-2.02 (m, 5H), 1.96 (s, 3H), 1.91-1.81 (m, 1H). | 98 | 395.2 |
| I-151 | Example 1 | 1H NMR (400 MHz, DMSO) δ 8.74 (d, J = 7.6 Hz) and 8.62-8.53 (m) (1H), 8.51-8.45 (m) and 8.19 (s) (1H), 7.92 (s, 1H), 7.56-7.45 (m, 2H), 7.38-7.28 (m, 3H), 7.22-6.94 and 6.87-6.72 (m, 3H), 6.64 (d, J = 7.6 Hz) and 6.10-6.01 (m) (1H), 5.56-5.49 and 5.41-5.31 (m, 1H), 4.09-3.98 (m, 1H), 3.77-3.58 (m, 1H), 2.54-2.30 (m, 4H), 2.12-1.80 (m, 3H). | 97 | 457.0 |
| I-153 | Example 1 | 1H NMR (400 MHz, DMSO) δ 9.15-9.04 (m) and 8.90 (s) and 8.78 (d, J = 6.7 Hz) (2H), 8.71-8.56 (m, 1H), 8.53-8.46 (m, 2H), 8.41-8.23 (m, 2H), 7.41-6.93 (m, 3H), 6.67 (d, J = 8.4 Hz) and 6.13-6.05 (m) (1H), 5.62-5.52 and 5.41-5.30 (m, 1H), 4.14-3.99 (m, 1H), 3.87-3.62 (m, 1H), 2.54-2.39 (m, 1H), 2.12-1.83 (m, 3H). | 100 | 445.4 |

-continued

| Cmp. ID | Prepared as in | ¹H NMR | Purity (%) | MS (m/z) |
|---|---|---|---|---|
| I-155 | Example 1 | 1H NMR (400 MHz, DMSO) δ 8.76-8.49 (m, 1H), 8.43-8.29 (m) and 7.67 (s) (1H), 8.15 (s, 1H), 7.59-7.46 (m, 1H), 7.37-6.91 (m, 3H), 6.68-6.56 and 6.10-5.96 (m, 1H), 5.47-5.30 (m, 1H), 5.01-4.82 (m, 1H), 4.53-4.32 (m, 2H), 4.06-3.98 (m, 1H), 3.81-3.62 (m, 1H), 2.55-2.41 (m, 1H), 2.17-1.82 (m, 3H). | 100 | 397.2 |
| I-156 | Example 1 | 1H NMR (400 MHz, DMSO) δ 8.71 (d, J = 6.3 Hz) and 8.63-8.47 (m) (1H), 8.36-8.24 (m) 7.57 (s) (1H), 8.22-8.10 (m, 1H), 7.53-7.37 (m, 1H), 7.36-7.24 (m, 1H), 7.22-6.91 (m, 2H), 6.68-6.53 and 6.10-5.96 (m, 1H), 5.49-5.31 (m, 1H), 4.70 (t, J = 5.3 Hz, 1H), 4.02 (dt, J = 11.3, 5.7 Hz, 1H), 3.80-3.45 (m, 3H), 2.71-2.39 (m, 3H), 2.16-1.79 (m, 3H). | 100 | 411.1 |
| I-158 | Example 3 | ¹H NMR (500 MHz, DMSO) δ 8.82-8.47 (m, 1H), 8.29-8.13 (m, 1H), 8.09-7.50 (m, 4H), 7.42-6.88 (m, 3H), 6.73-6.55 and 6.19-5.94 (m, 1H), 5.67-5.26 (m, 1H), 4.12-3.97 (m, 1H), 3.97-3.83 (m, 3H), 3.83-3.59 (m, 1H), 2.48-2.40 (m, 1H), 2.21-1.80 (m, 3H). | 100 | 447.2 |
| I-159 | Example 3 | ¹H NMR (500 MHz, CDCl₃) δ 8.96-8.44 (m, 2H), 8.40-8.08 (m, 3H), 7.99-7.72 (m, 2H), 7.45-7.31 (m, 1H), 7.09-6.81 (m, 2H), 6.78-6.69 (m, 1H), 6.42-5.81 (m, 1H), 5.75-5.16 (m, 1H), 4.14-3.65 (m, 2H), 2.57-2.43 (m, 1H), 2.22-2.03 (m, 3H). | 100 | 444.3 |
| I-160 | Example 3 | ¹H NMR (500 MHz, CDCl3) δ 9.03-8.54 (m, 2H), 8.50-8.08 (m, 3H), 8.07-7.88 (m, 1H), 7.80-7.33 (m, 2H), 7.12-6.78 (m, 2H), 6.77-6.64 (m, 1H), 6.46-5.85 (m, 1H), 5.78-5.16 (m, 1H), 4.18-3.63 (m, 2H), 2.59-2.45 (m, 1H), 2.23-2.05 (m, 3H). | 100 | 444.3 |
| I-161 | Example 3 | ¹H NMR (500 MHz, DMSO) δ 8.98 (br s, 0.3H), 8.80 (d, J = 7.2 Hz, 1H), 8.63 (br s, 0.7H), 8.47-8.32 (m, 2H), 8.31-8.20 (m, 3H), 7.80 (br s, 0.5H), 7.64 (s, 1H), 7.38 (br s, 0.5H), 7.24 (br s, 0.5H), 7.11-7.02 (m, 2H), 7.02-6.93 (m, 0.5H), 6.70 (d, J = 7.4 Hz, 1H), 6.12 (br s, 0.5H), 5.70-5.58 (m, 1H), 4.10 (s, 1H), 3.99 (s, 3H), 3.91-3.79 (m, 1H), 3.75-3.66 (m, 1H), 2.16-2.03 (m, 2H), 1.98-1.87 (m, 1H). | 99 | 474.3 |
| I-162 | Example 3 | ¹H NMR (500 MHz, DMSO) δ 8.85-8.65 (m, 1H), 8.63-7.89 (m, 3H), 7.77-6.88 (m, 6H), 6.72-6.58 and 6.13-5.99 (m, 1H), 5.66-5.29 (m, 1H), 4.13-3.99 (m, 1H), 3.91-3.58 (m, 1H), 2.48-2.39 (m, 1H), 2.16-1.80 (m, 3H). | 99 | 449.1 |
| I-163 | Example 3 | ¹H NMR (500 MHz, DMSO) δ 9.25-8.91 (m, 3H), 8.85-8.14 (m, 4H), 7.42-6.85 (m, 3H), 6.74-6.61 and 6.20-6.01 (m, 1H), 5.69-5.30 (m, 1H), 4.17-3.98 (m, 1H), 3.93-3.61 (m, 1H), 2.48-2.40 (m, 1H). 2.19-1.80 (m, 3H). | 98 | 445.2 |
| I-164 | Example 3 | ¹H NMR (500 MHz, DMSO) δ 8.84-8.49 (m, 1H), 8.33-7.96 (m, 2H), 7.96-7.82 (m, 1H), 7.80-7.65 (m, 1H), 7.41-6.86 (m, 3H), 6.72-6.58 (m, 1H), 6.15-6.00 (m, 1H), 5.63-5.28 (m, 1H), 4.12-3.97 (m, 1H), 3.89-3.58 (m, 1H), 2.78-2.62 (m, 3H), 2.47-2.40 (m, 1H), 2.15-1.81 (m, 3H). | 97 | 464.1 |
| I-165 | Example 3 | ¹H NMR (500 MHz, DMSO) δ 8.94-8.71 (m, 1H), 8.64-8.07 (m, 3H), 7.87-7.64 (m, 1H), 7.45-7.28 (m, 1H), 7.27-6.89 (m, 2H), 6.78-6.63 (m, 1H), 6.63-6.48 (m, 1H), 6.38-6.24 and 6.13-6.03 (m, 1H), 5.65-5.30 (m, 1H), 4.15-3.99 (m, 1H), 3.88-3.58 (m, 1H), 3.56-3.38 (m, 3H), 2.49-2.38 (m, 1H), 2.16-1.80 (m, 3H). | 99 | 474.2 |
| I-166 | Example 1 | ¹H NMR (500 MHz, CDCl₃) δ 8.18 (br s, 1H), 8.00 (s, 1H), 7.09-6.79 (m, 2H), 6.75-6.60 (m, 1H), 6.37-5.68 (m, 1H), 5.64-5.12 (m, 2H), 3.90 (s, 4H), 3.78-3.60 (m, 1H), 2.53-2.35 (m, 1H), 2.11-1.96 (m, 3H), 1.79-1.48 (m, 3H). | 100 | 411.2 |
| I-167 | Example 1 | ¹H NMR (500 MHz, CDCl₃) δ 8.15 (br s, 1H), 7.98 (s, 1H), 7.04-6.96 (m, 1H), 6.93-6.85 (m, 1H), 6.76-6.71 (m, 1H), 5.96-5.82 (m, 1H), 5.50-5.36 (m, 2H), 3.94-3.68 (m, 5H), 2.48-2.38 (m, 1H), 2.28 (s, 3H), 2.05-1.96 (m, 3H). | 98 | 411.2 |
| I-168 | Example 1 | 1H NMR (400 MHz, DMSO) δ 9.09-9.00 (m) and 8.77 (d, J = 7.1 Hz) (1H), 8.64-8.55 (m) and 8.36-8.05 (m) (3H), 7.39-6.85 (m, 3H), 6.73-6.61 and 6.14-6.04 (m, 1H), 5.48-5.30 (m, 1H), 4.05-3.96 (m, 1H), 3.81-3.63 (m, 1H), 2.56-2.38 (m, 1H), 2.15-1.81 (m, 3H). | 100 | 368.2 |
| I-169 | Example 1 | 1H NMR (400 MHz, DMSO) δ 8.78-8.67 and 8.59-8.50 (m, 1H), 8.37-8.28 (m) and 7.71 (s) (1H), 8.16 (s, 1H), 7.59-7.45 (m, 1H), 7.37-7.03 (m, 2H), 6.99-6.91 (m, 1H), 6.65-6.57 and 6.07-5.97 (m, 1H), 5.58-5.49 and 5.41-5.29 (m, 1H), 4.97-4.77 (m, 1H), 4.08-3.98 (m, 1H), 3.81-3.56 (m, 1H), 2.57-2.37 (m, 1H), 2.12-1.82 (m, 3H), 1.54-1.31 (m, 6H). | 100 | 425.1 |

-continued

| Cmp. ID | Prepared as in | ¹H NMR | Purity (%) | MS (m/z) |
|---|---|---|---|---|
| I-171 | Example 3 | ¹H NMR (500 MHz, DMSO) δ 13.04-12.70 (m, 1H), 8.81-8.48 (m, 1H), 8.30-7.57 (m, 5H), 7.37-6.80 (m, 3H), 6.71-6.53 and 6.13-5.96 (m, 1H), 5.65-5.28 (m, 1H), 4.11-3.98 (m, 1H), 3.86-3.61 (m, 1H), 2.48-2.41 (m, 1H), 2.14-1.81 (m, 3H). | 100 | 433.2 |
| I-172 | Example 1 | 1H NMR (400 MHz, DMSO) δ 8.77-8.66 and 8.60-8.48 (m, 1H), 8.23-8.10 (m, 1H), 7.56 (s, 1H), 7.47-6.90 (m, 4H), 6.68-6.53 and 6.09-5.97 (m, 1H), 5.58-5.28 (m, 1H), 4.08-3.97 (m, 1H), 3.86-3.57 (m, 1H), 3.66 (s, 3H), 2.57-2.37 (m, 1H), 2.14-1.78 (m, 3H). | 100 | 397.2 |
| I-177 | Example 6 | ¹H NMR (500 MHz, CDCl₃) δ 8.38-7.97 (m, 3H), 7.75 (s, 1H), 7.08 (td, J = 9.2, 4.3 Hz, 1H), 7.01-6.81 (m, 1H), 6.74-6.66 (m, 1H), 6.42-6.19 (m, 0.5H), 5.97-5.76 (m, 0.5H), 5.71-5.50 (m, 0.5H), 5.27-5.09 (m, 0.5H), 4.13-3.54 (m, 2H), 2.58-2.34 (m, 1H), 2.15-1.83 (m, 7H), 1.30-1.10 (m, 6H). | 99 | 471.3 |
| I-188 | Example 7 | ¹H NMR (500 MHz, CDCl₃) δ 8.37-8.14 (m, 2H), 7.90 (br s, 1H), 7.66 (br s, 1H), 7.13-7.03 (m, 1H), 6.96-6.84 (m, 1H), 6.78-6.66 (m, 1H), 6.43-6.20 (m, 1H), 6.03-5.83 (m, 1H), 5.74-5.54 (m, 1H), 5.02-4.62 (m, 4H), 4.04-3.63 (m, 2H), 2.59-2.39 (m, 1H), 2.22-2.00 (m, 3H). | 100 | 435.3 |
| I-189 | Example 7 | ¹H NMR (500 MHz, CDCl₃) δ 8.37-8.21 (m, 2H), 8.02 (br s, 1H), 7.69 (br s, 1H), 7.63 (s, 1H), 7.49 (t, J = 1.7 Hz, 1H), 7.06-6.68 (m, 3H), 6.59 (s, 1H), 6.40-5.84 (m, 1H), 5.73-5.13 (m, 1H), 4.00-3.66 (m, 2H), 2.57-2.44 (m, 1H), 2.21-2.02 (m, 3H). | 100 | 433.3 |
| I-190 | Example 3 | ¹H NMR (500 MHz, CDCl₃) δ 8.91-8.51 (m, 1.5H), 8.39-8.12 (m, 3.5H), 7.87 (s, 1H), 7.57-7.39 (m, 1H), 7.11-7.03 (m, 1H), 6.89 (s, 1H), 6.73 (s, 1H), 6.38 (s, 0.7H), 5.96-5.84 (m, 0.3H), 5.69 (s, 0.7H), 5.28-5.14 (m, 0.3H), 4.15-3.87(m, 1H), 3.69 (s, 1H), 2.51 (s, 1H), 2.22-2.12 (m, 2H), 2.11-2.01 (m, 1H). | 99 | 462.2 |
| I-191 | Example 3 | ¹H NMR (500 MHz, CDCl₃) δ 9.11-8.80 (m, 1H), 8.75 (d, J = 1.9 Hz, 1H), 8.49-8.06 (m, 3H), 8.01-7.85 (m, 2H), 7.12 (td, J = 9.3, 4.3 Hz, 1H), 6.90 (s, 1H), 6.73 (s, 1H), 6.38 (s, 0.7H), 6.01-5.82 (m, 0.3H), 5.71 (s, 0.7H), 5.32-5.16 (m, 0.3H), 3.93 (s, 1H), 3.70 (s, 1H), 2.50 (s, 1H), 2.23-2.01 (m, 3H). | 97 | 469.2 |
| I-192 | Example 14 | 1H NMR (400 MHz, DMSO) δ 8.79-8.74 (m) and 8.70 (d, J = 7.8 Hz) (1H), 8.53-8.47 (m) and 8.35-8.29 (m) and 8.28-8.17 (m) (3H), 8.15-8.09 (m) and 8.03 (s) (1H), 7.71-7.58 and 7.52-7.38 (m, 5H), 7.33-7.22 (m, 2H), 6.63 (d, J = 7.9 Hz) and 6.08-6.03 (m) (1H), 5.72-5.65 and 5.55-5.48 (m, 1H), 3.92-3.83 (m, 1H), 3.81-3.72 (m, 1H), 2.59-2.46 (m, 1H), 2.25-1.92 (m, 3H). | 100 | 426.1 |
| I-193 | Example 2 | 1H NMR (400 MHz, DMSO) δ 8.80-8.69 (m, 1H), 8.59-8.48 (m) and 8.23 (s) and 8.21 (s) (2H), 8.15-8.08 (m) and 8.04 (s) (1H), 7.71-7.55 (m, 3H), 7.50-7.37 (m, 2H), 7.28 (t, J = 7.2 Hz, 1H), 7.07-6.99 (m, 1H), 6.64 (d, J = 7.7 Hz) and 6.13-6.05 (m) (1H), 5.60 (d, J = 6.8 Hz) and 5.49-5.41 (m) (1H), 3.98-3.82 (m, 1H), 3.74 (dd, J = 16.7, 7.2 Hz, 1H), 2.55-2.40 (m, 1H), 2.24-1.93 (m, 3H). | 100 | 444.1 |
| I-194 | Example 3 | 1H NMR (400 MHz, DMSO) δ 9.06-8.96 and 8.81-8.72 (m, 1H), 8.64-8.54 and 8.48-8.24 and 8.19-8.04 (m, 5H), 7.53-7.42 (m, 1H), 7.39-7.28 (m) and 7.23-7.15 (m) and 7.08-6.94 (m) (3H), 6.66 (d, J = 7.8 Hz) and 6.10-6.04 (m) (1H), 5.61-5.51 and 5.41-5.31 (m, 1H), 4.11-3.98 (m, 1H), 3.87-3.61 (m, 1H), 2.57-2.39 (m, 1H), 2.13-1.83 (m, 3H). | 99 | 462 |
| I-196 | Example 18 | ¹H NMR (500 MHz, CDCl₃) δ 8.22 (s, 1H), 8.15 (d, J = 7.6 Hz, 1H), 7.83 (s, 1H), 7.44 (s, 1H), 7.42-7.34 (m, 4H), 7.30-7.27 (m, 1H), 6.03 (d, J = 7.6 Hz, 1H), 5.25 (br s, 1H), 5.09 (br s, 1H), 2.18 (s, 3H), 1.61 (d, J = 6.8 Hz, 3H). | 99 | 319.2 |
| I-199 | Example 3 | ¹H NMR (500 MHz, CDCl₃) δ 9.43 (br s, 0.3H), 9.24 (s, 0.7H), 9.14 (dd, J = 5.4, 1.1 Hz, 1H), 8.99 (br s, 0.5H), 8.48-8.30 (m, 2H), 8.17 (br s, 0.5H), 8.10-7.94 (m, 1H), 7.62-7.46 (m, 1H), 7.11 (td, J = 9.2, 4.3 Hz, 1H), 6.89 (s, 1H), 6.74 (s, 1H), 6.39 (s, 0.7H), 5.93 (br s, 0.3H), 5.72 (s, 0.7H), 5.24 (br s, 0.3H), 3.93 (s, 1H), 3.70 (s, 1H), 2.52 (s, 1H), 2.23-2.05 (m, 3H). | 100 | 445.2 |
| I-200 | Example 3 | ¹H NMR (500 MHz, CDCl3) δ 8.68 (br s, 0.5H), 8.46-8.01 (m, 3.5H), 7.90-7.59 (m, 2H), 7.12-6.84 (m, 2H), 6.82 (dd, J = 8.5, 0.7 Hz, 1H), 6.73 (s, 1H), 6.34 (br s, 0.6H), 5.90 (br s, 0.4H), 5.65 (br s, 0.6H), 5.23 (br s, 0.4H), 4.15-3.60 (m, 5H), 2.50 (s, 1H), 2.22-1.96 (m, 3H). | 100 | 474.2 |
| I-201 | Example 3 | ¹H NMR (500 MHz, CDCl3) δ 8.96-8.65 (m, 1H), 8.48-8.14 (m, 3H), 8.06 (s, 1H), 7.13-6.82 (m, 3H), 6.73 (s, | 99.9 | 474.2 |

-continued

| Cmp. ID | Prepared as in | ¹H NMR | Purity (%) | MS (m/z) |
|---|---|---|---|---|
| | | 1H), 6.41-6.15 (m, 1H), 5.97-5.81 (m, 1H), 5.76-5.53 (m, 1H), 4.09-3.61 (m, 5H), 2.51 (s, 1H), 2.18-2.03 (m, 3H). | | |
| I-202 | Example 3 | ¹H NMR (500 MHz, CDCl₃) δ 8.99 (br s, 1H), 8.35 (s, 1H), 8.22 (s, 1H), 8.11-8.03 (m, 2H), 7.83 (brs, 1H), 7.19-6.61 (m, 4H), 6.31 (br s, 0.4H), 5.91 (br s, 0.6H), 5.62 (br s, 0.4H), 5.30 (br s, 0.6H), 4.20-3.62 (m, 5H), 2.53 (s, 1H), 2.17-1.99 (m, 3H). | 99.8 | 474.2 |
| I-203 | Example 3 | ¹H NMR (500 MHz, CDCl₃) δ 9.07-8.95 (m, 0.5H), 8.84 (s, 1H), 8.68 (s, 1H), 8.40-8.08 (m, 2.5H), 7.92 (s, 1H), 7.47 (br s, 0.5H), 7.16-6.88 (m, 1.5H), 6.75 (s, 1H), 6.35 (s, 1H), 5.95-5.57 (m, 3H), 5.20 (s, 1H), 4.20-3.86 (m, 2.H), 3.82-3.56 (m, 1H), 2.52 (s, 1H), 2.17-2.04 (m, 2H). | 100 | 487.2 |
| I-204 | Example 3 | ¹H NMR (500 MHz, CDCl₃) δ 9.04 (s, 0.5H), 8.45-8.08 (m, 4.5H), 7.58-7.29 (m, 1H), 7.13-6.64 (m, 3H), 6.34 (br s, 1H), 6.03-5.55 (m, 1H), 5.30 (br s, 1H), 4.20-3.55 (m, 5H), 2.53 (s, 1H), 2.20-1.98 (m, 3H). | 100 | 474.2 |
| I-205 | Example 3 | ¹H NMR (500 MHz, CDCl₃) δ 9.17-8.96 (m, 0.5H), 8.58-8.14 (m, 4.5H), 8.07 (s, 1H), 7.63-7.35 (m, 1H), 7.16-6.80 (m, 2.5H), 6.74 (s, 1H), 6.37 (s, 0.5H), 5.89 (s, 0.5H), 5.80-5.60 (m, 0.5H), 5.37-5.14 (m, 1H), 3.99-3.63 (m, 2H), 2.62-2.43 (m, 1H), 2.19-2.06 (m, 3H). | 100 | 462.3 |
| I-207 | Example 21 | ¹H NMR (500 MHz, CDCl₃) δ 8.65 (s, 2H), 8.48 (s, 1H), 8.31 (s, 1H), 8.27 (d, J = 6.7 Hz, 1H), 7.95 (s, 1H), 7.51 (s, 2H), 7.22 (s, 1H), 6.65 (s, 1H), 6.33 (d, J = 6.3 Hz, 1H), 5.73 (s, 1H), 3.97 (s, 1H), 3.73 (d, J = 6.8 Hz, 1H), 2.52 (s, 1H), 2.42 (s, 1H), 2.22-2.07 (m, 2H). | 100 | 445.2 |
| I-210 | Example 8 | ¹H NMR (500 MHz, CDCl₃) δ 8.36-8.03 (m, 2H), 7.90-7.39 (m, 2H), 7.11-7.01 (m, 1H), 6.99-6.83 (m, 1H), 6.79-6.67 (m, 1H), 6.41-5.76 (m, 1H), 5.71-5.05 (m, 1H), 4.17-4.09 (m, 1H), 4.07-4.00 (m, 1H), 3.99-3.84 (m, 2H), 3.77-3.26 (m, 3H), 2.57-2.43 (m, 1H), 2.39-2.28 (m, 1H), 2.19-1.86 (m, 4H). | 99 | 437.3 |
| I-211 | Example 21 | ¹H NMR (500 MHz, CDCl₃) δ 8.48 (s, 1H), 8.33 (s, 1H), 8.27 (s, 1H), 8.25-8.15 (m, 2.7H), 8.11-7.99 (m, 0.3H), 7.85 (s, 1H), 7.42 (s, 1H), 7.24-7.14 (m, 1H), 7.11-6.96 (m, 1H), 6.31 (s, 1H), 5.74 (s, 1H), 3.95 (s. 4H), 3.71 (s, 1H), 2.50 (s, 1H), 2.37 (s, 1H), 2.11-2.01 (m, J = 7.6 Hz, 2H). | 97 | 457.8 |
| I-212 | Example 7 | ¹H NMR (500 MHz, CDCl₃) δ 8.30 (s, 2H), 7.92-7.48 (m, 2H), 7.10-7.02 (m, 1H), 6.94-6.81 (m, 1H), 6.77-6.69 (m, 1H), 6.68-6.60 (m, 1H), 6.41-6.00 (m, 1H), 5.85-5.47 (m, 1H), 4.48 (t, J = 9.5 Hz, 2H), 4.04-3.62 (m, 2H), 2.97-2.80 (m, 2H), 2.53-2.36 (m, 1H), 2.20-1.98 (m, 3H). | 97 | 435.2 |
| I-213 | Example 21 | ¹H NMR (500 MHz, CDCl₃) δ 8.69-8.58 (m, 2H), 8.56-8.51 (m, 1H), 8.32-8.17 (m, 3H), 7.98-7.91 (m, 1H), 7.60-7.51 (m, 2H), 7.19-7.12 (m, 1H), 7.08-7.01 (m, 1H), 6.37-6.30 (m, 1H), 5.83-5.76 (m, 1H), 4.02-3.92 (m, 1H), 3.80-3.72 (m, 1H), 2.61-2.51 (m, 1H), 2.44-2.34 (m, 1H), 2.21-2.11 (m, 2H). | 100 | 427.2 |
| I-215 | Example 14 | ¹H NMR (500 MHz, CDCl₃) δ 8.34-8.14 (m, J = 30.5 Hz, 3H), 7.81-7.70 (m, 1H), 7.43-7.32 (m, 1H), 7.18-7.08 (m, 1H), 6.38-6.29 (m, 1H), 5.76-5.66 (m, 1H), 4.06-3.92 (m, 1H), 3.78-3.68 (m, 1H), 2.57-2.37 (m, 2H), 2.24-2.03 (m, 2H). | 99 | 418.2 |
| I-218 | Example 26 | ¹H NMR (500 MHz, CDCl₃) δ 8.29-7.92 (m, 3H), 7.46-7.32 (m, 1H), 7.22-7.09 (m, 1H), 6.29-5.91 (m, 2H), 5.64-5.10 (m, 1H), 4.39-4.20 (m, 1H), 4.04-3.61 (m, 2H), 2.84-2.70 (m, 3H), 2.53-2.28 (m, 2H), 2.19 (s, 3H), 2.16-2.01 (m, 2H). | 99 | 393.3 |
| I-222 | Example 21 | ¹H NMR (500 MHz, CDCl₃) δ 8.42 (dd, J = 2.4, 0.6 Hz, 1H), 8.32-7.95 (m, 4H), 7.85-7.75 (m, 2H), 7.21-6.99 (m, 2H), 6.84 (d, J = 8.5 Hz, 1H), 6.37-6.25 (m, 1H), 5.80-5.68 (m, 1H), 4.00 (s, 3H), 3.99-3.94 (m, 1H), 3.80-3.67 (m, 1H), 2.59-2.33 (m, 2H), 2.20-2.04 (m, 2H). | 99.6 | 457.3 |
| I-224 | Example 3 | ¹H NMR (500 MHz, CDCl₃) δ 8.83-8.48 (m, 2H), 8.38-8.04 (m, 3H), 7.92-7.72 (m, 1H), 7.12-7.01 (m, 1H), 6.97-6.81 (m, 1H), 6.78-6.68 (m, 1H), 6.42-6.26 (m, 0.7H), 5.97-5.83 (m, 0.3H), 5.72-5.54 (m, 0.7H), 5.30-5.13 (m, 0.3H), 4.08 (s, 3H), 3.98-3.86 (m, 1H), 3.79-3.64 (m, 1H), 2.60-2.43 (m, 1H), 2.25-1.97 (m, 3H). | 100 | 457.3 |

Example 33: TrkA Kinase Assay Protocol

TrkA kinase domain was supplied by SignalChem. Ulight PolyGT peptide substrate and Europium labeled W1024 antiphosphotyrosine antibody were supplied by Perkin Elmer. Assay buffer contained 50 mM HEPES, 10 mM $MgCl_2$, 1 mM EGTA, 2 mM DTT, 0.1 mg/mL BSA, and 0.005% w/v tween 20, pH 7.5. Enzyme dilution buffer was made by supplementing assay buffer with 25% w/v glycerol. Antibody dilution buffer contained 20 mM Tris, 137 mM NaCl, and 0.05% w/v tween 20, pH 8.0. Buffers were prepared at room temperature. Enzyme solutions were made on ice, while other solutions were made at room temperature and all subsequent assay steps were performed at room temperature. The TrkA stock solution (0.1 mg/mL) was diluted 156× in enzyme dilution buffer and then 100× in assay buffer. Five pL/well of enzyme solution was added to the assay plate (Greiner black 384-well nonbinding plate), with buffer containing no enzyme added to negative control wells. Test compounds were serially diluted in DMSO at 300× final assay concentration. One μL of each test compound dilution was mixed with 99 pL assay buffer plus ATP (30 μM) and five pL of each test compound-ATP solution was added to $w^{3/4}13$ s containing enzyme. Positive control wells contained enzyme and substrates but no test compounds. After a 15 minute enzyme-test compound preincubation, five pL of substrate diluted in assay buffer was added to all wells. Final assay concentrations were 33 pM TrkA, 100 nM peptide substrate, and 10 pM ATP. After a five minute reaction, five pL of 80 mM EDTA was added, followed five minutes later by five pL two nM antibody solution. The ratio of fluorescence at 665 nm vs. 615 nM in each well was determined using a Tecan Infinite Pro F200 plate reader. For each test compound well, percent inhibition $w^{3/4}$s calculated (% inliib=100−100*(test value− neg. control)/(pos. control-neg. control)). Percent inhibition values were fit to a four parameter logistic to determine $IC_{50}$ values for each test compound.

Table 1. Trk Kinase activity' of compounds of the present disclosure in the Trk kinase biochemical assay. 4444 indicates an $IC_{50}$ of less than about 10 nM, 444 indicates an $IC_{50}$ between about 10 nM and about 50 nM, ++ indicates an $IC_{50}$ between about 50 nM and about 500 nm, and + indicates an $IC_{50}$ greater than 500 nM.

TABLE 1

| Cmp No. | TrkA WT $IC_{50}$ (nM) |
|---|---|
| I-147 | ++++ |
| I-148 | ++++ |
| I-149 | ++++ |
| I-150 | ++++ |
| I-151 | ++++ |
| I-152 | ++++ |
| I-153 | ++++ |
| I-154 | ++++ |
| I-155 | ++++ |
| I-156 | ++++ |
| I-157 | ++++ |
| I-158 | ++++ |
| I-159 | ++++ |
| I-160 | ++++ |
| I-161 | ++++ |
| I-162 | ++++ |
| I-163 | ++++ |
| I-164 | ++++ |
| I-165 | ++++ |
| I-166 | ++++ |
| I-167 | ++++ |
| I-168 | ++++ |
| I-169 | ++++ |
| I-170 | ++++ |
| I-171 | ++++ |
| I-172 | ++++ |
| I-173 | ++++ |
| I-174 | ++++ |
| I-175 | ++++ |
| I-176 | ++++ |
| I-177 | ++++ |
| I-178 | ++++ |
| I-179 | ++++ |
| I-180 | ++++ |
| I-181 | ++++ |
| I-182 | ++++ |
| I-183 | ++++ |
| I-184 | ++++ |
| I-185 | ++++ |
| I-186 | ++++ |
| I-187 | ++++ |
| I-188 | ++++ |
| I-189 | ++++ |
| I-190 | ++++ |
| I-191 | ++++ |
| I-192 | ++++ |
| I-193 | ++++ |
| I-194 | ++++ |
| I-195 | ++++ |
| I-196 | ++++ |
| I-197 | ++++ |
| I-198 | ++++ |
| I-199 | ++++ |
| I-200 | ++++ |
| I-201 | ++++ |
| I-202 | ++++ |
| I-203 | ++++ |
| I-204 | ++++ |
| I-205 | ++++ |
| I-206 | ++++ |
| I-207 | ++++ |
| I-208 | ++++ |
| I-209 | ++++ |
| I-210 | ++++ |
| I-211 | ++++ |
| I-212 | ++++ |
| I-213 | ++++ |
| I-214 | ++++ |
| I-215 | ++++ |
| I-216 | ++++ |
| I-217 | ++++ |
| I-218 | ++++ |
| I-219 | ++++ |
| I-220 | ++++ |
| I-221 | ++++ |
| I-222 | ++++ |
| I-223 | ++++ |
| I-224 | ++++ |
| I-225 | ++++ |
| I-226 | ++++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound having a structure:
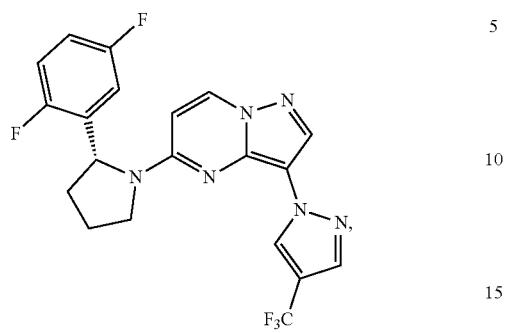
or a pharmaceutically acceptable salt thereof.
2. A pharmaceutical composition comprising a therapeutically effective amount of the compound of claim 1 or a pharmaceutically acceptable salt thereof, and a pharmaceutically acceptable carrier.
* * * * *